(12) United States Patent  
Xu et al.

(10) Patent No.: US 12,281,163 B2
(45) Date of Patent: *Apr. 22, 2025

(54) DIMERS AND USE THEREOF

(71) Applicant: JIANGSU ALPHAMAB BIOPHARMACEUTICALS CO., LTD., Jiangsu (CN)

(72) Inventors: Ting Xu, Suzhou (CN); Kangping Guo, Suzhou (CN); Dong Yang, Suzhou (CN); Pilin Wang, Suzhou (CN); Yuhao Jin, Suzhou (CN); Xiaoxiao Wang, Suzhou (CN)

(73) Assignee: JIANGSU ALPHAMAB BIOPHARMACEUTICALS CO., LTD., Suzhou (CN)

( * ) Notice: Subject to any disclaimer, the term of this patent is extended or adjusted under 35 U.S.C. 154(b) by 1139 days.

This patent is subject to a terminal disclaimer.

(21) Appl. No.: 17/038,863

(22) Filed: Sep. 30, 2020

(65) Prior Publication Data

US 2021/0095031 A1    Apr. 1, 2021

Related U.S. Application Data

(63) Continuation of application No. PCT/CN2019/089980, filed on Jun. 4, 2019.

(30) Foreign Application Priority Data

Jun. 5, 2018   (WO) ............... PCT/CN2018/090012
May 14, 2019  (WO) ............... PCT/CN2019/086821

(51) Int. Cl.
*C07K 16/28*    (2006.01)
*A61K 39/395*   (2006.01)
*A61P 35/00*    (2006.01)
*A61K 39/00*    (2006.01)

(52) U.S. Cl.
CPC ...... *C07K 16/2818* (2013.01); *C07K 16/2827* (2013.01); *A61K 2039/505* (2013.01); *C07K 2317/52* (2013.01)

(58) Field of Classification Search
None
See application file for complete search history.

(56) References Cited

U.S. PATENT DOCUMENTS

| | | |
|---|---|---|
| 10,501,551 B2 | 12/2019 | Eckelman et al. |
| 11,091,549 B2 | 8/2021 | Xu et al. |
| 11,225,522 B2 | 1/2022 | Xu et al. |
| 11,529,425 B2 * | 12/2022 | Xu ................... C07K 16/2827 |
| 11,634,492 B2 | 4/2023 | Xu et al. |
| 2011/0129458 A1 | 6/2011 | Dolk et al. |
| 2014/0044738 A1 | 2/2014 | Langermann et al. |
| 2016/0177284 A1 | 6/2016 | Poma et al. |
| 2016/0200813 A1 | 7/2016 | Benatuil et al. |
| 2016/0222121 A1 | 8/2016 | Johnson et al. |
| 2016/0376347 A1 | 12/2016 | Saelens et al. |
| 2017/0015758 A1 | 1/2017 | Hammond et al. |
| 2017/0198050 A1 | 7/2017 | Eckelman et al. |
| 2017/0216433 A1 | 8/2017 | Li et al. |
| 2018/0000851 A1 | 1/2018 | Krieg |
| 2018/0022807 A1 | 1/2018 | Kasturirangan et al. |
| 2018/0037654 A1 | 2/2018 | Van Eenennaam et al. |
| 2018/0118836 A1 | 5/2018 | Bernett et al. |
| 2018/0162944 A1 | 6/2018 | Zheng et al. |
| 2018/0291103 A1 | 10/2018 | Xu et al. |
| 2018/0327494 A1 | 11/2018 | Xu et al. |
| 2018/0346571 A1 | 12/2018 | Gurney et al. |
| 2019/0119636 A1 | 4/2019 | Ostertag et al. |
| 2019/0127468 A1 | 5/2019 | Liu et al. |
| 2019/0169232 A1 | 6/2019 | Diamond |
| 2019/0185569 A1 | 6/2019 | Li et al. |
| 2019/0185570 A1 | 6/2019 | Keyt et al. |
| 2019/0202917 A1 | 7/2019 | Campbell et al. |
| 2019/0202935 A1 | 7/2019 | Chou et al. |
| 2019/0233519 A1 | 8/2019 | Zhang et al. |
| 2019/0315864 A1 | 10/2019 | Xu et al. |
| 2019/0352406 A1 | 11/2019 | Tavernier et al. |
| 2020/0308287 A1 | 10/2020 | Li et al. |
| 2021/0095031 A1 | 4/2021 | Xu et al. |
| 2021/0162061 A1 | 6/2021 | Xu et al. |
| 2021/0221891 A1 | 7/2021 | Zhang et al. |
| 2023/0015590 A1 * | 1/2023 | Xu .................. A61K 31/337 |

(Continued)

FOREIGN PATENT DOCUMENTS

| | | |
|---|---|---|
| CN | 105296433 A | 2/2016 |
| CN | 105754990 A | 7/2016 |
| CN | 106397592 A | 2/2017 |
| CN | 106967172 A | 7/2017 |
| CN | 107400166 A | 11/2017 |
| EP | 3 459 597 A1 | 3/2019 |
| WO | 2014/209804 A1 | 12/2014 |
| WO | WO 2017/020801 | 2/2017 |
| WO | WO 2017/123650 | 7/2017 |
| WO | 2018068201 A1 | 4/2018 |

OTHER PUBLICATIONS

Abdiche et al., "Assessing kinetic and epitopic diversity across orthogonal monoclonal antibody generation platforms," mAbs (2016) 8:264-277.

(Continued)

*Primary Examiner* — Ilia I Ouspenski

(74) *Attorney, Agent, or Firm* — Steptoe LLP; Z. Ying Li; Wyan-Ching M. Lee

(57) ABSTRACT

The present disclosure provides a dimer formed by two polypeptide chains, with each of the two polypeptide chains comprising an antibody Fc subunit, wherein the dimer comprises two or more immunoglobulin single variable domains (ISVDs), at least one of the ISVDs is specific for PD-L1, and at least one of the ISVDs is specific for CTLA4.

14 Claims, 15 Drawing Sheets

Specification includes a Sequence Listing.

(56) References Cited

U.S. PATENT DOCUMENTS

2023/0017515 A1* 1/2023 Xu .................. C07K 16/2818

OTHER PUBLICATIONS

Bannas et al., "Nanobodies and nanobody-based human heavy chain antibodies as antitumor therapeutics," Front. Immunol. (2017) 8:1603:1-13.

Boyd et al., "Deep sequencing and human antibody repertoire analysis," Current Opinion in Immunology 2016, 40:103-109.

Conroy et al., "From novel repertoires to defining and refining the structure of biologically important targets," Methods (2017) 116:12-22.

Coward et al., "Preliminary safety, efficacy, and pharmacokinetics (PK) results of KN046 (bispecific anti-PD-L1/CTLA4) from a first-in human study in subjects with advanced solid tumors," Journal of Clinical Oncology (2019) 37(S15):1-4.

Ferrara et al., "Recombinant renewable polyclonal antibodies," mAbs (2015) 7:32-41.

Khan et al., "Cross-neutralizing anti-HIV-1 human single chain variable fragments (scFvs) against CD4 binding site and N332 glycan identified from a recombinant phage library," Sci. Rep. (2017) 7:45163.

Könitzer et al., "Generation of a highly diverse panel of antagonistic chicken monoclonal antibodies against the GIP receptor," mAbs (2017) 9:536-549.

Lee et al., "Molecular-level analysis of the serum antibody repertoire in young adults before and after seasonal influenza vaccination," Nature Medicine (2016) 22:1456-1464.

Parola et al., "Integrating high-throughput screening and sequencing for monoclonal antibody discovery and engineering," Immunology (2018) 153:31-41.

Sheehan et al., "Phage and yeast display," Microbial. Spectr. (2015) 3(1):1-17.

Van Regenmortel et al., "Development of a preventive HIV vaccine requires solving inverse problems which is unattainable by rational vaccine design," Front. Immunol. (2018) 8:2009.

Zhang et al., "Structural basis of the therapeutic anti-PD-L1 antibody atezolizumab," Oncotarget (2017) 8(52):90215-90224.

Zhu et al., "Structural repertoire of HIV-1-neutralizing antibodies targeting the CD4 supersite in 14 donors," Cell (2015) 161:1280-1292.

* cited by examiner

E

◆ aPDL1.9-aCTLA4.34-Fc
○ aPDL1.9-aCTLA4.13-Fc

F

◆ aPDL1.9-aCTLA4.34-Fc
○ aPDL1.m3-aCTLA4.34-Fc
□ aPDL1.6-aCTLA4.34-Fc

E

○ aPDL1.9-aCTLA4.34-Fc
□ Ipilimumab
△ dAb-aCTLA4.34-Fc

F

○ aPDL1.9-aCTLA4.34-Fc
□ Ipilimumab
△ dAb-aCTLA4.34-Fc

E

F

SEQUENCE LISTING

```
<160> NUMBER OF SEQ ID NOS: 64

<210> SEQ ID NO 1
<211> LENGTH: 19
<212> TYPE: PRT
<213> ORGANISM: Artificial Sequence
<220> FEATURE:
```

```
<223> OTHER INFORMATION: CDR3 of antiPD-L1
<220> FEATURE:
<221> NAME/KEY: X
<222> LOCATION: (4)..(4)
<223> OTHER INFORMATION: X1=E/G
<220> FEATURE:
<221> NAME/KEY: X
<222> LOCATION: (5)..(5)
<223> OTHER INFORMATION: X=D/Y
<220> FEATURE:
<221> NAME/KEY: X
<222> LOCATION: (9)..(9)
<223> OTHER INFORMATION: ,X=T/P
<220> FEATURE:
<221> NAME/KEY: X
<222> LOCATION: (10)..(10)
<223> OTHER INFORMATION: ,X=L/G
<220> FEATURE:
<221> NAME/KEY: X
<222> LOCATION: (11)..(11)
<223> OTHER INFORMATION: ,X=V/P
<220> FEATURE:
<221> NAME/KEY: X
<222> LOCATION: (12)..(12)
<223> OTHER INFORMATION: X=T/A

<400> SEQUENCE: 1

Asp Ser Phe Xaa Xaa Pro Thr Cys Xaa Xaa Xaa Xaa Ser Ser Gly Ala
1               5                   10                  15

Phe Gln Tyr

<210> SEQ ID NO 2
<211> LENGTH: 10
<212> TYPE: PRT
<213> ORGANISM: Artificial Sequence
<220> FEATURE:
<223> OTHER INFORMATION: CDR1 of antiPD-L1
<220> FEATURE:
<221> NAME/KEY: X
<222> LOCATION: (2)..(2)
<223> OTHER INFORMATION: X=K/N
<220> FEATURE:
<221> NAME/KEY: X
<222> LOCATION: (3)..(3)
<223> OTHER INFORMATION: X=M/I
<220> FEATURE:
<221> NAME/KEY: X
<222> LOCATION: (4)..(4)
<223> OTHER INFORMATION: X=S/I
<220> FEATURE:
<221> NAME/KEY: X
<222> LOCATION: (5)..(5)
<223> OTHER INFORMATION: X=S/R
<220> FEATURE:
<221> NAME/KEY: X
<222> LOCATION: (6)..(6)
<223> OTHER INFORMATION: X=R/V

<400> SEQUENCE: 2

Gly Xaa Xaa Xaa Xaa Xaa Arg Cys Met Ala
1               5                   10

<210> SEQ ID NO 3
<211> LENGTH: 10
<212> TYPE: PRT
<213> ORGANISM: Artificial Sequence
<220> FEATURE:
<223> OTHER INFORMATION: PD-L1 ISVD-9 CDR1

<400> SEQUENCE: 3

Gly Lys Met Ser Ser Arg Arg Cys Met Ala
1               5                   10
```

<210> SEQ ID NO 4
<211> LENGTH: 17
<212> TYPE: PRT
<213> ORGANISM: Artificial Sequence
<220> FEATURE:
<223> OTHER INFORMATION: PD-L1 ISVD-9 CDR2

<400> SEQUENCE: 4

```
Lys Leu Leu Thr Thr Ser Gly Ser Thr Tyr Leu Ala Asp Ser Val Lys
1               5                   10                  15

Gly
```

<210> SEQ ID NO 5
<211> LENGTH: 19
<212> TYPE: PRT
<213> ORGANISM: Artificial Sequence
<220> FEATURE:
<223> OTHER INFORMATION: PD-L1 ISVD-9 CDR3

<400> SEQUENCE: 5

```
Asp Ser Phe Glu Asp Pro Thr Cys Thr Leu Val Thr Ser Ser Gly Ala
1               5                   10                  15

Phe Gln Tyr
```

<210> SEQ ID NO 6
<211> LENGTH: 128
<212> TYPE: PRT
<213> ORGANISM: Artificial Sequence
<220> FEATURE:
<223> OTHER INFORMATION: PD-L1 ISVD-9

<400> SEQUENCE: 6

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125
```

<210> SEQ ID NO 7
<211> LENGTH: 10
<212> TYPE: PRT
<213> ORGANISM: Artificial Sequence
<220> FEATURE:
<223> OTHER INFORMATION: PD-L1 ISVD-6 CDR1

<400> SEQUENCE: 7

```
Gly Asn Ile Ile Arg Val Arg Cys Met Ala
1               5                   10
```

<210> SEQ ID NO 8

```
<211> LENGTH: 17
<212> TYPE: PRT
<213> ORGANISM: Artificial Sequence
<220> FEATURE:
<223> OTHER INFORMATION: PD-L1 ISVD-6 CDR2

<400> SEQUENCE: 8

Asn Ile Leu Thr Thr Thr Ile Ser Thr Tyr Leu Ala Asp Ser Val Lys
1               5                   10                  15

Gly

<210> SEQ ID NO 9
<211> LENGTH: 19
<212> TYPE: PRT
<213> ORGANISM: Artificial Sequence
<220> FEATURE:
<223> OTHER INFORMATION: PD-L1 ISVD-6 CDR3

<400> SEQUENCE: 9

Asp Ser Phe Gly Tyr Pro Thr Cys Pro Gly Pro Ala Ser Ser Gly Ala
1               5                   10                  15

Phe Gln Tyr

<210> SEQ ID NO 10
<211> LENGTH: 128
<212> TYPE: PRT
<213> ORGANISM: Artificial Sequence
<220> FEATURE:
<223> OTHER INFORMATION: PD-L1 ISVD-6

<400> SEQUENCE: 10

Gln Val Gln Leu Gln Glu Ser Gly Gly Gly Ser Val Gln Ala Gly Gly
1               5                   10                  15

Ser Leu Arg Leu Ser Cys Ala Ala Ser Gly Asn Ile Ile Arg Val Arg
            20                  25                  30

Cys Met Ala Trp Phe Arg Gln Ala Pro Gly Lys Glu Arg Glu Arg Gly
        35                  40                  45

Pro Asn Ile Leu Thr Thr Thr Ile Ser Thr Tyr Leu Ala Asp Ser Val
    50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Gly Tyr Pro Thr Cys Pro Gly Pro Ala Ser Ser
            100                 105                 110

Gly Ala Phe Gln Tyr Trp Gly Gln Gly Thr Gln Val Thr Val Ser Ser
        115                 120                 125

<210> SEQ ID NO 11
<211> LENGTH: 17
<212> TYPE: PRT
<213> ORGANISM: Artificial Sequence
<220> FEATURE:
<223> OTHER INFORMATION: PD-L1 ISVD-m3 CDR2

<400> SEQUENCE: 11

Asp Val Asn Pro Asn Ser Gly Gly Ser Ile Tyr Asn Gln Arg Phe Lys
1               5                   10                  15

Gly

<210> SEQ ID NO 12
```

```
<211> LENGTH: 128
<212> TYPE: PRT
<213> ORGANISM: Artificial Sequence
<220> FEATURE:
<223> OTHER INFORMATION: PD-L1 ISVD-m3

<400> SEQUENCE: 12

Gln Val Gln Leu Gln Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Asp Val Asn Pro Asn Ser Gly Gly Ser Ile Tyr Asn Gln Arg Phe
    50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Gln Val Thr Val Ser Ser
        115                 120                 125

<210> SEQ ID NO 13
<211> LENGTH: 128
<212> TYPE: PRT
<213> ORGANISM: Artificial Sequence
<220> FEATURE:
<223> OTHER INFORMATION: PD-L1 ISVD-4

<400> SEQUENCE: 13

Gln Val Gln Leu Gln Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Gln Val Thr Val Ser Ser
        115                 120                 125

<210> SEQ ID NO 14
<211> LENGTH: 128
<212> TYPE: PRT
<213> ORGANISM: Artificial Sequence
<220> FEATURE:
<223> OTHER INFORMATION: PD-L1 ISVD-11

<400> SEQUENCE: 14

Gln Val Gln Leu Val Glu Ser Gly Gly Gly Leu Val Gln Pro Gly Gly
1               5                   10                  15
```

```
Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Gly Leu Glu Arg Val
            35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
            115                 120                 125
```

<210> SEQ ID NO 15
<211> LENGTH: 128
<212> TYPE: PRT
<213> ORGANISM: Artificial Sequence
<220> FEATURE:
<223> OTHER INFORMATION: PD-L1 ISVD-13

<400> SEQUENCE: 15

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
            35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Lys Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
            115                 120                 125
```

<210> SEQ ID NO 16
<211> LENGTH: 17
<212> TYPE: PRT
<213> ORGANISM: Artificial Sequence
<220> FEATURE:
<223> OTHER INFORMATION: CDR2 of CTLA4
<220> FEATURE:
<221> NAME/KEY: X
<222> LOCATION: (3)..(3)
<223> OTHER INFORMATION: X=Y/S
<220> FEATURE:
<221> NAME/KEY: X
<222> LOCATION: (4)..(4)
<223> OTHER INFORMATION: X=I/L

<400> SEQUENCE: 16

```
Ala Ile Xaa Xaa Gly Gly Gly Ser Thr Tyr Tyr Ala Asp Ser Val Lys
1               5                   10                  15

Gly
```

```
<210> SEQ ID NO 17
<211> LENGTH: 5
<212> TYPE: PRT
<213> ORGANISM: Artificial Sequence
<220> FEATURE:
<223> OTHER INFORMATION: CTLA4 ISVD-34 CDR1

<400> SEQUENCE: 17

Ala Tyr Cys Met Gly
1               5

<210> SEQ ID NO 18
<211> LENGTH: 17
<212> TYPE: PRT
<213> ORGANISM: Artificial Sequence
<220> FEATURE:
<223> OTHER INFORMATION: CTLA4 ISVD-34 CDR2

<400> SEQUENCE: 18

Ala Ile Tyr Ile Gly Gly Gly Ser Thr Tyr Tyr Ala Asp Ser Val Lys
1               5                   10                  15

Gly

<210> SEQ ID NO 19
<211> LENGTH: 19
<212> TYPE: PRT
<213> ORGANISM: Artificial Sequence
<220> FEATURE:
<223> OTHER INFORMATION: CTLA4 ISVD-34 CDR3

<400> SEQUENCE: 19

Asp Val Ile Pro Thr Glu Thr Cys Leu Gly Gly Ser Trp Ser Gly Pro
1               5                   10                  15

Phe Gly Tyr

<210> SEQ ID NO 20
<211> LENGTH: 128
<212> TYPE: PRT
<213> ORGANISM: Artificial Sequence
<220> FEATURE:
<223> OTHER INFORMATION: CTLA4 ISVD-34

<400> SEQUENCE: 20

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
                20                  25                  30

Cys Met Gly Trp Phe Arg Gln Ala Pro Gly Lys Gly Leu Glu Gly Val
            35                  40                  45

Ala Ala Ile Tyr Ile Gly Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

<210> SEQ ID NO 21
<211> LENGTH: 17
```

```
<212> TYPE: PRT
<213> ORGANISM: Artificial Sequence
<220> FEATURE:
<223> OTHER INFORMATION: CTLA4 ISVD-C1 CDR2

<400> SEQUENCE: 21

Ala Ile Tyr Leu Gly Gly Gly Ser Thr Tyr Tyr Ala Asp Ser Val Lys
1               5                   10                  15

Gly

<210> SEQ ID NO 22
<211> LENGTH: 128
<212> TYPE: PRT
<213> ORGANISM: Artificial Sequence
<220> FEATURE:
<223> OTHER INFORMATION: CTLA4 ISVD-C1

<400> SEQUENCE: 22

Gln Val Gln Leu Gln Glu Ser Gly Gly Gly Ser Val Gln Ala Gly Gly
1               5                   10                  15

Ser Leu Gly Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Glu Gly Val
        35                  40                  45

Ala Ala Ile Tyr Leu Gly Gly Gly Ser Thr Tyr Tyr Ala Asp Ser Val
    50                  55                  60

Lys Gly Arg Phe Thr Ile Ser Gln Asp Ile Ala Lys Asn Thr Leu Tyr
65                  70                  75                  80

Leu Gln Met Asn Ser Leu Lys Pro Glu Asp Thr Ala Met Tyr Ser Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Gln Val Thr Val Ser Ser
        115                 120                 125

<210> SEQ ID NO 23
<211> LENGTH: 17
<212> TYPE: PRT
<213> ORGANISM: Artificial Sequence
<220> FEATURE:
<223> OTHER INFORMATION: CTLA4 ISVD-13 CDR2

<400> SEQUENCE: 23

Ala Ile Ser Ile Gly Gly Gly Ser Thr Tyr Tyr Ala Asp Ser Val Lys
1               5                   10                  15

Gly

<210> SEQ ID NO 24
<211> LENGTH: 128
<212> TYPE: PRT
<213> ORGANISM: Artificial Sequence
<220> FEATURE:
<223> OTHER INFORMATION: CTLA4 ISVD-13

<400> SEQUENCE: 24

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Val Gly Val
        35                  40                  45
```

```
Ala Ala Ile Ser Ile Gly Gly Gly Ser Thr Tyr Tyr Ala Asp Ser Val
            50                  55                  60

Lys Gly Arg Phe Thr Ile Ser Gln Asp Asn Ala Lys Asn Thr Leu Tyr
 65                  70                  75                  80

Leu Gln Met Asn Ser Leu Lys Pro Glu Asp Thr Ala Met Tyr Tyr Cys
                 85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Gln Val Thr Val Ser Ser
            115                 120                 125

<210> SEQ ID NO 25
<211> LENGTH: 128
<212> TYPE: PRT
<213> ORGANISM: Artificial Sequence
<220> FEATURE:
<223> OTHER INFORMATION: CTLA4 ISVD-26

<400> SEQUENCE: 25

Gln Val Gln Leu Val Glu Ser Gly Gly Gly Leu Val Gln Pro Gly Gly
 1                5                  10                  15

Ser Leu Arg Leu Ser Cys Ala Ala Ser Gly Tyr Ile Tyr Ser Ala Tyr
             20                  25                  30

Cys Met Gly Trp Phe Arg Gln Ala Pro Gly Lys Glu Arg Val Gly Val
             35                  40                  45

Ala Ala Ile Ser Ile Gly Gly Gly Ser Thr Tyr Tyr Ala Asp Ser Val
            50                  55                  60

Lys Gly Arg Phe Thr Ile Ser Gln Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
            115                 120                 125

<210> SEQ ID NO 26
<211> LENGTH: 128
<212> TYPE: PRT
<213> ORGANISM: Artificial Sequence
<220> FEATURE:
<223> OTHER INFORMATION: CTLA4 ISVD-27

<400> SEQUENCE: 26

Gln Val Gln Leu Val Glu Ser Gly Gly Gly Leu Val Gln Pro Gly Gly
 1                5                  10                  15

Ser Leu Arg Leu Ser Cys Ala Ala Ser Gly Tyr Ile Tyr Ser Ala Tyr
             20                  25                  30

Cys Met Gly Trp Phe Arg Gln Ala Pro Gly Lys Glu Arg Val Gly Val
             35                  40                  45

Ala Ala Ile Ser Ile Gly Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ala Asp Val Ile Pro Thr Glu Thr Cys Leu Gly Gly Ser Trp Ser
```

```
                  100                 105                 110

Gly Pro Phe Gly Tyr Trp Gly Gln Gly Thr Leu Val Thr Val Ser Ser
            115                 120                 125

<210> SEQ ID NO 27
<211> LENGTH: 128
<212> TYPE: PRT
<213> ORGANISM: Artificial Sequence
<220> FEATURE:
<223> OTHER INFORMATION: CTLA4 ISVD-28

<400> SEQUENCE: 27

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Gly Leu Val Gly Val
        35                  40                  45

Ala Ala Ile Ser Ile Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
            115                 120                 125

<210> SEQ ID NO 28
<211> LENGTH: 128
<212> TYPE: PRT
<213> ORGANISM: Artificial Sequence
<220> FEATURE:
<223> OTHER INFORMATION: CTLA4 ISVD-29

<400> SEQUENCE: 28

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Gly Leu Glu Gly Val
        35                  40                  45

Ala Ala Ile Ser Ile Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
            115                 120                 125

<210> SEQ ID NO 29
<211> LENGTH: 128
<212> TYPE: PRT
<213> ORGANISM: Artificial Sequence
<220> FEATURE:
```

<223> OTHER INFORMATION: CTLA4 ISVD-30

<400> SEQUENCE: 29

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Glu Gly Val
        35                  40                  45

Ala Ala Ile Ser Ile Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

<210> SEQ ID NO 30
<211> LENGTH: 128
<212> TYPE: PRT
<213> ORGANISM: Artificial Sequence
<220> FEATURE:
<223> OTHER INFORMATION: CTLA4 ISVD-31

<400> SEQUENCE: 30

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Glu Gly Val
        35                  40                  45

Ala Ala Ile Tyr Ile Gly Gly Ser Thr Tyr Tyr Ala Asp Ser Val
    50                  55                  60

Lys Gly Arg Phe Thr Ile Ser Gln Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

<210> SEQ ID NO 31
<211> LENGTH: 128
<212> TYPE: PRT
<213> ORGANISM: Artificial Sequence
<220> FEATURE:
<223> OTHER INFORMATION: CTLA4 ISVD-32

<400> SEQUENCE: 31

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Glu Gly Val

```
                35                  40                  45
Ala Ala Ile Tyr Ile Gly Gly Ser Thr Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Ala Asp Val Ile Pro Thr Glu Thr Cys Leu Gly Gly Ser Trp Ser
                100                 105                 110
Gly Pro Phe Gly Tyr Trp Gly Gln Gly Thr Leu Val Thr Val Ser Ser
        115                 120                 125

<210> SEQ ID NO 32
<211> LENGTH: 128
<212> TYPE: PRT
<213> ORGANISM: Artificial Sequence
<220> FEATURE:
<223> OTHER INFORMATION: CTLA4 ISVD-33

<400> SEQUENCE: 32

Gln Val Gln Leu Val Glu Ser Gly Gly Gly Leu Val Gln Pro Gly Gly
1               5                   10                  15
Ser Leu Arg Leu Ser Cys Ala Ala Ser Gly Tyr Ile Tyr Ser Ala Tyr
            20                  25                  30
Cys Met Gly Trp Phe Arg Gln Ala Pro Gly Lys Gly Leu Val Gly Val
        35                  40                  45
Ala Ala Ile Tyr Ile Gly Gly Ser Thr Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Ala Asp Val Ile Pro Thr Glu Thr Cys Leu Gly Gly Ser Trp Ser
                100                 105                 110
Gly Pro Phe Gly Tyr Trp Gly Gln Gly Thr Leu Val Thr Val Ser Ser
        115                 120                 125

<210> SEQ ID NO 33
<211> LENGTH: 3
<212> TYPE: PRT
<213> ORGANISM: Artificial Sequence
<220> FEATURE:
<223> OTHER INFORMATION: short linker

<400> SEQUENCE: 33

Gly Ala Pro
1

<210> SEQ ID NO 34
<211> LENGTH: 15
<212> TYPE: PRT
<213> ORGANISM: Artificial Sequence
<220> FEATURE:
<223> OTHER INFORMATION: long linker

<400> SEQUENCE: 34

Gly Gly Gly Gly Ser Gly Gly Gly Gly Ser Gly Gly Gly Gly Ser
1               5                   10                  15

<210> SEQ ID NO 35
```

<211> LENGTH: 232
<212> TYPE: PRT
<213> ORGANISM: Artificial Sequence
<220> FEATURE:
<223> OTHER INFORMATION: IgG1-Fc region with hinge

<400> SEQUENCE: 35

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 36
<211> LENGTH: 330
<212> TYPE: PRT
<213> ORGANISM: Artificial Sequence
<220> FEATURE:
<223> OTHER INFORMATION: human IgG1 constant region

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys

```
            85                  90                  95
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 37
<211> LENGTH: 124
<212> TYPE: PRT
<213> ORGANISM: Artificial Sequence
<220> FEATURE:
<223> OTHER INFORMATION: control dAb

<400> SEQUENCE: 37

Gln Val Gln Leu Gln Glu Ser Gly Gly Gly Ser Val Gln Ala Gly Gly
1               5                   10                  15

Ser Leu Arg Leu Ser Cys Glu Ala Ser Gly Tyr Thr Tyr Cys Met Gly
            20                  25                  30

Trp Phe Arg Gln Ala Pro Gly Lys Glu Arg Glu Gly Val Ala Leu Ala
            35                  40                  45

Val Thr Gly Ile Ser Ile Pro Tyr Tyr Ala Asp Ser Val Lys Gly Arg
            50                  55                  60

Phe Thr Ile Ser Gln Asp Asn Val Lys Asn Thr Leu Tyr Leu Gln Met
65                  70                  75                  80

Asn Ser Leu Lys Pro Glu Asp Ala Ala Met Tyr Tyr Cys Ala Ala Ser
            85                  90                  95

Thr Ile Arg Tyr Val Cys Pro Gly Leu Asn Arg Gly Asp Gln Phe Lys
            100                 105                 110

Asn Trp Gly Gln Gly Thr Gln Val Thr Val Ser Ser
```

```
                       115                 120

<210> SEQ ID NO 38
<211> LENGTH: 232
<212> TYPE: PRT
<213> ORGANISM: Artificial Sequence
<220> FEATURE:
<223> OTHER INFORMATION: IgG1-Fc region with hinge (C-S)

<400> SEQUENCE: 38

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 39
<211> LENGTH: 227
<212> TYPE: PRT
<213> ORGANISM: Artificial Sequence
<220> FEATURE:
<223> OTHER INFORMATION: human IgG1-Fc region without hinge

<400> SEQUENCE: 39

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60
```

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 40
<211> LENGTH: 493
<212> TYPE: PRT
<213> ORGANISM: Artificial Sequence
<220> FEATURE:
<223> OTHER INFORMATION: aPDL1.9-aCTLA4.34-Fc

<400> SEQUENCE: 40

Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

Gly Ala Pro Gln Val Gln Leu Val Glu Ser Gly Gly Gly Leu Val Gln
    130                 135                 140

Pro Gly Gly Ser Leu Arg Leu Ser Cys Ala Ala Ser Gly Tyr Ile Tyr
145                 150                 155                 160

Ser Ala Tyr Cys Met Gly Trp Phe Arg Gln Ala Pro Gly Lys Gly Leu
                165                 170                 175

Glu Gly Val Ala Ala Ile Tyr Ile Gly Gly Ser Thr Tyr Tyr Ala
            180                 185                 190

Asp Ser Val Lys Gly Arg Phe Thr Ile Ser Arg Asp Asn Ser Lys Asn
            195                 200                 205

Thr Leu Tyr Leu Gln Met Asn Ser Leu Arg Ala Glu Asp Thr Ala Val
    210                 215                 220

Tyr Tyr Cys Ala Ala Asp Val Ile Pro Thr Glu Thr Cys Leu Gly Gly
225                 230                 235                 240

Ser Trp Ser Gly Pro Phe Gly Tyr Trp Gly Gln Gly Thr Leu Val Thr
                245                 250                 255

Val Ser Ser Gly Ser Glu Pro Lys Ser Ser Asp Lys Thr His Thr Cys
            260                 265                 270

Pro Pro Cys Pro Ala Pro Glu Leu Leu Gly Gly Pro Ser Val Phe Leu
    275                 280                 285

Phe Pro Pro Lys Pro Lys Asp Thr Leu Met Ile Ser Arg Thr Pro Glu
290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
    355                 360                 365

Val Ser Asn Lys Ala Leu Pro Ala Pro Ile Glu Lys Thr Ile Ser Lys
370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
    435                 440                 445

Ser Phe Phe Leu Tyr Ser Lys Leu Thr Val Asp Lys Ser Arg Trp Gln
450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 41
<211> LENGTH: 505
<212> TYPE: PRT
<213> ORGANISM: Artificial Sequence
<220> FEATURE:
<223> OTHER INFORMATION: aPDL1.9-L-aCTLA4.34-Fc

<400> SEQUENCE: 41

Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

```
Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

Gly Gly Gly Gly Ser Gly Gly Gly Ser Gly Gly Gly Gly Ser Gln
130                 135                 140

Val Gln Leu Val Glu Ser Gly Gly Gly Leu Val Gln Pro Gly Gly Ser
145                 150                 155                 160

Leu Arg Leu Ser Cys Ala Ala Ser Gly Tyr Ile Tyr Ser Ala Tyr Cys
                165                 170                 175

Met Gly Trp Phe Arg Gln Ala Pro Gly Lys Gly Leu Glu Gly Val Ala
            180                 185                 190

Ala Ile Tyr Ile Gly Gly Ser Thr Tyr Tyr Ala Asp Ser Val Lys
        195                 200                 205

Gly Arg Phe Thr Ile Ser Arg Asp Asn Ser Lys Asn Thr Leu Tyr Leu
210                 215                 220

Gln Met Asn Ser Leu Arg Ala Glu Asp Thr Ala Val Tyr Tyr Cys Ala
225                 230                 235                 240

Ala Asp Val Ile Pro Thr Glu Thr Cys Leu Gly Gly Ser Trp Ser Gly
                245                 250                 255

Pro Phe Gly Tyr Trp Gly Gln Gly Thr Leu Val Thr Val Ser Ser Gly
            260                 265                 270

Ser Glu Pro Lys Ser Ser Asp Lys Thr His Thr Cys Pro Pro Cys Pro
        275                 280                 285

Ala Pro Glu Leu Leu Gly Gly Pro Ser Val Phe Leu Phe Pro Pro Lys
290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
        355                 360                 365

Gln Asp Trp Leu Asn Gly Lys Glu Tyr Lys Cys Lys Val Ser Asn Lys
        370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Asp Glu Leu
                405                 410                 415

Thr Lys Asn Gln Val Ser Leu Thr Cys Leu Val Lys Gly Phe Tyr Pro
            420                 425                 430

Ser Asp Ile Ala Val Glu Trp Glu Ser Asn Gly Gln Pro Glu Asn Asn
        435                 440                 445

Tyr Lys Thr Thr Pro Pro Val Leu Asp Ser Asp Gly Ser Phe Phe Leu
        450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
```

```
                    485                 490                 495

Lys Ser Leu Ser Leu Ser Pro Gly Lys
            500                 505

<210> SEQ ID NO 42
<211> LENGTH: 493
<212> TYPE: PRT
<213> ORGANISM: Artificial Sequence
<220> FEATURE:
<223> OTHER INFORMATION: aCTLA4.34-aPDL1.9-Fc

<400> SEQUENCE: 42

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Gly Leu Glu Gly Val
        35                  40                  45

Ala Ala Ile Tyr Ile Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

Gly Ala Pro Gln Val Gln Leu Val Glu Ser Gly Gly Gly Leu Val Gln
    130                 135                 140

Pro Gly Gly Ser Leu Arg Leu Ser Cys Ala Ala Ser Gly Lys Met Ser
145                 150                 155                 160

Ser Arg Arg Cys Met Ala Trp Phe Arg Gln Ala Pro Gly Lys Glu Arg
                165                 170                 175

Glu Arg Val Ala Lys Leu Leu Thr Thr Ser Gly Ser Thr Tyr Leu Ala
            180                 185                 190

Asp Ser Val Lys Gly Arg Phe Thr Ile Ser Arg Asp Asn Ser Lys Asn
        195                 200                 205

Thr Val Tyr Leu Gln Met Asn Ser Leu Arg Ala Glu Asp Thr Ala Val
    210                 215                 220

Tyr Tyr Cys Ala Ala Asp Ser Phe Glu Asp Pro Thr Cys Thr Leu Val
225                 230                 235                 240

Thr Ser Ser Gly Ala Phe Gln Tyr Trp Gly Gln Gly Thr Leu Val Thr
                245                 250                 255

Val Ser Ser Gly Ser Glu Pro Lys Ser Ser Asp Lys Thr His Thr Cys
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
```

```
            340                 345                 350
Thr Val Leu His Gln Asp Trp Leu Asn Gly Lys Glu Tyr Lys Cys Lys
                355                 360                 365

Val Ser Asn Lys Ala Leu Pro Ala Pro Ile Glu Lys Thr Ile Ser Lys
        370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
                420                 425                 430

Pro Glu Asn Asn Tyr Lys Thr Thr Pro Pro Val Leu Asp Ser Asp Gly
                435                 440                 445

Ser Phe Phe Leu Tyr Ser Lys Leu Thr Val Asp Lys Ser Arg Trp Gln
        450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 43
<211> LENGTH: 505
<212> TYPE: PRT
<213> ORGANISM: Artificial Sequence
<220> FEATURE:
<223> OTHER INFORMATION: aCTLA4.34-L-aPDL1.9-FC

<400> SEQUENCE: 43

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
                20                  25                  30

Cys Met Gly Trp Phe Arg Gln Ala Pro Gly Lys Gly Leu Glu Gly Val
            35                  40                  45

Ala Ala Ile Tyr Ile Gly Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

Gly Gly Gly Gly Ser Gly Gly Gly Ser Gly Gly Gly Gly Ser Gln
        130                 135                 140

Val Gln Leu Val Glu Ser Gly Gly Gly Leu Val Gln Pro Gly Gly Ser
145                 150                 155                 160

Leu Arg Leu Ser Cys Ala Ala Ser Gly Lys Met Ser Ser Arg Arg Cys
                165                 170                 175

Met Ala Trp Phe Arg Gln Ala Pro Gly Lys Glu Arg Glu Arg Val Ala
            180                 185                 190

Lys Leu Leu Thr Thr Ser Gly Ser Thr Tyr Leu Ala Asp Ser Val Lys
        195                 200                 205

Gly Arg Phe Thr Ile Ser Arg Asp Asn Ser Lys Asn Thr Val Tyr Leu
```

```
                210                 215                 220
Gln Met Asn Ser Leu Arg Ala Glu Asp Thr Ala Val Tyr Tyr Cys Ala
225                 230                 235                 240

Ala Asp Ser Phe Glu Asp Pro Thr Cys Thr Leu Val Thr Ser Ser Gly
                245                 250                 255

Ala Phe Gln Tyr Trp Gly Gln Gly Thr Leu Val Thr Val Ser Ser Gly
                260                 265                 270

Ser Glu Pro Lys Ser Ser Asp Lys Thr His Thr Cys Pro Pro Cys Pro
                275                 280                 285

Ala Pro Glu Leu Leu Gly Gly Pro Ser Val Phe Leu Phe Pro Pro Lys
290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
                340                 345                 350

Gln Tyr Asn Ser Thr Tyr Arg Val Val Ser Val Leu Thr Val Leu His
                355                 360                 365

Gln Asp Trp Leu Asn Gly Lys Glu Tyr Lys Cys Lys Val Ser Asn Lys
370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Asp Glu Leu
                405                 410                 415

Thr Lys Asn Gln Val Ser Leu Thr Cys Leu Val Lys Gly Phe Tyr Pro
                420                 425                 430

Ser Asp Ile Ala Val Glu Trp Glu Ser Asn Gly Gln Pro Glu Asn Asn
                435                 440                 445

Tyr Lys Thr Thr Pro Pro Val Leu Asp Ser Asp Gly Ser Phe Phe Leu
450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
                485                 490                 495

Lys Ser Leu Ser Leu Ser Pro Gly Lys
                500                 505

<210> SEQ ID NO 44
<211> LENGTH: 487
<212> TYPE: PRT
<213> ORGANISM: Artificial Sequence
<220> FEATURE:
<223> OTHER INFORMATION: aPDL1.9-dAb-Fc

<400> SEQUENCE: 44

Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
                20                  25                  30

Cys Met Ala Trp Phe Arg Gln Ala Pro Gly Lys Glu Arg Glu Arg Val
                35                  40                  45

Ala Lys Leu Leu Thr Thr Ser Gly Ser Thr Tyr Leu Ala Asp Ser Val
                50                  55                  60

Lys Gly Arg Phe Thr Ile Ser Arg Asp Asn Ser Lys Asn Thr Val Tyr
```

```
                65                  70                  75                  80
Leu Gln Met Asn Ser Leu Arg Ala Glu Asp Thr Ala Val Tyr Tyr Cys
                        85                  90                  95
Ala Ala Asp Ser Phe Glu Asp Pro Thr Cys Thr Leu Val Thr Ser Ser
                        100                 105                 110
Gly Ala Phe Gln Tyr Trp Gly Gln Gly Thr Leu Val Thr Val Ser Ser
                        115                 120                 125
Gly Ala Pro Gln Val Gln Leu Gln Glu Ser Gly Gly Gly Ser Val Gln
        130                 135                 140
Ala Gly Gly Ser Leu Arg Leu Ser Cys Glu Ala Ser Gly Tyr Thr Tyr
145                 150                 155                 160
Cys Met Gly Trp Phe Arg Gln Ala Pro Gly Lys Glu Arg Glu Gly Val
                        165                 170                 175
Ala Leu Ala Val Thr Gly Ile Ser Ile Pro Tyr Tyr Ala Asp Ser Val
                        180                 185                 190
Lys Gly Arg Phe Thr Ile Ser Gln Asp Asn Val Lys Asn Thr Leu Tyr
                        195                 200                 205
Leu Gln Met Asn Ser Leu Lys Pro Glu Asp Ala Ala Met Tyr Tyr Cys
        210                 215                 220
Ala Ala Ser Thr Ile Arg Tyr Val Cys Pro Gly Leu Asn Arg Gly Asp
225                 230                 235                 240
Gln Phe Lys Asn Trp Gly Gln Gly Thr Gln Val Thr Val Ser Ser Glu
                        245                 250                 255
Pro Lys Ser Ser Asp Lys Thr His Thr Cys Pro Pro Cys Pro Ala Pro
                        260                 265                 270
Glu Leu Leu Gly Gly Pro Ser Val Phe Leu Phe Pro Pro Lys Pro Lys
                        275                 280                 285
Asp Thr Leu Met Ile Ser Arg Thr Pro Glu Val Thr Cys Val Val Val
        290                 295                 300
Asp Val Ser His Glu Asp Pro Glu Val Lys Phe Asn Trp Tyr Val Asp
305                 310                 315                 320
Gly Val Glu Val His Asn Ala Lys Thr Lys Pro Arg Glu Glu Gln Tyr
                        325                 330                 335
Asn Ser Thr Tyr Arg Val Val Ser Val Leu Thr Val Leu His Gln Asp
                        340                 345                 350
Trp Leu Asn Gly Lys Glu Tyr Lys Cys Lys Val Ser Asn Lys Ala Leu
                        355                 360                 365
Pro Ala Pro Ile Glu Lys Thr Ile Ser Lys Ala Lys Gly Gln Pro Arg
        370                 375                 380
Glu Pro Gln Val Tyr Thr Leu Pro Pro Ser Arg Asp Glu Leu Thr Lys
385                 390                 395                 400
Asn Gln Val Ser Leu Thr Cys Leu Val Lys Gly Phe Tyr Pro Ser Asp
                        405                 410                 415
Ile Ala Val Glu Trp Glu Ser Asn Gly Gln Pro Glu Asn Asn Tyr Lys
                        420                 425                 430
Thr Thr Pro Pro Val Leu Asp Ser Asp Gly Ser Phe Phe Leu Tyr Ser
                        435                 440                 445
Lys Leu Thr Val Asp Lys Ser Arg Trp Gln Gln Gly Asn Val Phe Ser
                        450                 455                 460
Cys Ser Val Met His Glu Ala Leu His Asn His Tyr Thr Gln Lys Ser
465                 470                 475                 480
Leu Ser Leu Ser Pro Gly Lys
                        485
```

<210> SEQ ID NO 45
<211> LENGTH: 487
<212> TYPE: PRT
<213> ORGANISM: Artificial Sequence
<220> FEATURE:
<223> OTHER INFORMATION: dAb-aCTLA4.34-Fc

<400> SEQUENCE: 45

Gln Val Gln Leu Gln Glu Ser Gly Gly Gly Ser Val Gln Ala Gly Gly
1               5                   10                  15

Ser Leu Arg Leu Ser Cys Glu Ala Ser Gly Tyr Thr Tyr Cys Met Gly
            20                  25                  30

Trp Phe Arg Gln Ala Pro Gly Lys Glu Arg Glu Gly Val Ala Leu Ala
        35                  40                  45

Val Thr Gly Ile Ser Ile Pro Tyr Tyr Ala Asp Ser Val Lys Gly Arg
    50                  55                  60

Phe Thr Ile Ser Gln Asp Asn Val Lys Asn Thr Leu Tyr Leu Gln Met
65                  70                  75                  80

Asn Ser Leu Lys Pro Glu Asp Ala Ala Met Tyr Tyr Cys Ala Ala Ser
                85                  90                  95

Thr Ile Arg Tyr Val Cys Pro Gly Leu Asn Arg Gly Asp Gln Phe Lys
            100                 105                 110

Asn Trp Gly Gln Gly Thr Gln Val Thr Val Ser Ser Gly Ala Pro Gln
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Tyr Ile Tyr Ser Ala Tyr Cys
145                 150                 155                 160

Met Gly Trp Phe Arg Gln Ala Pro Gly Lys Gly Leu Glu Gly Val Ala
                165                 170                 175

Ala Ile Tyr Ile Gly Gly Gly Ser Thr Tyr Tyr Ala Asp Ser Val Lys
            180                 185                 190

Gly Arg Phe Thr Ile Ser Arg Asp Asn Ser Lys Asn Thr Leu Tyr Leu
        195                 200                 205

Gln Met Asn Ser Leu Arg Ala Glu Asp Thr Ala Val Tyr Tyr Cys Ala
    210                 215                 220

Ala Asp Val Ile Pro Thr Glu Thr Cys Leu Gly Gly Ser Trp Ser Gly
225                 230                 235                 240

Pro Phe Gly Tyr Trp Gly Gln Gly Thr Leu Val Thr Val Ser Ser Glu
                245                 250                 255

Pro Lys Ser Ser Asp Lys Thr His Thr Cys Pro Pro Cys Pro Ala Pro
            260                 265                 270

Glu Leu Leu Gly Gly Pro Ser Val Phe Leu Phe Pro Pro Lys Pro Lys
        275                 280                 285

Asp Thr Leu Met Ile Ser Arg Thr Pro Glu Val Thr Cys Val Val Val
    290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Ala Leu
        355                 360                 365

```
Pro Ala Pro Ile Glu Lys Thr Ile Ser Lys Ala Lys Gly Gln Pro Arg
        370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
                420                 425                 430

Thr Thr Pro Pro Val Leu Asp Ser Asp Gly Ser Phe Phe Leu Tyr Ser
            435                 440                 445

Lys Leu Thr Val Asp Lys Ser Arg Trp Gln Gln Gly Asn Val Phe Ser
        450                 455                 460

Cys Ser Val Met His Glu Ala Leu His Asn His Tyr Thr Gln Lys Ser
465                 470                 475                 480

Leu Ser Leu Ser Pro Gly Lys
                485

<210> SEQ ID NO 46
<211> LENGTH: 491
<212> TYPE: PRT
<213> ORGANISM: Artificial Sequence
<220> FEATURE:
<223> OTHER INFORMATION: aPDL1.6-aCTLA4.34-Fc

<400> SEQUENCE: 46

Gln Val Gln Leu Gln Glu Ser Gly Gly Gly Ser Val Gln Ala Gly Gly
1               5                   10                  15

Ser Leu Arg Leu Ser Cys Ala Ala Ser Gly Asn Ile Ile Arg Val Arg
            20                  25                  30

Cys Met Ala Trp Phe Arg Gln Ala Pro Gly Lys Glu Arg Glu Arg Gly
        35                  40                  45

Pro Asn Ile Leu Thr Thr Thr Ile Ser Thr Tyr Leu Ala Asp Ser Val
    50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Gly Tyr Pro Thr Cys Pro Gly Pro Ala Ser Ser
            100                 105                 110

Gly Ala Phe Gln Tyr Trp Gly Gln Gly Thr Gln Val Thr Val Ser Ser
        115                 120                 125

Gly Ala Pro Gln Val Gln Leu Val Glu Ser Gly Gly Gly Leu Val Gln
    130                 135                 140

Pro Gly Gly Ser Leu Arg Leu Ser Cys Ala Ala Ser Gly Tyr Ile Tyr
145                 150                 155                 160

Ser Ala Tyr Cys Met Gly Trp Phe Arg Gln Ala Pro Gly Lys Gly Leu
                165                 170                 175

Glu Gly Val Ala Ala Ile Tyr Ile Gly Gly Gly Ser Thr Tyr Tyr Ala
            180                 185                 190

Asp Ser Val Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
    210                 215                 220

Tyr Tyr Cys Ala Ala Asp Val Ile Pro Thr Glu Thr Cys Leu Gly Gly
225                 230                 235                 240
```

```
Ser Trp Ser Gly Pro Phe Gly Tyr Trp Gly Gln Gly Thr Leu Val Thr
                245                 250                 255

Val Ser Ser Glu Pro Lys Ser Ser Asp Lys Thr His Thr Cys Pro Pro
        260                 265                 270

Cys Pro Ala Pro Glu Leu Leu Gly Gly Pro Ser Val Phe Leu Phe Pro
            275                 280                 285

Pro Lys Pro Lys Asp Thr Leu Met Ile Ser Arg Thr Pro Glu Val Thr
290                 295                 300

Cys Val Val Val Asp Val Ser His Glu Asp Pro Glu Val Lys Phe Asn
305                 310                 315                 320

Trp Tyr Val Asp Gly Val Glu Val His Asn Ala Lys Thr Lys Pro Arg
                325                 330                 335

Glu Glu Gln Tyr Asn Ser Thr Tyr Arg Val Val Ser Val Leu Thr Val
                340                 345                 350

Leu His Gln Asp Trp Leu Asn Gly Lys Glu Tyr Lys Cys Lys Val Ser
            355                 360                 365

Asn Lys Ala Leu Pro Ala Pro Ile Glu Lys Thr Ile Ser Lys Ala Lys
        370                 375                 380

Gly Gln Pro Arg Glu Pro Gln Val Tyr Thr Leu Pro Pro Ser Arg Asp
385                 390                 395                 400

Glu Leu Thr Lys Asn Gln Val Ser Leu Thr Cys Leu Val Lys Gly Phe
                405                 410                 415

Tyr Pro Ser Asp Ile Ala Val Glu Trp Glu Ser Asn Gly Gln Pro Glu
                420                 425                 430

Asn Asn Tyr Lys Thr Thr Pro Pro Val Leu Asp Ser Asp Gly Ser Phe
            435                 440                 445

Phe Leu Tyr Ser Lys Leu Thr Val Asp Lys Ser Arg Trp Gln Gln Gly
        450                 455                 460

Asn Val Phe Ser Cys Ser Val Met His Glu Ala Leu His Asn His Tyr
465                 470                 475                 480

Thr Gln Lys Ser Leu Ser Leu Ser Pro Gly Lys
                485                 490

<210> SEQ ID NO 47
<211> LENGTH: 487
<212> TYPE: PRT
<213> ORGANISM: Artificial Sequence
<220> FEATURE:
<223> OTHER INFORMATION: aPDL1.6-dAb-Fc

<400> SEQUENCE: 47

Gln Val Gln Leu Gln Glu Ser Gly Gly Gly Ser Val Gln Ala Gly Gly
1               5                   10                  15

Ser Leu Arg Leu Ser Cys Ala Ala Ser Gly Asn Ile Ile Arg Val Arg
            20                  25                  30

Cys Met Ala Trp Phe Arg Gln Ala Pro Gly Lys Glu Arg Glu Arg Gly
        35                  40                  45

Pro Asn Ile Leu Thr Thr Thr Ile Ser Thr Tyr Leu Ala Asp Ser Val
    50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Gly Tyr Pro Thr Cys Pro Gly Pro Ala Ser Ser
                100                 105                 110
```

-continued

Gly Ala Phe Gln Tyr Trp Gly Gln Gly Thr Gln Val Thr Val Ser Ser
            115                 120                 125

Gly Ala Pro Gln Val Gln Leu Gln Glu Ser Gly Gly Gly Ser Val Gln
130                 135                 140

Ala Gly Gly Ser Leu Arg Leu Ser Cys Glu Ala Ser Gly Tyr Thr Tyr
145                 150                 155                 160

Cys Met Gly Trp Phe Arg Gln Ala Pro Gly Lys Glu Arg Glu Gly Val
                165                 170                 175

Ala Leu Ala Val Thr Gly Ile Ser Ile Pro Tyr Tyr Ala Asp Ser Val
            180                 185                 190

Lys Gly Arg Phe Thr Ile Ser Gln Asp Asn Val Lys Asn Thr Leu Tyr
            195                 200                 205

Leu Gln Met Asn Ser Leu Lys Pro Glu Asp Ala Ala Met Tyr Tyr Cys
            210                 215                 220

Ala Ala Ser Thr Ile Arg Tyr Val Cys Pro Gly Leu Asn Arg Gly Asp
225                 230                 235                 240

Gln Phe Lys Asn Trp Gly Gln Gly Thr Gln Val Thr Val Ser Ser Glu
                245                 250                 255

Pro Lys Ser Ser Asp Lys Thr His Thr Cys Pro Pro Cys Pro Ala Pro
            260                 265                 270

Glu Leu Leu Gly Gly Pro Ser Val Phe Leu Phe Pro Pro Lys Pro Lys
            275                 280                 285

Asp Thr Leu Met Ile Ser Arg Thr Pro Glu Val Thr Cys Val Val Val
            290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Ala Leu
            355                 360                 365

Pro Ala Pro Ile Glu Lys Thr Ile Ser Lys Ala Lys Gly Gln Pro Arg
            370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
            420                 425                 430

Thr Thr Pro Pro Val Leu Asp Ser Asp Gly Ser Phe Phe Leu Tyr Ser
            435                 440                 445

Lys Leu Thr Val Asp Lys Ser Arg Trp Gln Gln Gly Asn Val Phe Ser
450                 455                 460

Cys Ser Val Met His Glu Ala Leu His Asn His Tyr Thr Gln Lys Ser
465                 470                 475                 480

Leu Ser Leu Ser Pro Gly Lys
                485

<210> SEQ ID NO 48
<211> LENGTH: 491
<212> TYPE: PRT
<213> ORGANISM: Artificial Sequence
<220> FEATURE:

<223> OTHER INFORMATION: aPDL1.m3-aCTLA4.34-Fc

<400> SEQUENCE: 48

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Asp Val Asn Pro Asn Ser Gly Ser Ile Tyr Asn Gln Arg Phe
    50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Gln Val Thr Val Ser Ser
        115                 120                 125

Gly Ala Pro Gln Val Gln Leu Val Glu Ser Gly Gly Gly Leu Val Gln
    130                 135                 140

Pro Gly Gly Ser Leu Arg Leu Ser Cys Ala Ala Ser Gly Tyr Ile Tyr
145                 150                 155                 160

Ser Ala Tyr Cys Met Gly Trp Phe Arg Gln Ala Pro Gly Lys Gly Leu
                165                 170                 175

Glu Gly Val Ala Ala Ile Tyr Ile Gly Gly Ser Thr Tyr Tyr Ala
            180                 185                 190

Asp Ser Val Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
    210                 215                 220

Tyr Tyr Cys Ala Ala Asp Val Ile Pro Thr Glu Thr Cys Leu Gly Gly
225                 230                 235                 240

Ser Trp Ser Gly Pro Phe Gly Tyr Trp Gly Gln Gly Thr Leu Val Thr
                245                 250                 255

Val Ser Ser Glu Pro Lys Ser Ser Asp Lys Thr His Thr Cys Pro Pro
            260                 265                 270

Cys Pro Ala Pro Glu Leu Leu Gly Gly Pro Ser Val Phe Leu Phe Pro
        275                 280                 285

Pro Lys Pro Lys Asp Thr Leu Met Ile Ser Arg Thr Pro Glu Val Thr
    290                 295                 300

Cys Val Val Asp Val Ser His Glu Asp Pro Glu Val Lys Phe Asn
305                 310                 315                 320

Trp Tyr Val Asp Gly Val Glu Val His Asn Ala Lys Thr Lys Pro Arg
                325                 330                 335

Glu Glu Gln Tyr Asn Ser Thr Tyr Arg Val Val Ser Val Leu Thr Val
            340                 345                 350

Leu His Gln Asp Trp Leu Asn Gly Lys Glu Tyr Lys Cys Lys Val Ser
        355                 360                 365

Asn Lys Ala Leu Pro Ala Pro Ile Glu Lys Thr Ile Ser Lys Ala Lys
    370                 375                 380

Gly Gln Pro Arg Glu Pro Gln Val Tyr Thr Leu Pro Pro Ser Arg Asp
385                 390                 395                 400
```

```
Glu Leu Thr Lys Asn Gln Val Ser Leu Thr Cys Leu Val Lys Gly Phe
                405                 410                 415
Tyr Pro Ser Asp Ile Ala Val Glu Trp Glu Ser Asn Gly Gln Pro Glu
            420                 425                 430
Asn Asn Tyr Lys Thr Thr Pro Pro Val Leu Asp Ser Asp Gly Ser Phe
        435                 440                 445
Phe Leu Tyr Ser Lys Leu Thr Val Asp Lys Ser Arg Trp Gln Gln Gly
450                 455                 460
Asn Val Phe Ser Cys Ser Val Met His Glu Ala Leu His Asn His Tyr
465                 470                 475                 480
Thr Gln Lys Ser Leu Ser Leu Ser Pro Gly Lys
                485                 490

<210> SEQ ID NO 49
<211> LENGTH: 487
<212> TYPE: PRT
<213> ORGANISM: Artificial Sequence
<220> FEATURE:
<223> OTHER INFORMATION: aPDL1.m3-dAb-Fc

<400> SEQUENCE: 49

Gln Val Gln Leu Gln Glu Ser Gly Gly Gly Leu Val Gln Pro Gly Gly
1               5                   10                  15
Ser Leu Arg Leu Ser Cys Ala Ala Ser Gly Lys Met Ser Ser Arg Arg
            20                  25                  30
Cys Met Ala Trp Phe Arg Gln Ala Pro Gly Lys Glu Arg Glu Arg Val
        35                  40                  45
Ala Asp Val Asn Pro Asn Ser Gly Gly Ser Ile Tyr Asn Gln Arg Phe
    50                  55                  60
Lys Gly Arg Phe Thr Ile Ser Gln Asn Asn Ala Lys Ser Thr Val Tyr
65                  70                  75                  80
Leu Gln Met Asn Ser Leu Lys Pro Glu Asp Thr Ala Met Tyr Tyr Cys
                85                  90                  95
Ala Ala Asp Ser Phe Glu Asp Pro Thr Cys Thr Leu Val Thr Ser Ser
            100                 105                 110
Gly Ala Phe Gln Tyr Trp Gly Gln Gly Thr Gln Val Thr Val Ser Ser
        115                 120                 125
Gly Ala Pro Gln Val Gln Leu Gln Glu Ser Gly Gly Gly Ser Val Gln
    130                 135                 140
Ala Gly Gly Ser Leu Arg Leu Ser Cys Glu Ala Ser Gly Tyr Thr Tyr
145                 150                 155                 160
Cys Met Gly Trp Phe Arg Gln Ala Pro Gly Lys Glu Arg Glu Gly Val
                165                 170                 175
Ala Leu Ala Val Thr Gly Ile Ser Ile Pro Tyr Tyr Ala Asp Ser Val
            180                 185                 190
Lys Gly Arg Phe Thr Ile Ser Gln Asp Asn Val Lys Asn Thr Leu Tyr
        195                 200                 205
Leu Gln Met Asn Ser Leu Lys Pro Glu Asp Ala Ala Met Tyr Tyr Cys
    210                 215                 220
Ala Ala Ser Thr Ile Arg Tyr Val Cys Pro Gly Leu Asn Arg Gly Asp
225                 230                 235                 240
Gln Phe Lys Asn Trp Gly Gln Gly Thr Gln Val Thr Val Ser Ser Glu
                245                 250                 255
Pro Lys Ser Ser Asp Lys Thr His Thr Cys Pro Pro Cys Pro Ala Pro
            260                 265                 270
```

Glu Leu Leu Gly Gly Pro Ser Val Phe Leu Phe Pro Pro Lys Pro Lys
                275                 280                 285

Asp Thr Leu Met Ile Ser Arg Thr Pro Glu Val Thr Cys Val Val Val
        290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Ala Leu
        355                 360                 365

Pro Ala Pro Ile Glu Lys Thr Ile Ser Lys Ala Lys Gly Gln Pro Arg
    370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
            420                 425                 430

Thr Thr Pro Pro Val Leu Asp Ser Asp Gly Ser Phe Phe Leu Tyr Ser
        435                 440                 445

Lys Leu Thr Val Asp Lys Ser Arg Trp Gln Gln Gly Asn Val Phe Ser
    450                 455                 460

Cys Ser Val Met His Glu Ala Leu His Asn His Tyr Thr Gln Lys Ser
465                 470                 475                 480

Leu Ser Leu Ser Pro Gly Lys
                485

<210> SEQ ID NO 50
<211> LENGTH: 491
<212> TYPE: PRT
<213> ORGANISM: Artificial Sequence
<220> FEATURE:
<223> OTHER INFORMATION: aPDL1.9-aCTLA4.13-Fc

<400> SEQUENCE: 50

Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

Gly Ala Pro Gln Val Gln Leu Gln Glu Ser Gly Gly Gly Ser Val Gln
    130                 135                 140

Ala Gly Gly Ser Leu Arg Leu Ser Cys Ala Ala Ser Gly Tyr Ile Tyr
145                 150                 155                 160

Ser Ala Tyr Cys Met Gly Trp Phe Arg Gln Ala Pro Gly Lys Glu Arg
                165                 170                 175

Val Gly Val Ala Ala Ile Ser Ile Gly Gly Ser Thr Tyr Tyr Ala
            180                 185                 190

Asp Ser Val Lys Gly Arg Phe Thr Ile Ser Gln Asp Asn Ala Lys Asn
            195                 200                 205

Thr Leu Tyr Leu Gln Met Asn Ser Leu Lys Pro Glu Asp Thr Ala Met
    210                 215                 220

Tyr Tyr Cys Ala Ala Asp Val Ile Pro Thr Glu Thr Cys Leu Gly Gly
225                 230                 235                 240

Ser Trp Ser Gly Pro Phe Gly Tyr Trp Gly Gln Gly Thr Gln Val Thr
                245                 250                 255

Val Ser Ser Glu Pro Lys Ser Ser Asp Lys Thr His Thr Cys Pro Pro
            260                 265                 270

Cys Pro Ala Pro Glu Leu Leu Gly Gly Pro Ser Val Phe Leu Phe Pro
        275                 280                 285

Pro Lys Pro Lys Asp Thr Leu Met Ile Ser Arg Thr Pro Glu Val Thr
290                 295                 300

Cys Val Val Val Asp Val Ser His Glu Asp Pro Glu Val Lys Phe Asn
305                 310                 315                 320

Trp Tyr Val Asp Gly Val Glu Val His Asn Ala Lys Thr Lys Pro Arg
                325                 330                 335

Glu Glu Gln Tyr Asn Ser Thr Tyr Arg Val Val Ser Val Leu Thr Val
            340                 345                 350

Leu His Gln Asp Trp Leu Asn Gly Lys Glu Tyr Lys Cys Lys Val Ser
    355                 360                 365

Asn Lys Ala Leu Pro Ala Pro Ile Glu Lys Thr Ile Ser Lys Ala Lys
370                 375                 380

Gly Gln Pro Arg Glu Pro Gln Val Tyr Thr Leu Pro Pro Ser Arg Asp
385                 390                 395                 400

Glu Leu Thr Lys Asn Gln Val Ser Leu Thr Cys Leu Val Lys Gly Phe
                405                 410                 415

Tyr Pro Ser Asp Ile Ala Val Glu Trp Glu Ser Asn Gly Gln Pro Glu
            420                 425                 430

Asn Asn Tyr Lys Thr Thr Pro Pro Val Leu Asp Ser Asp Gly Ser Phe
    435                 440                 445

Phe Leu Tyr Ser Lys Leu Thr Val Asp Lys Ser Arg Trp Gln Gln Gly
450                 455                 460

Asn Val Phe Ser Cys Ser Val Met His Glu Ala Leu His Asn His Tyr
465                 470                 475                 480

Thr Gln Lys Ser Leu Ser Leu Ser Pro Gly Lys
                485                 490

<210> SEQ ID NO 51
<211> LENGTH: 487
<212> TYPE: PRT
<213> ORGANISM: Artificial Sequence
<220> FEATURE:
<223> OTHER INFORMATION: dAb-aCTLA4.13-Fc

<400> SEQUENCE: 51

Gln Val Gln Leu Gln Glu Ser Gly Gly Gly Ser Val Gln Ala Gly Gly
1               5                   10                  15

```
Ser Leu Arg Leu Ser Cys Glu Ala Ser Gly Tyr Thr Tyr Cys Met Gly
            20                  25                  30

Trp Phe Arg Gln Ala Pro Gly Lys Glu Arg Glu Gly Val Ala Leu Ala
            35                  40                  45

Val Thr Gly Ile Ser Ile Pro Tyr Tyr Ala Asp Ser Val Lys Gly Arg
            50                  55                  60

Phe Thr Ile Ser Gln Asp Asn Val Lys Asn Thr Leu Tyr Leu Gln Met
65                  70                  75                  80

Asn Ser Leu Lys Pro Glu Asp Ala Ala Met Tyr Tyr Cys Ala Ala Ser
                85                  90                  95

Thr Ile Arg Tyr Val Cys Pro Gly Leu Asn Arg Gly Asp Gln Phe Lys
            100                 105                 110

Asn Trp Gly Gln Gly Thr Gln Val Thr Val Ser Ser Gly Ala Pro Gln
            115                 120                 125

Val Gln Leu Gln Glu Ser Gly Gly Ser Val Gln Ala Gly Gly Ser
            130                 135                 140

Leu Arg Leu Ser Cys Ala Ala Ser Gly Tyr Ile Tyr Ser Ala Tyr Cys
145                 150                 155                 160

Met Gly Trp Phe Arg Gln Ala Pro Gly Lys Glu Arg Val Gly Val Ala
            165                 170                 175

Ala Ile Ser Ile Gly Gly Ser Thr Tyr Tyr Ala Asp Ser Val Lys
            180                 185                 190

Gly Arg Phe Thr Ile Ser Gln Asp Asn Ala Lys Asn Thr Leu Tyr Leu
            195                 200                 205

Gln Met Asn Ser Leu Lys Pro Glu Asp Thr Ala Met Tyr Tyr Cys Ala
210                 215                 220

Ala Asp Val Ile Pro Thr Glu Thr Cys Leu Gly Gly Ser Trp Ser Gly
225                 230                 235                 240

Pro Phe Gly Tyr Trp Gly Gln Gly Thr Gln Val Thr Val Ser Ser Glu
            245                 250                 255

Pro Lys Ser Ser Asp Lys Thr His Thr Cys Pro Pro Cys Pro Ala Pro
            260                 265                 270

Glu Leu Leu Gly Gly Pro Ser Val Phe Leu Phe Pro Pro Lys Pro Lys
            275                 280                 285

Asp Thr Leu Met Ile Ser Arg Thr Pro Glu Val Thr Cys Val Val Val
            290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
            325                 330                 335

Asn Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Ala Leu
            355                 360                 365

Pro Ala Pro Ile Glu Lys Thr Ile Ser Lys Ala Lys Gly Gln Pro Arg
            370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
            420                 425                 430

Thr Thr Pro Pro Val Leu Asp Ser Asp Gly Ser Phe Phe Leu Tyr Ser
```

```
             435                 440                 445
Lys Leu Thr Val Asp Lys Ser Arg Trp Gln Gln Gly Asn Val Phe Ser
    450                 455                 460

Cys Ser Val Met His Glu Ala Leu His Asn His Tyr Thr Gln Lys Ser
465                 470                 475                 480

Leu Ser Leu Ser Pro Gly Lys
                485

<210> SEQ ID NO 52
<211> LENGTH: 357
<212> TYPE: PRT
<213> ORGANISM: Artificial Sequence
<220> FEATURE:
<223> OTHER INFORMATION: CTLA4-muFc

<400> SEQUENCE: 52

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp Gln Gly Ser Met
            115                 120                 125

Asp Pro Lys Ser Ser Asp Lys Thr His Thr Cys Pro Pro Cys Pro Ala
    130                 135                 140

Pro Glu Val Ser Ser Val Phe Ile Phe Pro Pro Lys Pro Lys Asp Val
145                 150                 155                 160

Leu Thr Ile Thr Leu Thr Pro Lys Val Thr Cys Val Val Val Asp Ile
                165                 170                 175

Ser Lys Asp Asp Pro Glu Val Gln Phe Ser Trp Phe Val Asp Asp Val
            180                 185                 190

Glu Val His Thr Ala Gln Thr Gln Pro Arg Glu Glu Gln Phe Asn Ser
        195                 200                 205

Thr Phe Arg Ser Val Ser Glu Leu Pro Ile Met His Gln Asp Trp Leu
    210                 215                 220

Asn Gly Lys Glu Phe Lys Cys Arg Val Asn Ser Ala Ala Phe Pro Ala
225                 230                 235                 240

Pro Ile Glu Lys Thr Ile Ser Lys Thr Lys Gly Arg Pro Lys Ala Pro
                245                 250                 255

Gln Val Tyr Thr Ile Pro Pro Lys Glu Gln Met Ala Lys Asp Lys
            260                 265                 270

Val Ser Leu Thr Cys Met Ile Thr Asp Phe Phe Pro Glu Asp Ile Thr
        275                 280                 285

Val Glu Trp Gln Trp Asn Gly Gln Pro Ala Glu Asn Tyr Lys Asn Thr
    290                 295                 300

Gln Pro Ile Met Asn Thr Asn Gly Ser Tyr Phe Val Tyr Ser Lys Leu
```

```
                305                 310                 315                 320
Asn Val Gln Lys Ser Asn Trp Glu Ala Gly Asn Thr Phe Thr Cys Ser
                    325                 330                 335
Val Leu His Glu Gly Leu His Asn His His Thr Glu Lys Ser Leu Ser
                    340                 345                 350
His Ser Pro Gly Lys
        355

<210> SEQ ID NO 53
<211> LENGTH: 452
<212> TYPE: PRT
<213> ORGANISM: Artificial Sequence
<220> FEATURE:
<223> OTHER INFORMATION: PD-L1-muFc

<400> SEQUENCE: 53

Thr Val Thr Val Pro Lys Asp Leu Tyr Val Glu Tyr Gly Ser Asn
1               5                   10                  15
Met Thr Ile Glu Cys Lys Phe Pro Val Glu Lys Gln Leu Asp Leu Ala
                    20                  25                  30
Ala Leu Ile Val Tyr Trp Glu Met Glu Asp Lys Asn Ile Ile Gln Phe
                35                  40                  45
Val His Gly Glu Glu Asp Leu Lys Val Gln His Ser Ser Tyr Arg Gln
            50                  55                  60
Arg Ala Arg Leu Leu Lys Asp Gln Leu Ser Leu Gly Asn Ala Ala Leu
65                  70                  75                  80
Gln Ile Thr Asp Val Lys Leu Gln Asp Ala Gly Val Tyr Arg Cys Met
                    85                  90                  95
Ile Ser Tyr Gly Gly Ala Asp Tyr Lys Arg Ile Thr Val Lys Val Asn
                100                 105                 110
Ala Pro Tyr Asn Lys Ile Asn Gln Arg Ile Leu Val Val Asp Pro Val
            115                 120                 125
Thr Ser Glu His Glu Leu Thr Cys Gln Ala Glu Gly Tyr Pro Lys Ala
        130                 135                 140
Glu Val Ile Trp Thr Ser Ser Asp His Gln Val Leu Ser Gly Lys Thr
145                 150                 155                 160
Thr Thr Thr Asn Ser Lys Arg Glu Glu Asn Leu Phe Asn Val Thr Ser
                    165                 170                 175
Thr Leu Arg Ile Asn Thr Thr Asn Glu Ile Phe Tyr Cys Thr Phe
                180                 185                 190
Arg Arg Leu Asp Pro Glu Glu Asn His Thr Ala Glu Leu Val Ile Pro
            195                 200                 205
Glu Leu Pro Leu Ala His Pro Pro Asn Glu Arg Thr Gly Ser Met Asp
        210                 215                 220
Pro Lys Ser Ser Asp Lys Thr His Thr Cys Pro Pro Cys Pro Ala Pro
225                 230                 235                 240
Glu Val Ser Ser Val Phe Ile Phe Pro Pro Lys Pro Lys Asp Val Leu
                    245                 250                 255
Thr Ile Thr Leu Thr Pro Lys Val Thr Cys Val Val Val Asp Ile Ser
                260                 265                 270
Lys Asp Asp Pro Glu Val Gln Phe Ser Trp Phe Val Asp Asp Val Glu
            275                 280                 285
Val His Thr Ala Gln Thr Gln Pro Arg Glu Glu Gln Phe Asn Ser Thr
        290                 295                 300
Phe Arg Ser Val Ser Glu Leu Pro Ile Met His Gln Asp Trp Leu Asn
```

```
                305                 310                 315                 320
    Gly Lys Glu Phe Lys Cys Arg Val Asn Ser Ala Ala Phe Pro Ala Pro
                    325                 330                 335

Ile Glu Lys Thr Ile Ser Lys Thr Lys Gly Arg Pro Lys Ala Pro Gln
                    340                 345                 350

Val Tyr Thr Ile Pro Pro Lys Glu Gln Met Ala Lys Asp Lys Val
                    355                 360                 365

Ser Leu Thr Cys Met Ile Thr Asp Phe Phe Pro Glu Asp Ile Thr Val
                370                 375                 380

Glu Trp Gln Trp Asn Gly Gln Pro Ala Glu Asn Tyr Lys Asn Thr Gln
    385                 390                 395                 400

Pro Ile Met Asn Thr Asn Gly Ser Tyr Phe Val Tyr Ser Lys Leu Asn
                    405                 410                 415

Val Gln Lys Ser Asn Trp Glu Ala Gly Asn Thr Phe Thr Cys Ser Val
                    420                 425                 430

Leu His Glu Gly Leu His Asn His His Thr Glu Lys Ser Leu Ser His
                    435                 440                 445

Ser Pro Gly Lys
        450

<210> SEQ ID NO 54
<211> LENGTH: 448
<212> TYPE: PRT
<213> ORGANISM: Artificial Sequence
<220> FEATURE:
<223> OTHER INFORMATION: PD-L1-huFc

<400> SEQUENCE: 54

Thr Val Thr Val Pro Lys Asp Leu Tyr Val Val Glu Tyr Gly Ser Asn
    1               5                   10                  15

Met Thr Ile Glu Cys Lys Phe Pro Val Glu Lys Gln Leu Asp Leu Ala
                    20                  25                  30

Ala Leu Ile Val Tyr Trp Glu Met Glu Asp Lys Asn Ile Ile Gln Phe
                35                  40                  45

Val His Gly Glu Glu Asp Leu Lys Val Gln His Ser Ser Tyr Arg Gln
            50                  55                  60

Arg Ala Arg Leu Leu Lys Asp Gln Leu Ser Leu Gly Asn Ala Ala Leu
    65                  70                  75                  80

Gln Ile Thr Asp Val Lys Leu Gln Asp Ala Gly Val Tyr Arg Cys Met
                    85                  90                  95

Ile Ser Tyr Gly Gly Ala Asp Tyr Lys Arg Ile Thr Val Lys Val Asn
                100                 105                 110

Ala Pro Tyr Asn Lys Ile Asn Gln Arg Ile Leu Val Val Asp Pro Val
                115                 120                 125

Thr Ser Glu His Glu Leu Thr Cys Gln Ala Glu Gly Tyr Pro Lys Ala
    130                 135                 140

Glu Val Ile Trp Thr Ser Ser Asp His Gln Val Leu Ser Gly Lys Thr
    145                 150                 155                 160

Thr Thr Thr Asn Ser Lys Arg Glu Glu Asn Leu Phe Asn Val Thr Ser
                    165                 170                 175

Thr Leu Arg Ile Asn Thr Thr Thr Asn Glu Ile Phe Tyr Cys Thr Phe
                180                 185                 190

Arg Arg Leu Asp Pro Glu Glu Asn His Thr Ala Glu Leu Val Ile Pro
                195                 200                 205

Glu Leu Pro Leu Ala His Pro Pro Asn Glu Arg Thr Asp Asp Lys Thr
```

-continued

```
                210                 215                 220
His Thr Cys Pro Pro Cys Pro Ala Pro Glu Leu Leu Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445
```

<210> SEQ ID NO 55
<211> LENGTH: 442
<212> TYPE: PRT
<213> ORGANISM: Artificial Sequence
<220> FEATURE:
<223> OTHER INFORMATION: CD80-muFc

<400> SEQUENCE: 55

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
                20                  25                  30

Gln Lys Glu Lys Lys Met Val Leu Thr Met Met Ser Gly Asp Met Asn
                35                  40                  45

Ile Trp Pro Glu Tyr Lys Asn Arg Thr Ile Phe Asp Ile Thr Asn Asn
50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
                100                 105                 110

Ile Ser Asp Phe Glu Ile Pro Thr Ser Asn Ile Arg Arg Ile Ile Cys
                115                 120                 125

Ser Thr Ser Gly Gly Phe Pro Glu Pro His Leu Ser Trp Leu Glu Asn
```

```
          130                 135                 140
Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
                180                 185                 190

Gln Thr Phe Asn Trp Asn Thr Thr Lys Gln Glu His Phe Pro Asp Asn
            195                 200                 205

Ile Glu Gly Arg Met Asp Pro Lys Ser Asp Lys Thr His Thr Cys
210                 215                 220

Pro Pro Cys Pro Ala Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
                260                 265                 270

Phe Val Asp Asp Val Glu Val His Thr Ala Gln Thr Gln Pro Arg Glu
                275                 280                 285

Glu Gln Phe Asn Ser Thr Phe Arg Ser Val Ser Glu Leu Pro Ile Met
            290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
                340                 345                 350

Met Ala Lys Asp Lys Val Ser Leu Thr Cys Met Ile Thr Asp Phe Phe
            355                 360                 365

Pro Glu Asp Ile Thr Val Glu Trp Gln Trp Asn Gly Gln Pro Ala Glu
        370                 375                 380

Asn Tyr Lys Asn Thr Gln Pro Ile Met Asn Thr Asn Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
                420                 425                 430

Glu Lys Ser Leu Ser His Ser Pro Gly Lys
            435                 440

<210> SEQ ID NO 56
<211> LENGTH: 357
<212> TYPE: PRT
<213> ORGANISM: Artificial Sequence
<220> FEATURE:
<223> OTHER INFORMATION: CTLA4-huFc

<400> SEQUENCE: 56

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
```

```
                50                  55                  60
Ile Cys Thr Gly Thr Ser Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
            115                 120                 125

Ser Ser Asp Lys Thr His Thr Cys Pro Pro Cys Pro Ala Pro Glu Leu
130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
            195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
            290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 57
<211> LENGTH: 449
<212> TYPE: PRT
<213> ORGANISM: Artificial Sequence
<220> FEATURE:
<223> OTHER INFORMATION: CD86-muFc

<400> SEQUENCE: 57

Tyr Phe Asn Glu Thr Ala Asp Leu Pro Cys Gln Phe Ala Asn Ser Gln
 1               5                  10                  15

Asn Gln Ser Leu Ser Glu Leu Val Val Phe Trp Gln Asp Gln Glu Asn
                20                  25                  30

Leu Val Leu Asn Glu Val Tyr Leu Gly Lys Glu Lys Phe Asp Ser Val
            35                  40                  45

His Ser Lys Tyr Met Gly Arg Thr Ser Phe Asp Ser Asp Ser Trp Thr
```

```
            50                  55                  60
Leu Arg Leu His Asn Leu Gln Ile Lys Asp Lys Gly Leu Tyr Gln Cys
 65                  70                  75                  80

Ile Ile His His Lys Lys Pro Thr Gly Met Ile Arg Ile His Gln Met
                 85                  90                  95

Asn Ser Glu Leu Ser Val Leu Ala Asn Phe Ser Gln Pro Glu Ile Val
                100                 105                 110

Pro Ile Ser Asn Ile Thr Glu Asn Val Tyr Ile Asn Leu Thr Cys Ser
                115                 120                 125

Ser Ile His Gly Tyr Pro Glu Pro Lys Lys Met Ser Val Leu Leu Arg
                130                 135                 140

Thr Lys Asn Ser Thr Ile Glu Tyr Asp Gly Ile Met Gln Lys Ser Gln
145                 150                 155                 160

Asp Asn Val Thr Glu Leu Tyr Asp Val Ser Ile Ser Leu Ser Val Ser
                165                 170                 175

Phe Pro Asp Val Thr Ser Asn Met Thr Ile Phe Cys Ile Leu Glu Thr
                180                 185                 190

Asp Lys Thr Arg Leu Leu Ser Ser Pro Phe Ser Ile Glu Leu Glu Asp
                195                 200                 205

Pro Gln Pro Pro Pro Asp His Ile Pro Gly Ser Met Asp Pro Lys Ser
                210                 215                 220

Ser Asp Lys Thr His Thr Cys Pro Pro Cys Pro Ala Pro Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Lys Asp Asp
                260                 265                 270

Pro Glu Val Gln Phe Ser Trp Phe Val Asp Asp Val Glu Val His Thr
                275                 280                 285

Ala Gln Thr Gln Pro Arg Glu Glu Gln Phe Asn Ser Thr Phe Arg Ser
                290                 295                 300

Val Ser Glu Leu Pro Ile Met His Gln Asp Trp Leu Asn Gly Lys Glu
305                 310                 315                 320

Phe Lys Cys Arg Val Asn Ser Ala Ala Phe Pro Ala Pro Ile Glu Lys
                325                 330                 335

Thr Ile Ser Lys Thr Lys Gly Arg Pro Lys Ala Pro Gln Val Tyr Thr
                340                 345                 350

Ile Pro Pro Pro Lys Glu Gln Met Ala Lys Asp Lys Val Ser Leu Thr
                355                 360                 365

Cys Met Ile Thr Asp Phe Phe Pro Glu Asp Ile Thr Val Glu Trp Gln
                370                 375                 380

Trp Asn Gly Gln Pro Ala Glu Asn Tyr Lys Asn Thr Gln Pro Ile Met
385                 390                 395                 400

Asn Thr Asn Gly Ser Tyr Phe Val Tyr Ser Lys Leu Asn Val Gln Lys
                405                 410                 415

Ser Asn Trp Glu Ala Gly Asn Thr Phe Thr Cys Ser Val Leu His Glu
                420                 425                 430

Gly Leu His Asn His His Thr Glu Lys Ser Leu Ser His Ser Pro Gly
                435                 440                 445

Lys
```

<210> SEQ ID NO 58
<211> LENGTH: 381

```
<212> TYPE: PRT
<213> ORGANISM: Artificial Sequence
<220> FEATURE:
<223> OTHER INFORMATION: PD1-muFc

<400> SEQUENCE: 58
```

| | | | | | | | | | | | | | | |
|---|---|---|---|---|---|---|---|---|---|---|---|---|---|---|
| Pro | Gly | Trp | Phe | Leu | Asp | Ser | Pro | Asp | Arg | Pro | Trp | Asn | Pro | Thr |
| 1 | | | | 5 | | | | | 10 | | | | | 15 |
| Phe | Ser | Pro | Ala | Leu | Leu | Val | Val | Thr | Glu | Gly | Asp | Asn | Ala | Thr | Phe |
| | | | 20 | | | | | 25 | | | | | 30 | | |
| Thr | Cys | Ser | Phe | Ser | Asn | Thr | Ser | Glu | Ser | Phe | Val | Leu | Asn | Trp | Tyr |
| | | | 35 | | | | | 40 | | | | | 45 | | |
| Arg | Met | Ser | Pro | Ser | Asn | Gln | Thr | Asp | Lys | Leu | Ala | Ala | Phe | Pro | Glu |
| | 50 | | | | | 55 | | | | | 60 | | | | |
| Asp | Arg | Ser | Gln | Pro | Gly | Gln | Asp | Cys | Arg | Phe | Arg | Val | Thr | Gln | Leu |
| 65 | | | | | 70 | | | | | 75 | | | | | 80 |
| Pro | Asn | Gly | Arg | Asp | Phe | His | Met | Ser | Val | Val | Arg | Ala | Arg | Arg | Asn |
| | | | | 85 | | | | | 90 | | | | | 95 | |
| Asp | Ser | Gly | Thr | Tyr | Leu | Cys | Gly | Ala | Ile | Ser | Leu | Ala | Pro | Lys | Ala |
| | | | 100 | | | | | 105 | | | | | 110 | | |
| Gln | Ile | Lys | Glu | Ser | Leu | Arg | Ala | Glu | Leu | Arg | Val | Thr | Glu | Arg | Arg |
| | | | 115 | | | | | 120 | | | | | 125 | | |
| Ala | Glu | Val | Pro | Thr | Ala | His | Pro | Ser | Pro | Ser | Pro | Arg | Pro | Ala | Gly |
| | 130 | | | | | 135 | | | | | 140 | | | | |
| Gln | Phe | Gln | Ile | Glu | Gly | Arg | Met | Asp | Pro | Lys | Ser | Ser | Asp | Lys | Thr |
| 145 | | | | | 150 | | | | | 155 | | | | | 160 |
| His | Thr | Cys | Pro | Pro | Cys | Pro | Ala | Pro | Glu | Val | Ser | Ser | Val | Phe | Ile |
| | | | | 165 | | | | | 170 | | | | | 175 | |
| Phe | Pro | Pro | Lys | Pro | Lys | Asp | Val | Leu | Thr | Ile | Thr | Leu | Thr | Pro | Lys |
| | | | 180 | | | | | 185 | | | | | 190 | | |
| Val | Thr | Cys | Val | Val | Val | Asp | Ile | Ser | Lys | Asp | Asp | Pro | Glu | Val | Gln |
| | | | 195 | | | | | 200 | | | | | 205 | | |
| Phe | Ser | Trp | Phe | Val | Asp | Asp | Val | Glu | Val | His | Thr | Ala | Gln | Thr | Gln |
| | 210 | | | | | 215 | | | | | 220 | | | | |
| Pro | Arg | Glu | Glu | Gln | Phe | Asn | Ser | Thr | Phe | Arg | Ser | Val | Ser | Glu | Leu |
| 225 | | | | | 230 | | | | | 235 | | | | | 240 |
| Pro | Ile | Met | His | Gln | Asp | Trp | Leu | Asn | Gly | Lys | Glu | Phe | Lys | Cys | Arg |
| | | | | 245 | | | | | 250 | | | | | 255 | |
| Val | Asn | Ser | Ala | Ala | Phe | Pro | Ala | Pro | Ile | Glu | Lys | Thr | Ile | Ser | Lys |
| | | | 260 | | | | | 265 | | | | | 270 | | |
| Thr | Lys | Gly | Arg | Pro | Lys | Ala | Pro | Gln | Val | Tyr | Thr | Ile | Pro | Pro | Pro |
| | | | 275 | | | | | 280 | | | | | 285 | | |
| Lys | Glu | Gln | Met | Ala | Lys | Asp | Lys | Val | Ser | Leu | Thr | Cys | Met | Ile | Thr |
| | 290 | | | | | 295 | | | | | 300 | | | | |
| Asp | Phe | Phe | Pro | Glu | Asp | Ile | Thr | Val | Glu | Trp | Gln | Trp | Asn | Gly | Gln |
| 305 | | | | | 310 | | | | | 315 | | | | | 320 |
| Pro | Ala | Glu | Asn | Tyr | Lys | Asn | Thr | Gln | Pro | Ile | Met | Asn | Thr | Asn | Gly |
| | | | | 325 | | | | | 330 | | | | | 335 | |
| Ser | Tyr | Phe | Val | Tyr | Ser | Lys | Leu | Asn | Val | Gln | Lys | Ser | Asn | Trp | Glu |
| | | | 340 | | | | | 345 | | | | | 350 | | |
| Ala | Gly | Asn | Thr | Phe | Thr | Cys | Ser | Val | Leu | His | Glu | Gly | Leu | His | Asn |
| | | | 355 | | | | | 360 | | | | | 365 | | |
| His | His | Thr | Glu | Lys | Ser | Leu | Ser | His | Ser | Pro | Gly | Lys | | | |
| | 370 | | | | | 375 | | | | | 380 | | | | |

<210> SEQ ID NO 59
<211> LENGTH: 448
<212> TYPE: PRT
<213> ORGANISM: Artificial Sequence
<220> FEATURE:
<223> OTHER INFORMATION: Ipilimumab HC

<400> SEQUENCE: 59

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Thr Met His Trp Val Arg Gln Ala Pro Gly Lys Gly Leu Glu Trp Val
            35                  40                  45

Thr Phe Ile Ser Tyr Asp Gly Asn Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365
```

```
Leu Val Lys Gly Phe Tyr Pro Ser Asp Ile Ala Val Glu Trp Glu Ser
    370             375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
                435                 440                 445
```

<210> SEQ ID NO 60
<211> LENGTH: 215
<212> TYPE: PRT
<213> ORGANISM: Artificial Sequence
<220> FEATURE:
<223> OTHER INFORMATION: Ipilimumab LC

<400> SEQUENCE: 60

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Gly Ser Ser
                20                  25                  30
Tyr Leu Ala Trp Tyr Gln Gln Lys Pro Gly Gln Ala Pro Arg Leu Leu
            35                  40                  45
Ile Tyr Gly Ala Phe Ser Arg Ala Thr Gly Ile Pro Asp Arg Phe Ser
        50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Trp Thr Phe Gly Gln Gly Thr Lys Val Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
    210                 215
```

<210> SEQ ID NO 61
<211> LENGTH: 451
<212> TYPE: PRT
<213> ORGANISM: Artificial Sequence
<220> FEATURE:
<223> OTHER INFORMATION: Durvalumab HC

<400> SEQUENCE: 61

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430
```

His Glu Ala Leu His Asn His Tyr Thr Gln Lys Ser Leu Ser Leu Ser
              435                 440                 445

Pro Gly Lys
    450

<210> SEQ ID NO 62
<211> LENGTH: 215
<212> TYPE: PRT
<213> ORGANISM: Artificial Sequence
<220> FEATURE:
<223> OTHER INFORMATION: Durvalumab LC

<400> SEQUENCE: 62

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 63
<211> LENGTH: 220
<212> TYPE: PRT
<213> ORGANISM: Artificial Sequence
<220> FEATURE:
<223> OTHER INFORMATION: human PD-L1

<400> SEQUENCE: 63

Thr Val Thr Val Pro Lys Asp Leu Tyr Val Val Glu Tyr Gly Ser Asn
1               5                   10                  15

Met Thr Ile Glu Cys Lys Phe Pro Val Glu Lys Gln Leu Asp Leu Ala
            20                  25                  30

Ala Leu Ile Val Tyr Trp Glu Met Glu Asp Lys Asn Ile Ile Gln Phe
        35                  40                  45

Val His Gly Glu Glu Asp Leu Lys Val Gln His Ser Ser Tyr Arg Gln
    50                  55                  60

```
Arg Ala Arg Leu Leu Lys Asp Gln Leu Ser Leu Gly Asn Ala Ala Leu
 65              70                  75                  80

Gln Ile Thr Asp Val Lys Leu Gln Asp Ala Gly Val Tyr Arg Cys Met
             85                  90                  95

Ile Ser Tyr Gly Gly Ala Asp Tyr Lys Arg Ile Thr Val Lys Val Asn
            100                 105                 110

Ala Pro Tyr Asn Lys Ile Asn Gln Arg Ile Leu Val Val Asp Pro Val
            115                 120                 125

Thr Ser Glu His Glu Leu Thr Cys Gln Ala Glu Gly Tyr Pro Lys Ala
130                 135                 140

Glu Val Ile Trp Thr Ser Ser Asp His Gln Val Leu Ser Gly Lys Thr
145                 150                 155                 160

Thr Thr Thr Asn Ser Lys Arg Glu Glu Asn Leu Phe Asn Val Thr Ser
                165                 170                 175

Thr Leu Arg Ile Asn Thr Thr Thr Asn Glu Ile Phe Tyr Cys Thr Phe
                180                 185                 190

Arg Arg Leu Asp Pro Glu Glu Asn His Thr Ala Glu Leu Val Ile Pro
            195                 200                 205

Glu Leu Pro Leu Ala His Pro Pro Asn Glu Arg Thr
    210                 215                 220

<210> SEQ ID NO 64
<211> LENGTH: 127
<212> TYPE: PRT
<213> ORGANISM: Artificial Sequence
<220> FEATURE:
<223> OTHER INFORMATION: N-terminal IgV domain of human PD-L1

<400> SEQUENCE: 64

Met Arg Ile Phe Ala Val Phe Ile Phe Met Thr Tyr Trp His Leu Leu
  1               5                  10                  15

Asn Ala Phe Thr Val Thr Val Pro Lys Asp Leu Tyr Val Val Glu Tyr
             20                  25                  30

Gly Ser Asn Met Thr Ile Glu Cys Lys Phe Pro Val Glu Lys Gln Leu
             35                  40                  45

Asp Leu Ala Ala Leu Ile Val Tyr Trp Glu Met Glu Asp Lys Asn Ile
 50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
             85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr
            115                 120                 125
```

DIMERS AND USE THEREOF

CROSS-REFERENCE TO RELATED APPLICATIONS

This application is a continuation of Patent Cooperation Treaty Application PCT/CN2019/089980, filed Jun. 4, 2019, which claims the benefit of Patent Cooperation Treaty Applications PCT/CN2018/090012, filed Jun. 5, 2018, and PCT/CN2019/086821, filed May 14, 2019. Priority is claimed to those applications and their disclosures are incorporated herein by reference in their entirety.

SEQUENCE LISTING

The instant application contains a Sequence Listing which has been submitted electronically in ASCII format and is hereby incorporated by reference in its entirety. The electronic copy of the Sequence Listing, created on Sep. 30, 2020, is named 025796_US002_SL.txt and is 127,503 bytes in size.

BACKGROUND OF THE INVENTION

Blockade of the PD1/PD-L1 interaction could lead to enhanced tumor-specific T-cell immunity, which in turn will lead to clearance of tumor cells by the immune system. Programmed Death Ligand-1 (PD-L1) is expressed on antigen-presenting cells as well as many human cancer cells and have been shown to down-regulate T cell activation and cytokine secretion upon binding to PD-1.

Similarly, abrogating immune regulatory molecules such as cytotoxic T lymphocyte antigen 4 (CTLA4) represents a new and promising strategy to induce tumor regression and prolong patient survival by manipulation of the immune system. Anti-CTLA4 antibodies (such as ipilimumab) have also been developed and marketed for the treatment of cancer.

Recently, reports of concurrent therapy using separate intravenous doses of PD1/PD-L1 antibody and CTLA4 antibody were shown. However, there are a number of drawbacks associated with these concurrent therapies. For example, there is increased inconvenience to the patient, added pain, and added difficulty of manufacturing and characterizing multiple agents. In addition, sub-optimal efficacy and safety issues have been reported. Thus, there is still an unmet medical need for new promising agents for the treatment of cancers, especially agents capable of simultaneously acting on various targets.

SUMMARY OF THE INVENTION

The present disclosure provides a dimer comprising two polypeptide chain monomers, with each of the two polypeptide chain monomers comprising an antibody Fc subunit. The dimer comprises two or more immunoglobulin single variable domains (ISVDs), at least one of the ISVDs is specific for PD-L1, and at least one of the ISVDs is specific for CTLA4. The present disclosure also provides an immunoconjugate comprising the dimer, a method for producing the dimer, as well as a pharmaceutical composition comprising the dimer and a use of the dimer as well as the pharmaceutical composition. The dimer can be used in the treatment of a disease in a subject in need thereof, or in the preparation of a medicament for treating a disease, such as cancer.

In one aspect, the present disclosure provides a dimer. The dimer may be formed by two polypeptide chains, with each of the two polypeptide chains comprising an antibody Fc subunit. The dimer may comprise two or more immunoglobulin single variable domains (ISVDs), at least one of the ISVDs is specific for PD-L1, and at least one of the ISVDs is specific for CTLA4.

In some embodiments, at least one of the two polypeptide chains comprise both an ISVD specific for PD-L1 and an ISVD specific for CTLA4.

In some embodiments, each of the two polypeptide chains comprises both an ISVD specific for PD-L1 and an ISVD specific for CTLA4.

In some embodiments, for one or both of the two polypeptide chains, the ISVD specific for PD-L1 is fused to the ISVD specific for CTLA4, optionally via a linker.

In some embodiments, for one or both of the two polypeptide chains: the ISVD specific for PD-L1 is fused to the ISVD specific for CTLA4, optionally via a linker, and the ISVD specific for CTLA4 is fused to the antibody Fc subunit, optionally via a linker.

In some embodiments, for one or both of the two polypeptide chains: C terminus of the ISVD specific for PD-L1 is fused to N terminus of the ISVD specific for CTLA4, optionally via a linker; and C terminus of the ISVD specific for CTLA4 is fused to N terminus of the antibody Fc subunit, optionally via a linker.

In some embodiments, for one or both of the two polypeptide chains: the ISVD specific for PD-L1 is fused to the ISVD specific for CTLA4, optionally via a linker; and the ISVD specific for PD-L1 is fused to the antibody Fc subunit, optionally via a linker.

In some embodiments, for one or both of the two polypeptide chains: C terminus of the ISVD specific for CTLA4 is fused to N terminus of the ISVD specific for PD-L1, optionally via a linker; and C terminus of the ISVD specific for PD-L1 is fused to N terminus of the antibody Fc subunit, optionally via a linker.

In some embodiments, the antibody Fc subunit is derived from an IgG Fc subunit, such as human IgG1. The antibody Fc subunit may comprise an amino acid sequence as set forth in any one of SEQ ID NO: 35, 38 and 39.

In some embodiments, the ISVD specific for PD-L1 is capable of binding to N-terminal IgV domain of human PD-L1.

In some embodiments, the ISVD specific for PD-L1 is capable of binding to residues I54, Y56, E58, Q66 and/or R113 of human PD-L1.

In some embodiments, the ISVD specific for PD-L1 is capable of further binding to residues D61, N63, V68, M115, S117, Y123 and/or R125 of human PD-L1.

In some embodiments, the ISVD specific for PD-L1 is capable of binding to a conformational epitope of human PD-L1, the conformational epitope comprises residues I54, Y56, E58, Q66 and R113 of the human PD-L1.

In some embodiments, the ISVD specific for PD-L1 is capable of binding to a conformational epitope of human PD-L1 N-terminal IgV domain, the conformational epitope comprises residues I54, Y56, E58, Q66, R113, D61, N63, V68, M115, S117, Y123 and R125 of the human PD-L1 N-terminal IgV domain.

In some embodiments, the human PD-L1 N-terminal IgV domain comprises an amino acid sequence as set forth in SEQ ID NO: 64.

In some embodiments, the ISVD specific for PD-L1 is capable of blocking binding of PD-L1 to PD1.

In some embodiments, the ISVD specific for PD-L1 is capable of blocking binding of PD-L1 to CD80.

In some embodiments, the ISVD specific for PD-L1 cross-competes for binding to PD-L1 with a reference anti-PD-L1 antibody, the reference anti-PD-L1 antibody comprises a heavy chain CDR3 comprising an amino acid sequence as set forth in SEQ ID NO: 1. In some embodiments, the reference anti-PD-L1 antibody comprises a heavy chain CDR3 comprising an amino acid sequence as set forth in any one of SEQ ID NO: 5 and 9. In some embodiments, the reference anti-PD-L1 antibody comprises a heavy chain CDR1 comprising an amino acid sequence as set forth in SEQ ID NO: 2. In some embodiments, the reference anti-PD-L1 antibody comprises a heavy chain CDR1 comprising an amino acid sequence as set forth in any one of SEQ ID NO: 3 and 7. In some embodiments, the reference anti-PD-L1 antibody comprises a heavy chain CDR2 comprising an amino acid sequence as set forth in any one of SEQ ID NO: 4, 8 and 11. In some embodiments, the reference anti-PD-L1 antibody is an ISVD specific for PD-L1. In some embodiments, the reference anti-PD-L1 antibody comprises a heavy chain variable domain comprising an amino acid sequence as set forth in any one of SEQ ID NO: 6, 10, 12, 13, 14 and 15. In some embodiments, the reference anti-PD-L1 antibody comprises a heavy chain variable domain comprising an amino acid sequence as set forth in SEQ ID NO: 6.

In some embodiments, the ISVD specific for PD-L1 comprises a heavy chain CDR3 comprising an amino acid sequence as set forth in SEQ ID NO: 1. In some embodiments, the ISVD specific for PD-L1 comprises a heavy chain CDR3 comprising an amino acid sequence as set forth in any one of SEQ ID NO: 5 and 9.

In some embodiments, the ISVD specific for PD-L1 comprises a heavy chain CDR1 comprising an amino acid sequence as set forth in SEQ ID NO: 2. In some embodiments, the ISVD specific for PD-L1 comprises a heavy chain CDR1 comprising an amino acid sequence as set forth in any one of SEQ ID NO: 3 and 7.

In some embodiments, the ISVD specific for PD-L1 comprises a heavy chain CDR2 comprising an amino acid sequence as set forth in any one of SEQ ID NO: 4, 8 and 11.

In some embodiments, the ISVD specific for PD-L1 comprises a heavy chain variable domain comprising an amino acid sequence as set forth in any one of SEQ ID NO: 6, 10, 12, 13, 14 and 15. In some embodiments, the ISVD specific for PD-L1 comprises a heavy chain variable domain comprising an amino acid sequence as set forth in SEQ ID NO: 6.

In some embodiments, the ISVD specific for CTLA4 is capable of specifically binding to human CTLA4.

In some embodiments, the ISVD specific for CTLA4 is capable of blocking binding of CTLA4 to CD80.

In some embodiments, the ISVD specific for CTLA4 is capable of blocking binding of CTLA4 to CD86.

In some embodiments, the ISVD specific for CTLA4 cross-competes for binding to CTLA4 with a reference anti-CTLA4 antibody, the reference anti-CTLA4 antibody comprises a heavy chain CDR3 comprising an amino acid sequence as set forth in SEQ ID NO: 19. In some embodiments, the reference anti-CTLA4 antibody comprises a heavy chain CDR1 comprising an amino acid sequence as set forth in SEQ ID NO: 17. In some embodiments, the reference anti-CTLA4 antibody comprises a heavy chain CDR2 comprising an amino acid sequence as set forth in SEQ ID NO: 16. In some embodiments, the reference anti-CTLA4 antibody comprises a heavy chain CDR2 comprising an amino acid sequence as set forth in any one of SEQ ID NO: 18, 21 and 23. In some embodiments, the reference anti-CTLA4 antibody is an ISVD specific for CTLA4. In some embodiments, the reference anti-CTLA4 antibody comprises a heavy chain variable domain comprising an amino acid sequence as set forth in any one of SEQ ID NO: 20, 22, and 24-32. In some embodiments, the reference anti-CTLA4 antibody comprises a heavy chain variable domain comprising an amino acid sequence as set forth in SEQ ID NO: 20.

In some embodiments, the ISVD specific for CTLA4 comprises a heavy chain CDR3 comprising an amino acid sequence as set forth in SEQ ID NO: 19.

In some embodiments, the ISVD specific for CTLA4 comprises a heavy chain CDR1 comprising an amino acid sequence as set forth in SEQ ID NO: 17.

In some embodiments, the ISVD specific for CTLA4 comprises a heavy chain CDR2 comprising an amino acid sequence as set forth in SEQ ID NO: 16. In some embodiments, the ISVD specific for CTLA4 comprises a heavy chain CDR2 comprising an amino acid sequence as set forth in any one of SEQ ID NO: 18, 21 and 23.

In some embodiments, the ISVD specific for CTLA4 comprises a heavy chain variable domain comprising an amino acid sequence as set forth in any one of SEQ ID NO: 20, 22, and 24-32. In some embodiments, the ISVD specific for CTLA4 comprises a heavy chain variable domain comprising an amino acid sequence as set forth in SEQ ID NO: 20.

In some embodiments, the dimer of the present disclosure is a homodimer.

In some embodiments, the linker comprised in the dimer of the present disclosure comprises an amino acid sequence as set forth in any one of SEQ ID NO: 33-34.

In some embodiments, one or both of the two polypeptide chains of the dimer comprises an amino acid sequence as set forth in any one of SEQ ID NOs: 40-43, 46, 48 and 50. In some embodiments, one or both of the two polypeptide chains of the dimer comprises an amino acid sequence as set forth in SEQ ID NO: 40.

In some embodiments, the dimer of the present disclosure is capable of blocking binding of PD-L1 to PD-1.

In some embodiments, the dimer of the present disclosure is capable of blocking binding of PD-L1 to CD80.

In some embodiments, the dimer of the present disclosure is capable of blocking binding of CTLA4 to CD80.

In some embodiments, the dimer of the present disclosure is capable of blocking binding of CTLA4 to CD86.

In another aspect, the present disclosure provides an immunoconjugate, comprising the dimer of the present disclosure.

In another aspect, the present disclosure provides an isolated nucleic acid or isolated nucleic acids encoding the dimer of the present disclosure.

In another aspect, the present disclosure provides a vector or vectors comprising the isolated nucleic acid or isolated nucleic acids according to the present disclosure In another aspect, the present disclosure provides an isolated host cell comprising the isolated nucleic acid or isolated nucleic acids according to the present disclosure.

In another aspect, the present disclosure provides a method for producing the dimer or the immunoconjugate of the present disclosure. The method may comprise (i) culturing the host cell of the present disclosure under conditions to effect expression and formation of the dimer, and (ii) harvesting the dimer formed.

In another aspect, the present disclosure provides a pharmaceutical composition comprising an effective amount of the dimer of the present disclosure, the immunoconjugate of the present disclosure, and optionally a pharmaceutically acceptable excipient.

In another aspect, the present disclosure provides the dimer of the present disclosure, the immunoconjugate of the present disclosure, or the pharmaceutical composition of the present disclosure, for use in the treatment of a disease in a subject in need thereof. The disease may be a cancer.

In another aspect, the present disclosure provides use of the dimer or the immunoconjugate of the present disclosure in the preparation of a medicament for treating a cancer in a subject in need thereof.

In another aspect, the present disclosure provides a method for treating a cancer in a subject in need thereof, comprising administering to the subject an effective amount of the dimer or the immunoconjugate of the present disclosure.

In another aspect, the present disclosure provides a method for blocking binding of CD80 and/or CD86 to CTLA4, comprising administering the dimer or the immunoconjugate of the present disclosure.

In another aspect, the present disclosure provides a method for blocking binding of PD1 and/or CD80 to PD-L1, comprising administering the dimer or the immunoconjugate of the present disclosure.

In another aspect, the present disclosure provides a method for stimulating secretion of IL-2 by immune cells, comprising administering to the immune cells the dimer or the immunoconjugate of the present disclosure.

In another aspect, the present disclosure provides a method for enhancing an immune response in a subject, comprising administering to the subject the dimer or the immunoconjugate of the present disclosure.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are employed, and the accompanying drawings (also "figure" and "FIG." herein), of which:

DETAILED DESCRIPTION OF THE INVENTION

Figure 1:
FIG. 1 illustrates examples of the dimers of the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "immunoconjugate," as used herein, generally refers to a proteinaceous molecule formed by a conjugation of one or more immunoglobulin-related molecules or a fragment thereof to one or more additional molecules. The additional molecule may be the same as the immunoglobulin-related molecule or its fragment. In some cases, the additional molecule may be different from the immunoglobulin-related molecule or its fragment. The one or more additional molecules may be the same or may be different from each other. For example, the additional molecule may be a target binding moiety and/or an effector moiety, such as a toxin or a signaling molecule.

The term "homology," "homologous" or "sequence identity," as used herein, generally refers to sequence similarity or interchangeability between two or more polynucleotide sequences or between two or more polypeptide sequences. When using a program (e.g. Emboss Needle or BestFit) to determine sequence identity, similarity or homology between two different amino acid sequences, the default settings may be used, or an appropriate scoring matrix, such as blosum45 or blosum80, may be selected to optimize identity, similarity or homology scores. In some embodiments, polynucleotides that are homologous are those which hybridize under stringent conditions and have at least 60%, at least 65%, at least 70%, at least 80%, at least 90%, at least 95%, at least 97%, at least 98%, at least 99%, and even 100% sequence identity with a reference sequence. Polypeptides that are homologous may have a sequence identity of at least 80%, or at least 90%, or at least 95%, or at least 97%, or at least 98%, or at least 99% with each other when sequences of comparable length are optimally aligned.

The term "percent (%) sequence identity," as used in the context of polypeptide sequences identified herein, generally refers to the percentage of amino acid residues or nucleotides in a query sequence that are identical with the amino acid residues or nucleotides of a second, reference polypeptide sequence or a portion thereof, after aligning the sequences and introducing gaps, if necessary, to achieve the maximum percent sequence identity, and not considering any conservative substitutions as part of the sequence identity. Alignment for purposes of determining percent amino acid/nucleotide sequence identity can be achieved in various ways that are within the skill in the art, for instance, using publicly available computer software such as BLAST, BLAST-2, ALIGN, NEEDLE or Megalign (DNASTAR) software. Those skilled in the art can determine appropriate parameters for measuring alignment, including any algorithms needed to achieve maximal alignment over the full length of the sequences being compared. Percent identity may be measured over the length of an entire defined polypeptide/polynucleotide sequence, or may be measured over a shorter length, for example, over the length of a fragment taken from a larger, defined polypeptide/polynucleotide sequence. It is understood that any fragment length supported by the sequences shown herein, in the tables, figures or Sequence Listing, may be used to describe a length over which percentage identity may be measured.

The term "bispecific antibody," as used herein, generally refers to an antibody having the capacity to bind to two distinct epitopes either on a single antigen or two different antigens.

The term "PD-L1," as used herein, generally refers to the Programmed Death Ligand 1 protein, its functional variant and/or its functional fragments. PD-L1 is also known as cluster of differentiation 274 (CD274) or B7 homolog 1 (B7-H1), and is a protein encoded by the CD274 gene (in human). PD-L1 binds to its receptor, programmed cell death protein 1 (PD-1), which is expressed in activated T cells, B cells, and macrophages (Ishida et al., 1992 EMBO J, 11:3887-3395; Okazaki et al., Autoimmune dilated cardiomyopathy in PD-1 receptor-deficient mice. *Science,* 2001; 291: 319-22). The complexation of PD-L1 and PD-1 exerts immunosuppressive effects by inhibiting T cell proliferation and cytokine production of IL-2 and IFN-γ (Freeman et al., Engagement of PD-1 immunoinhibitory receptor by a novel B7 family member leads to negative regulation of lymphocyte activation, *J. Exp.Med.* 2000, 192:1027-1034; Carter et al., PD-1: PD-L inhibitory pathway affects both CD4(+) and CD8(+) T cells and is overcome by IL-2. *Eur. J. Immunol.* 2002, 32:634-643). For example, the term "PD-L1" may comprise a polypeptide or a fragment thereof having at least about 85% amino acid sequence identity to NCBI Accession No. Q9NZQ7 and that specifically binds PD1. The term PD-L1 comprises the entire PD-L1 ligand, soluble PD-L1 ligand, and fusion proteins comprising a functionally active portion of PD-L1 ligand covalently linked to a second moiety, e.g., a protein domain. Also included within the definition of PD-L1 are variants which vary in amino acid sequence from naturally occurring PD-L1 but which retain the ability to specifically bind to the receptor PD1. Further included within the definition of PD-L1 are variants which enhance the biological activity of PD1. PD-L1 sequences are known in the art and are provided, for example, at GenBank Accession Numbers 29126. The term "PD-L1" as used herein comprises human PD-L1 (hPD-L1), variants, isoforms, and species homologs of hPD-L1, and analogs having at least one common epitope with hPD-L1. For example, the term "PD-L1" also encompasses PD-L1 from other species, such as other mammals, for example, rat, mouse, rabbit, non-human primate, pig, or bovine. The complete hPD-L1 sequence can be found under GenBank Accession No. 29126.

The term "N-terminal IgV domain of human PD-L1," as used herein, generally refers to an extracellular domain of human PD-L1 located in its N-terminus. The term "N-terminal IgV domain of human PD-L1" may also refer to epitopes within said domain. The N-terminal IgV domain of the human PD-L1 protein (including the signal peptide) may comprise an amino acid sequence as set forth in SEQ ID NO: 64.

The term "CTLA4," as used herein, generally refers to the Cytotoxic T-Lymphocyte-Associated protein 4, its functional variant and/or its functional fragments. CTLA4 is an immunoinhibitory receptor belonging to the CD28 family. CTLA4 is expressed exclusively on T cells (CD 4$^+$ and CD 8$^+$ cells) in vivo, and binds to two ligands, CD80 and CD86 (also called B7-1 and B7-2, respectively). For example, the term "CTLA4" may comprise a polypeptide or a fragment thereof having at least about 85% amino acid sequence identity to NCBI Accession No. AAL07473.1 and that specifically binds to CD80 and/or CD86. The term "CTLA4" comprises the entire CTLA4 receptor, its extracellular domain, and fusion proteins comprising a functionally active portion of CTLA4 covalently linked to a second moiety, e.g., a protein domain. Also included within the definition of CTLA4 are variants which vary in amino acid sequence from naturally occurring CTLA4 but which retain the ability to specifically bind to the ligand CD80 and/or CD86. CTLA4 sequences are known in the art and are provided, for example, at GenBank Accession No. 1493. The term "CTLA4" as used herein comprises human CTLA4 (hCTLA4), variants, isoforms, and species homologs of hCTLA4, and analogs having at least one common epitope with hCTLA4. For example, the term "CTLA4" also encompasses CTLA4 from other species, such as other mammals, for example, rat, mouse, rabbit, non-human primate, pig, or bovine. The complete hCTLA4 sequence can be found under GenBank Accession No. 1493.

The term "antibody Fc subunit," as used herein, generally refers to a component of an antibody Fc domain. For example, an antibody Fc domain may be formed by two or more members, and each member may be considered as one Fc subunit. The term "Fc domain," as used herein, generally refers to an Fc part or Fc fragment of an antibody heavy chain. For example, it may refer to the carboxyl terminal portion of an immunoglobulin heavy chain constant region, or an analog or portion thereof capable of binding an Fc receptor. As is known, each immunoglobulin heavy chain constant region comprises four or five domains. The domains are named sequentially as follows: CH1-hinge-CH2-CH3(—CH4). CH4 is present in IgM, which has no hinge region. The Fc domain or Fc subunit useful in the present disclosure may comprise a CH3 domain. For example, the Fc domain or Fc subunit may comprise a CH2 domain and a CH3 domain. In some embodiments, the Fc domain or Fc subunit may also comprise an immunoglobulin hinge region. For example, the Fc domain or Fc subunit may comprise or consist of, from N-terminus to C-terminus, a CH2 domain and a CH3 domain. In another example, the Fc domain or Fc subunit may comprise or consist of, from N-terminus to C-terminus, an immunoglobulin hinge region, a CH2 domain and a CH3 domain. Amino acid residue positions within the Fc domain or Fc subunit may be determined according to Kabat, E. A. et al., (1991) Sequences of Proteins of Immunological Interest, 5th ed., NIH Publication No. 91-3242.

The term "Fc domain", as used herein, generally refers to a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include human IgG1, IgG2 (IgG2A, IgG2B), IgG3 and IgG4.

Unless indicated otherwise herein, the numbering of the residues in an immunoglobulin chain is that of the EU index as in Kabat et al., Sequences of Proteins of Immunological Interest, 5$^{th}$ Ed. Public Health Service, National Institutes of Health, Bethesda, Md. (1991). The "EU index as in Kabat" refers to the residue numbering of the human IgG1 EU antibody.

The term "dimer," as used herein, generally refers to a macromolecular complex formed by two, usually non-covalently bound, monomer units. Each monomer unit may be a macromolecule, such as a polypeptide chain or a polynucleotide. The term "homodimer," as used herein, generally refers to a dimer composed of or formed by two substantially identical monomers, such as two substantially identical polypeptide chains. In some cases, the two monomers of a homodimer may be different at one or more regions or positions, however, such difference does not cause significant alteration in the function or structure of the monomer. For example, one of ordinary skills in the art would consider the difference between the two monomers to be of little or no biological and/or statistical significance within the context of the biological characteristic considered in the present disclosure. The structural/compositional difference between said two monomers may be, for example, less than about 50%, less than about 40%, less than about 30%, less than about 20%, less than about 10%, less than about 5%, or less.

The term "fused" or "fusion," as used herein, generally refers the covalent linkage between two polypeptides. The polypeptides are typically joined via a peptide bond, either directly to each other or via an amino acid linker. Optionally, the peptides can be joined via non-peptide covalent linkages known to those of skill in the art.

The term "fusion protein" as used herein, generally refers to a polypeptide that comprises, or alternatively consists of, an amino acid sequence of a polypeptide fused directly or indirectly (e.g., via a linker) to an amino acid sequence of a heterologous polypeptide (i.e., a polypeptide unrelated to the former polypeptide or the domain thereof).

The term "immunoglobulin single variable domain (ISVD)," as used herein, generally refers to antigen-binding domains or fragments such as VHH domains or VH or VL domains, respectively. The terms antigen-binding molecules or antigen-binding protein are used interchangeably and include also the term Nanobodies. The immunoglobulin single variable domains further are light chain variable domain sequences (e.g., a VL-sequence), or heavy chain variable domain sequences (e.g., a VH-sequence); more specifically, they can be heavy chain variable domain sequences that are derived from a conventional four-chain antibody or heavy chain variable domain sequences that are derived from a heavy chain antibody. Accordingly, the immunoglobulin single variable domains can be domain antibodies, or immunoglobulin sequences that are suitable for use as domain antibodies, single domain antibodies, or immunoglobulin sequences that are suitable for use as single domain antibodies, "dAbs," or immunoglobulin sequences that are suitable for use as dAbs, or Nanobodies, including but not limited to VHH sequences. The immunoglobulin single variable domain comprises fully human, humanized, otherwise sequence optimized or chimeric immunoglobulin sequences. The immunoglobulin single variable domain and structure of an immunoglobulin single variable domain can be considered—without however being limited thereto—to be comprised of four framework regions or "FRs," which are referred to in the art and herein as "Framework region 1" or "FR1"; as "Framework region 2" or "FR2"; as "Framework region 3" or "FR3"; and as "Framework region 4" or "FR4," respectively; which framework regions are interrupted by three complementary determining regions or "CDRs," which are referred to in the art as "Complementarity Determining Region 1" or "CDR1"; as "Complementarity Determining Region 2" or "CDR2"; and as "Complementarity Determining Region 3" or "CDR3," respectively.

The term "humanized," as used herein, generally refers to an antibody or a fragment thereof, in which some, most or all of the amino acids outside the CDR domains of a non-human antibody are replaced with corresponding amino acids derived from human immunoglobulins. For example, in a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to its specific antigen/epitope. A humanized antibody may retain an antigenic specificity similar to that of the original antibody.

The term "epitope" or "antigenic determinant," as used herein, generally refers to a site on an antigen to which an antibody binds. Epitopes can be formed both from contiguous amino acids (linear epitope) or noncontiguous amino acids juxtaposed by tertiary folding of a protein (conformational epitopes). Epitopes formed from contiguous amino acids are typically retained on exposure to denaturing solvents whereas epitopes formed by tertiary folding are typically lost on treatment with denaturing solvents. An epitope typically comprises at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

The term "conformational epitope," as used herein, generally refers to noncontiguous amino acid residues of the antigen (such as the PD-L1 antigen) that are juxtaposed by tertiary folding of a protein. These noncontiguous amino acid residues may come together on the surface when the polypeptide chain folds to form the native protein. The conformation epitope contains, but is not limited to, the functional epitope.

The term "functional epitope," as used herein, generally refers to amino acid residues of an antigen that contribute energetically to the binding of an antibody, i.e. forming an "energetic epitope". Mutation of any one of the energetically contributing residues of the antigen to alanine will disrupt the binding of the antibody such that the relative $K_D$ ratio ($K_D$ mutant/$K_D$ wildtype) of the antibody may be e.g., greater than 2 folds, such as greater than 3 folds, greater than 4 folds, greater than 6 folds, greater than 10 folds, greater than 20 folds, greater than 30 folds, greater than 40 folds, greater than 50 folds, greater than 60 folds, greater than 70 folds, greater than 80 folds, greater than 90 folds, greater than 100 folds, greater than 150 folds, greater than 200 folds, or more.

The term "extracellular domain," as used herein, generally refers to part of a protein (e.g., a membrane protein, such as a receptor) protruding from the outer membrane of a cell organelle and/or a cell. If the polypeptide chain crosses the bilayer several times, the extracellular domain comprises loops entwined through the membrane. An extracellular domain may recognize and respond to a specific ligand.

The term "linker," as used herein, generally refers to a synthetic amino acid sequence that connects or links two polypeptide sequences, e.g., that links two polypeptide domains. A linker may connect two amino acid sequences via peptide bonds. In some embodiments, a linker of the present disclosure connects a biologically active moiety to a second moiety in a linear sequence. For example, a peptide linker may be non-immunogenic and flexible, such as those comprising serine and glycine sequences or repeats of Ala-Ala-Ala. Depending on the particular construct of the dimer, a peptide linker may comprise, e.g., 3-30 (such as at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30) amino acid residues.

The term "N-terminal" may be used interchangeably with "N-terminus," and as used herein, they generally refer to the amino terminus/end of a polypeptide chain.

The term "C-terminal" may be used interchangeably with "C-terminus," and as used herein, they generally refer to the carboxyl terminus/end of a polypeptide chain.

The term "PBMC cells," as used herein, generally refers to peripheral blood mononuclear cells, which may comprise lymphocytes (T cells, B cells, NK cells) and monocytes. These cells can be extracted from whole blood using Ficoll (a hydrophilic polysaccharide that separates layers of blood), and/or gradient centrifugation (which may separate the blood into a top layer of plasma, followed by a layer of PBMCs and a bottom fraction of polymorphonuclear cells (such as neutrophils and eosinophils) and erythrocytes).

The term "effective amount," as used herein, generally refers to a dose sufficient to provide concentrations high enough to impart a beneficial effect on the recipient thereof. The specific therapeutically effective dose level for any particular subject may depend upon a variety of factors including the disorder being treated, the severity of the disorder, the activity of the specific component, the route of administration, the rate of clearance, the duration of treatment, the age, body weight, sex, diet, and general health of the subject, and other related factors.

The term "pharmaceutically acceptable excipient," as used herein, generally refers to any and all solvents, dispersion media, coatings, isotonic and absorption delaying agents, etc., that are compatible with pharmaceutical administration.

The term "host cell," as used herein, generally refers to an individual cell, a cell line or cell culture which can be or has been a recipient for the subject plasmids or vectors, comprise the isolated nucleic acid of the present disclosure, or express the dimer of the present disclosure. Host cells may include progeny of a single host cell. The progeny may not necessarily be completely identical (in morphology or in genomic of total DNA complement) to the original parent cell due to natural, accidental, or deliberate mutation. A host cell may include cells transfected in vitro with a vector of the present disclosure. A host cell may be a bacterial cell (e.g., E. coli), a yeast cell or other eukaryotic cells, e.g., a COS cell, a Chinese hamster ovary (CHO) cell, a HeLa cell, a HEK293 cell, a COS-1 cell, an NSO cell, or a myeloma cell. In some embodiments, a host cell is a mammalian cell. In some embodiments, the mammalian cell is a HEK293 cell.

The term "vector," as used herein, generally refers to a nucleic acid molecule capable of self-replicating in an appropriate host, which transfers an inserted nucleic acid molecule into and/or between host cells. The term may include vectors that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions. An "expression vector" is a polynucleotide which, when introduced into an appropriate host cell, can be transcribed and translated into a polypeptide(s). An "expression system" usually connotes a suitable host cell comprising an expression vector that can function to yield a desired expression product.

The term "isolated nucleic acid," as used herein, generally refers to an isolated form of nucleotides of any length, either deoxyribonucleotides or ribonucleotides, or analogs thereof, isolated from its native environment, or that is artificially synthesized.

The term "cancer," as used herein, generally refers to tumor growth or metastasis, by any clinically measurable degree. The cancer can be a solid tumor, a hematologic cancer, or a lymphoma. For example, the cancer may be selected from lung cancer (such as non-small-cell lung cancer), breast cancer (such as Triple-Negative Breast Cancer), kidney cancer (such as renal cell carcinoma), melanoma, cervical cancer, uterus cancer, pancreatic cancer, peritoneal carcinoma, ovarian cancer and colon cancer. The cancer may be advanced or metastatic cancer.

The term "IL-2" or "IL2," as used herein, generally refers to Interleukin-2, its functional variant and/or its functional fragments. The term IL2 encompasses human IL-2 (hIL-2), as well as IL-2 from other species, such as other mammals, for example, rat, mouse, rabbit, non-human primate, pig, or bovine. hIL-2 is as described by GenBank Submission, NCBI; Accession No. P60568. The term "IL-2" may also refer to a polypeptide capable of stimulating proliferation of hIL-2 dependent cytolytic and helper T-cell lines, as set forth in the standard assays of Gillis, S., et al., J. Immunol. (1978) 120:2027-2032 and of Watson, J., J. Exp. Med. (1979) 150:1510-1519.

The term "immune cells," as used herein, generally refers to the cells of the immune system. Immune cells may include cells that are involved in protecting the body against infectious disease and/or foreign invaders. Immune cells may comprise cells of the innate immune system and cells of the adaptive immune system. Immune cells may comprise leukocytes or leucocytes, such as neutrophils, eosinophils, basophils, lymphocytes, and monocytes. Further subtypes can be classified; for example, among lymphocytes, there are B cells, T cells, and Natural Killer (NK) cells.

The term "subject," as used herein, generally refers to a human or non-human animal, including, but not limited to, a cat, dog, horse, pig, cow, sheep, goat, rabbit, mouse, rat, or monkey.

The term "about," as used herein, generally refers to a variation that is within a range of normal tolerance in the art, and generally means within ±10%, such as within 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The term "specifically binds to" or "is specific for," as used herein, generally refers to measurable and reproducible inter actions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant ($K_D$) of $<1\times10^{-6}$M, $<1\times10^{-7}$M, $<1\times10^{-8}$M, $<1\times10^{-9}$M, or $<1\times10^{-10}$M. In certain embodiments, an antibody specifically binds to an epitope on a protein that is conserved among the protein from different species. In another embodiment, specific binding can include, but does not require exclusive binding.

The term "antibody," as used herein, generally refers to an immunoglobulin or a fragment or a derivative thereof, and encompasses any polypeptide comprising an antigen-binding site, regardless whether it is produced in vitro or in vivo. The term comprises, but is not limited to, polyclonal, monoclonal, monospecific, polyspecific, non-specific, humanized, single-chain, chimeric, synthetic, recombinant, hybrid, mutated, and grafted antibodies. Unless otherwise modified by the term "intact," as in "intact antibodies," for the purposes of this disclosure, the term "antibody" also comprises antibody fragments such as Fab, F(ab')$_2$, Fv, scFv, Fd, dAb, and other antibody fragments that retain antigen-binding function, i.e., the ability to bind, for example, CTLA-4, or PD-L1 specifically. Typically, such fragments would comprise an antigen-binding domain.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see e.g., Basic and Clinical Immunology, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the CH sequence and function, e.g., humans express the following subclasses: IgG1, IgG2A, IgG2B, IgG3, IgG4, IgA1 and IgK1.

The term "polypeptide chain," as used herein, generally refers to a macromolecule comprising two or more covalently connected peptides. The peptides within a polypeptide chain may be connected with each other via a peptide bond. Each polypeptide chain may comprise one N-terminus or amino terminus and one C-terminus or carboxy terminus.

The term "CD80," as used herein, generally refers to a ligand for CD28/CTLA4, also known as B7.1, its functional variant and/or its functional fragments. CD80 is generally expressed on the surface of professional antigen presenting cells (APC). For example, the term "CD80" may comprise a polypeptide or a fragment thereof having at least about 85% amino acid sequence identity to NCBI Accession No.P33681 and that specifically binds CTLA4. Also included within the definition of CD80 are variants which vary in amino acid sequence from naturally occurring CD80 but which retain the ability to specifically bind to CTLA4. Further included within the definition of CD80 are variants which enhance the biological activity of CTLA4. CD80 sequences are known in the art and are provided, for example, at GenBank Accession Numbers P33681. The term "CD80" as used herein comprises human CD80 (hCD80), variants, isoforms, and species homologs of hCD80, and analogs having at least one common epitope with hCD80. For example, the term "CD80" also encompasses CD80 from other species, such as other mammals, for example, rat, mouse, rabbit, non-human primate, pig, or bovine. The complete hCD80 sequence can be found under GenBank Accession No. P33681.

The term "CD86," as used herein, generally refers to a ligand for CD28/CTLA4, also known as B7.2, its functional variant and/or its functional fragments. CD86 is generally expressed on the surface of professional antigen presenting cells (APC). For example, the term "CD86" may comprise a polypeptide or a fragment thereof having at least about 85% amino acid sequence identity to NCBI Accession No. P42081 and that specifically binds CTLA4. Also included within the definition of CD86 are variants which vary in amino acid sequence from naturally occurring CD86 but which retain the ability to specifically bind to CTLA4. Further included within the definition of CD86 are variants which enhance the biological activity of CTLA4. CD86 sequences are known in the art and are provided, for example, at GenBank Accession Numbers U04343. The term "CD86" as used herein comprises human CD86 (hCD86), variants, isoforms, and species homologs of hCD86, and analogs having at least one common epitope with hCD86. For example, the term "CD86" also encompasses CD86 from other species, such as other mammals, for example, rat, mouse, rabbit, non-human primate, pig, or bovine. The complete hCD86 sequence can be found under GenBank Accession No. U04343.

The term "PD1," as used herein, generally refers to programmed death-1 receptor, also known as CD279, its functional variant and/or its functional fragments. PD1 is generally expressed on T cells, B cells, natural killer T cells, activated monocytes and dendritic cells (DCs). PD1 may bind to its ligands PD-L1 and PD-L2. For example, the term "PD1" may comprise a polypeptide or a fragment thereof having at least about 85% amino acid sequence identity to NCBI Accession No P42081 and that specifically binds PD-L1. Also included within the definition of PD1 are variants which vary in amino acid sequence from naturally occurring PD1 but which retain the ability to specifically bind to PD-L1. Further included within the definition of PD1 are variants which enhance the biological activity of PD-L1. PD1 sequences are known in the art and are provided, for example, at GenBank Accession Number Q15116.3. The term "PD1" as used herein comprises human PD1 (hPD1), variants, isoforms, and species homologs of hPD1, and analogs having at least one common epitope with hPD1. For example, the term "PD1" also encompasses PD1 from other species, such as other mammals, for example, rat, mouse, rabbit, non-human primate, pig, or bovine. The complete hPD1 sequence can be found under GenBank Accession No. Q15116.3.

The term "blocking", as used herein, generally refers to an inhibition or reduction of the binding activity between a molecule and its specific binding partner, such as between a ligand and its specific receptor.

The term "blocking antibody" and "antagonist antibody" are used interchangeably herein and generally refers to an antibody that inhibits or reduces a biological activity of the antigen it binds to. In some embodiments, blocking antibodies or antagonist antibodies substantially or completely inhibit the biological activity of the antigen. The PD-L1 specific ISVD or the CTLA4 specific ISVD of the present disclosure may be blocking or antagonistic ISVDs. For example, the PD-L1 specific ISVD of the present disclosure may block the interaction between PD-L1 and its receptor PD-1, and thus the signaling through PD-1 so as to restore a functional response by T-cells from a dysfunctional state to antigen stimulation. The CTLA4 specific ISVD of the present disclosure may block the interaction between CTLA4 and CD80/CD86, and thus the signaling through CTLA4 so as to restore a functional response by T-cells from a dysfunctional state to antigen stimulation.

The term "cross-competes for binding", "cross-competition", "cross-block", "cross-blocked" and "cross-blocking" are used interchangeably herein and generally refers to the ability of an antibody or fragment thereof to interfere with the binding directly or indirectly through allosteric modulation of another antibody of the invention (e.g., the PD-L1 specific ISVD or the CTLA4 specific ISVD of the present disclosure) to the target/antigen (e.g., PD-L1 or CTLA4, respectively). The extent to which an antibody or fragment thereof is able to interfere with the binding of another to the target, and therefore whether it can be said to cross-block or cross-compete according to the invention, can be determined using competition binding assays. One particularly suitable quantitative cross-competition assay uses a FACS-based or an AlphaScreen-based approach to measure competition between the labelled (e.g. His tagged, biotinylated or radioactive labelled) an antibody or fragment thereof and the other an antibody or fragment thereof in terms of their binding to the target. In general, a cross-competing antibody or fragment thereof is for example one which will bind to the target in the cross-competition assay such that, during the assay and in the presence of a second antibody or fragment thereof, the recorded displacement of the immunoglobulin single variable domain or polypeptide according to the invention is up to 100% (e.g. in FACS based competition assay) of the maximum theoretical displacement (e.g. displacement by cold (e.g. unlabeled) antibody or fragment thereof that needs to be cross-blocked) by the to be tested potentially cross-blocking antibody or fragment thereof that is present in a given amount. Preferably, cross-competing antibodies or fragments thereof have a recorded displacement that is between 10% and 100%, such as between 50% to 100%.

The term "substantially reduced," or "substantially different," as used herein, generally refers to a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., KD values). The difference between said two values is, for example, greater than about 10%, greater than about 20%, greater than about 30%, greater than about 40%, and/or greater than about 50% as a function of the value for the reference/comparator molecule.

The term "substantially similar" or "substantially the same," as used herein, generally refers to a sufficiently high degree of similarity between two numeric values (for example, one associated with a molecule of the present disclosure and the other associated with a reference/comparator molecule), such that one of skill in the art would consider the difference between the two values to be of little or no biological and/or statistical significance within the context of the biological characteristic measured by said values {e.g., $K_D$ values). The difference between said two values is, for example, less than about 50%, less than about 40%, less than about 30%, less than about 20%, and/or less than about 10% as a function of the reference/comparator value.

The term "enhancing immune response," as used herein, generally refers to induce, cause or stimulate an immune cell (such as T-cell, or PBMC cell) to have a sustained or amplified biological function, or renew or reactivate exhausted or inactive immune cell. Examples of enhancing immune cell function include: increased secretion of IL-2 by PBMC cells, increased proliferation, increased antigen responsiveness (e.g., viral or pathogen clearance) relative to such levels before the intervention. The level of enhancement may be at least 30%, e.g., at least 40%, at least 50%, at least 60%, at least 70%, at least 80%, at least 90%, at least 100%, at least 120%, at least 150%, or at least 200%. The manner of measuring this enhancement is known to one of ordinary skill in the art.

The term "variable region" or "variable domain" of an antibody, as used herein, generally refers to the amino-terminal domains of the heavy or light chain of an antibody. The variable domains of the heavy chain and light chain may be referred to as "VH" and "VL", respectively. These domains are generally the most variable parts of the antibody (relative to other antibodies of the same class) and contain the antigen binding sites.

The term "variable", as used herein, generally refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (CDRs or HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies (see Kabat et al, Sequences of Immunological Interest, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "CDR," "HVR," or "HV," as used herein, generally refers to the regions of an antibody variable domain which are hypervariable in sequence and/or form structurally defined loops. Generally, antibodies comprise six CDRs; three in the VH (HCDR1, HCDR2, HCDR3), and three in the VL (LCDR1, LCDR2, LCDR3). The ISVD of the present disclosure may only comprise 3 CDRs (e.g., in the VH, HCDR1, HCDR2 and HCDR3). In native antibodies, HCDR3 and LCDR3 display the most diversity of the six CDRs, and HCDR3 in particular is believed to play a unique role in conferring fine specificity to antibodies. See, e.g., Xu et al, Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al, Nature Struct. Biol. 3:733-736 (1996).

A number of CDR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk, J. Mol. Biol. 196:901-917 (1987)). The AbM CDRs represent a compromise between the Kabat HVRs and Chothia structural loops, and are used by Oxford Molecular's AbM antibody modeling software.

The "contact" CDRs are based on an analysis of the available complex crystal structures. The residues from each of these CDRs are noted below:

| Loop | Kabat | AbM | Chothia | Contact |
| --- | --- | --- | --- | --- |
| LCDR1 | L24-L34 | L24-L34 | L26-L32 | L30-L36 |
| LCDR2 | L50-L56 | L50-L56 | L50-L52 | L46-L55 |
| LCDR3 | L89-L97 | L89-L97 | L91-L96 | L89-L96 |
| HCDR1(Kabat Numbering) | H31-H35B | H26-H35B | H26-H32 | H30-H35B |
| HCDR1 (Chothia Numbering) | H31-H35 | H26-H35 | H26-H32 | H30-H35 |
| HCDR2 | H50-H65 | H50-H58 | H53-H55 | H47-H58 |
| HCDR3 | H95-H102 | H95-H102 | H96-H101 | H93-H101 |

CDRs may comprise "extended CDRs" as follows: 24-36 or 24-34 (LCDR1), 46-56 or 50-56 (LCDR2) and 89-97 or 89-96 (LCDR3) in the VL and 26-35 (HCDR1), 50-65 or 49-65 (HCDR2) and 93-102, 94-102, or 95-102 (HCDR3) in the VH. The variable domain residues are numbered according to Kabat et al., supra, for each of these definitions.

The expression "variable-domain residue-numbering as in Kabat" or "amino-acid-position numbering as in Kabat," and variations thereof, generally refers to the numbering system used for heavy-chain variable domains or light-chain variable domains of the compilation of dimer/polypeptide chain in Kabat et al., supra. The Kabat numbering of residues may be determined for a given polypeptide by alignment at regions of homology of the sequence of the polypeptide with a "standard" Kabat numbered sequence.

"Framework" or "FR" residues are those variable-domain residues other than the CDR residues as herein defined. A "human consensus framework" or "acceptor human framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, 5th Ed. Public Health Service, National Institutes of Health, Bethesda, Md. (1991). Examples include for the VL, the subgroup may be subgroup kappa I, kappa II, kappa III or kappa IV as in Kabat et al, supra. Additionally, for the VH, the subgroup may be subgroup I, subgroup II, or subgroup III as in Kabat et al., supra. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain preexisting amino acid sequence changes. In some embodiments, the number of pre-existing amino acid changes are 10 or less, 9 or less, 8 or less, 7 or less, 6 or less, 5 or less, 4 or less, 3 or less, or 2 or less.

In the present disclosure, an amino acid sequence or nucleotide sequence as set forth in a specific SEQ ID NO. also encompasses homologs or variants thereof having substantially the same function/property thereto. For example, a sequence having at least 90%, at least 91%, at least 92%, at least 93%, at least 94%, at least 95%, at least 96%, at least 97%, at least 98%, at least 99%, or higher sequence identity thereto; and/or a variant having one or more (e.g., a few, such as 1-10, 1-9, 1-8, 1-7, 1-6, 1-5, 1-4, 1-3, 1-2) amino acid or nucleotide addition, deletion or substitution.

Dimers, Immunoconjugates, Isolated Polynucleotides, Vectors and Host cells

In one aspect, the present disclosure provides a dimer. The dimer may be formed by two polypeptide chains, with each of the two polypeptide chains comprising an antibody Fc subunit. For example, the dimer may consist of two polypeptide chains with each polypeptide chain comprising an antibody Fc subunit, and the antibody Fc subunit of one polypeptide chain may associate with the antibody Fc subunit of the other polypeptide chain to form the dimer. In an example, the two polypeptide chains of the dimer do not fuse (e.g., via a peptide linker or by a peptide bond) with each other to become one single polypeptide chain.

The dimer may comprise two or more immunoglobulin single variable domains (ISVDs). For example, one polypeptide chain of the dimer may comprise two or more ISVDs, and the other polypeptide chain of the dimer does not comprise any ISVD. In another example, each of the two polypeptide chains may comprise one or more ISVDs. In yet another example, each of the two polypeptide chains may comprise two or more ISVDs.

At least one of the ISVDs may be specific for PD-L1, and at least one of the ISVDs may be specific for CTLA4. For example, one polypeptide chain of the dimer may comprise one or more ISVDs specific for PD-LI and one or more ISVDs specific for CTLA4, and the other polypeptide chain of the dimer does not comprise any ISVD. In another example, one polypeptide chain of the dimer may comprise one or more ISVDs specific for PD-L1, and the other polypeptide chain of the dimer may comprise one or more ISVDs specific for CTLA4. In another example, one polypeptide chain of the dimer may comprise one or more ISVDs specific for PD-L1 and one or more ISVDs specific for CTLA4, and the other polypeptide chain of the dimer may comprise one or more ISVDs specific for PD-L1 and/or one or more ISVDs specific for CTLA4.

The one or more ISVDs specific for PD-L1 may be identical or different. The one or more ISVDs specific for CTLA4 may be identical or different.

In some cases, the ISVD specific for PD-L1 does not comprise any antibody light chain CDR. In some cases, the ISVD specific for PD-L1 does not comprise any antibody light chain variable region. In some cases, the ISVD specific for PD-L1 does not comprise any antibody light chain or any fragment thereof. In some cases, the ISVD specific for PD-L1 comprises at least heavy chain CDR3. In some cases, the ISVD specific for PD-L1 comprises heavy chain CDR1. In some cases, the ISVD specific for PD-L1 comprises heavy chain CDR2. In some cases, the ISVD specific for PD-L1 comprises a heavy chain variable region. In some cases, the ISVD specific for PD-L1 is an anti-PD-L1 VHH. The ISVD specific for PD-L1 may be humanized.

In some cases, the ISVD specific for CTLA4 does not comprise any antibody light chain CDR. In some cases, the ISVD specific for CTLA4 does not comprise any antibody light chain variable region. In some cases, the ISVD specific for CTLA4 does not comprise any antibody light chain or any fragment thereof. In some cases, the ISVD specific for CTLA4 comprises at least heavy chain CDR3. In some cases, the ISVD specific for CTLA4 comprises heavy chain CDR1. In some cases, the ISVD specific for CTLA4 comprises heavy chain CDR2. In some cases, the ISVD specific for CTLA4 comprises a heavy chain variable region. In some cases, the ISVD specific for CTLA4 is an anti-CTLA4 VHH. The ISVD specific for CTLA4 may be humanized.

In some cases, at least one of the two polypeptide chains may comprise both an ISVD specific for PD-L1 and an ISVD specific for CTLA4. For example, one of the two polypeptide chains may comprise one or more ISVDs specific for PD-L1 and one or more ISVDs specific for CTLA4. In another example, each of the two polypeptide chains may comprise one or more ISVDs specific for PD-L1 and one or more ISVDs specific for CTLA4.

For one or both of the two polypeptide chains, the ISVD specific for PD-L1 may be fused to the ISVD specific for CTLA4, optionally via a linker. For example, in one or both of the two polypeptide chains, there may be one or more ISVDs specific for PD-L1, and one or more ISVDs specific for CTLA4. When two or more ISVDs specific for PD-LI are present in a single polypeptide chain, they may be fused to each other (e.g., directly or via a peptide linker), and one or more of them may further be fused to one or more ISVDs specific for CTLA4. When two or more ISVDs specific for CTLA4 are present in a single polypeptide chain, they may be fused to each other (e.g., directly or via a peptide linker), and one or more of them may further be fused to one or more ISVDs specific for PD-L1. One or more linkers (e.g., peptide linker) may be present between any two ISVDs, for example, between two ISVDs specific for PD-L1, between two ISVDs specific for CTLA4, or between one ISVD specific from PD-L1 and one ISVD specific for CTLA4.

For one or both of the two polypeptide chains, the ISVD specific for PD-L1 may be fused to the ISVD specific for CTLA4, optionally via a linker; and the ISVD specific for CTLA4 may in turn be fused to the antibody Fc subunit, optionally via a linker. For example, in a single polypeptide chain, the ISVD specific for PD-L1 may be fused to the ISVD specific for CTLA4 directly (e.g., in frame) or via a linker, and the ISVD specific for CTLA4 may be fused to the antibody Fc subunit directly (e.g., in frame) or via a linker. When there are more than one ISVDs specific for PD-L1 and/or more than one ISVDs specific for CTLA4 in a single polypeptide chain, the ISVDs specific for PD-L1 and the ISVDs specific for CTLA4 may be fused directly or via a linker to each other according to any order, and at least one ISVD specific for CTLA4 may be fused to the antibody Fc subunit directly (e.g., in frame) or via a linker. For example, for one or both of the two polypeptide chains, C terminus of the ISVD specific for PD-L1 may be fused to N terminus of the ISVD specific for CTLA4, optionally via a linker; and C terminus of the ISVD specific for CTLA4 may be fused to N terminus of the antibody Fc subunit, optionally via a linker. For example, in a single polypeptide chain, C terminus of one of the ISVDs specific for PD-L1 may be fused to N terminus of one of the ISVDs specific for CTLA4, either directly (e.g., in frame) or via a linker, and C terminus of one of the ISVDs specific for CTLA4 may be fused to N terminus of the antibody Fc subunit, either directly (e.g., in frame) or via a linker. In an example, when there are more than one ISVDs specific for PD-L1 and/or more than one ISVDs specific for CTLA4 in a single polypeptide chain, the ISVDs specific for PD-L1 and the ISVDs specific for CTLA4 may be fused directly or via a linker to each other according to any order, however, C terminus of at least one ISVD specific for PD-L1 may be fused to N terminus of at least one ISVD specific for CTLA4, either directly (e.g., in frame) or via a linker, and C terminus of at least one ISVD specific for CTLA4 may be fused to N terminus of the antibody Fc subunit, either directly (e.g., in frame) or via a linker.

For one or both of the two polypeptide chains, the ISVD specific for CTLA4 may be fused to the ISVD specific for PD-L1, optionally via a linker; and the ISVD specific for PD-L1 may in turn be fused to the antibody Fc subunit, optionally via a linker. For example, in a single polypeptide chain, the ISVD specific for CTLA4 may be fused to the ISVD specific for PD-L1 directly (e.g., in frame) or via a linker, and the ISVD specific for PD-L1 may be fused to the antibody Fc subunit directly (e.g., in frame) or via a linker. When there are more than one ISVDs specific for PD-L1 and/or more than one ISVDs specific for CTLA4 in a single polypeptide chain, the ISVDs specific for PD-L1 and the ISVDs specific for CTLA4 may be fused directly or via a linker to each other according to any order, and at least one ISVD specific for PD-L1 may be fused to the antibody Fc subunit directly (e.g., in frame) or via a linker. For example, for one or both of the two polypeptide chains, C terminus of the ISVD specific for CTLA4 may be fused to N terminus of the ISVD specific for PD-L1, optionally via a linker; and C terminus of the ISVD specific for PD-L1 may be fused to N terminus of the antibody Fc subunit, optionally via a linker. For example, in a single polypeptide chain, C terminus of one of the ISVDs specific for CTLA4 may be fused to N terminus of one of the ISVDs specific for PD-L1, either directly (e.g., in frame) or via a linker, and C terminus of one of the ISVDs specific for PD-L1 may be fused to N terminus of the antibody Fc subunit, either directly (e.g., in frame) or via a linker. In an example, when there are more than one ISVDs specific for PD-L1 and/or more than one ISVDs specific for CTLA4 in a single polypeptide chain, the ISVDs specific for PD-L1 and the ISVDs specific for CTLA4 may be fused directly or via a linker to each other according to any order, however, C terminus of at least one ISVD specific for CTLA4 may be fused to N terminus of at least one ISVD specific for PD-L1, either directly (e.g., in frame) or via a linker, and C terminus of at least one ISVD specific for PD-L1 may be fused to N terminus of the antibody Fc subunit, either directly (e.g., in frame) or via a linker.

The linker (e.g., a peptide linker) employed in the present application (e.g., as comprised by the dimer of the present application) may be a synthetic amino acid sequence that connects or links two polypeptide sequences, e.g., via peptide bonds. For example, the peptide linker may comprise 1-10 amino acids (e.g., 1, 2, 3, 4, 5, 6, 7, 8, 9, 10 or more amino acids), 1-15 amino acids (e.g., 1-10, 11, 12, 13, 14 or 15 amino acids), 1-20 amino acids (e.g., 1-15, 16, 17, 18, 19, or 20 amino acids), 1-30 amino acids or more (e.g., 1-20, 21, 22, 23, 24, 25, 26, 27, 28, 29, 30 or more amino acids). For example, the peptide linker may comprise an amino acid sequence as set forth in any of SEQ ID NO: 33-34.

The antibody Fc subunit may be derived from an IgG Fc subunit. For example, the IgG may be selected from the group consisting of IgG1, IgG2, IgG3 and IgG4. In some embodiments, the IgG is a human IgG1, and the IgG Fc subunit is a human IgG1 Fc subunit. In some embodiments, the Fc subunit comprises an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 35, 38 and 39. For example, the Fc subunit may comprise an amino acid sequence having one or more (e.g., 1-2, 1-3, 1-4, 1-5, 1-6, 1-7, 1-8, 1-9, 1-10, or more) amino acid deletion, insertion and/or substitution in the amino acid sequence as set forth in any one of SEQ ID NO: 35, 38 and 39.

In some embodiments, the Fc subunit may be a variant of the IgG Fc subunit (e.g., a variant of the human IgG1 Fc subunit). For example, the variant may comprise one or more amino acid mutations that enhance or reduce the ADCC or CDC activities. As another example, the variant may comprise one or more amino acid mutations that affect FcRn binding activity and/or the half-life of the molecule comprising the variant. As yet another example, the variant may comprise one or more amino acid mutations that affect an interaction (e.g., association) between two or more Fc subunits (or Fc monomers) and/or increase or decrease an efficiency of Fc heterodimer formation, for example, the variant may comprise one or more of the amino acid substitutions as described in CN102558355A, CN103388013A, CN105820251A, or CN106883297A, each of which is incorporated by reference herein.

The ISVD specific for PD-L1 may be capable of specifically binding to human PD-L1. For example, the ISVD specific for PD-L1 may be capable of specifically binding to an epitope in an extracellular domain of the human PD-L1. Such epitopes are known in the art, for example, as shown by Gang Hao et al., *J. Mol. Recognit.* 2015; 28: 269-276, Zhang et al., Oncotarget. 2017 October; 08 (52): 90215-90224, and Zhang et al., Cell Discov. 2017 Mar. 7; 3:17004.

For example, the ISVD specific for PD-L1 may be capable of binding to N-terminal IgV domain of human PD-L1. The N-terminal IgV domain of human PD-L1 (including the signal peptide) may comprise an amino acid sequence as set forth in SEQ ID NO: 64. In the present disclosure, the ISVD specific for PD-L1 may be capable of binding to residues I54, Y56, E58, Q66 and/or R113 of human PD-L1 N-terminal IgV domain. In a specific embodiment, the ISVD specific for PD-L1 is capable of binding to residues I54, Y56, E58, Q66 and R113 of human PD-L1 N-terminal IgV domain (e.g., amino acid residue I54, Y56, E58, Q66 and/or R113 of SEQ ID NO: 64). The ISVD specific for PD-L1 may be capable of further binding to residues D61, N63, V68, M115, S117, Y123 and/or R125 of human PD-L1 N-terminal IgV domain (e.g., amino acid residue D61, N63, V68, M115, S117, Y123 and/or R125 of SEQ ID NO: 64). In some cases, the ISVD specific for PD-L1 may be capable of binding to residues I54, Y56, E58, Q66, R113, D61, N63, V68, M115, S117, Y123 and/or R125 of human PD-L1 N-terminal IgV domain (e.g., amino acid residue I54, Y56, E58, Q66, R113, D61, N63, V68, M115, S117, Y123 and/or R125 of SEQ ID NO: 64). In some cases, the ISVD specific for PD-L1 is capable of binding to a conformational epitope of human PD-L1 N-terminal IgV domain, the conformational epitope may comprise residues I54, Y56, E58, Q66 and/or R113 of the human PD-L1 N-terminal IgV domain (e.g., amino acid residue I54, Y56, E58, Q66 and/or R113 of SEQ ID NO: 64). In some cases, the ISVD specific for PD-L1 is capable of binding to a conformational epitope of human PD-L1 N-terminal IgV domain, the conformational epitope may comprise residue I54, Y56, E58, Q66, R113, D61, N63, V68, M115, S117, Y123 and/or R125 of the human PD-L1 N-terminal IgV domain (e.g., amino acid residue I54, Y56, E58, Q66, R113, D61, N63, V68, M115, S117, Y123 and/or R125 of SEQ ID NO: 64).

The ISVDs specific for PD-L1 of the present disclosure (e.g., PD-L1 ISVD-9 and the humanized variants thereof) bind to the N-terminal IgV domain of human PD-L1. Taking PD-L1 ISVD-9 as an example, the residue Phe101 of PD-L1 ISVD-9 (SEQ ID NO: 6) interacts with Tyr56 of human PD-L1 N-terminal IgV domain, and when the Tyr56 of human PD-L1 N-terminal IgV domain was substituted by Ala, the binding affinity between PD-L1 ISVD-9 and PD-L1 was reduced by over 200 folds. When the Ile54 of human PD-L1 N-terminal IgV domain was substituted by Ala, the binding affinity between PD-L1 ISVD-9 and PD-L1 was reduced by about 40 folds. The residue Asp99 of PD-L1 ISVD-9 (SEQ ID NO: 6) interacts with Arg113 of human PD-L1 N-terminal IgV domain, and when the Arg113 of human PD-L1 N-terminal IgV domain was substituted by Ala, the binding affinity between PD-L1 ISVD-9 and PD-L1 was reduced by about 90 folds. The residue Ser100 of PD-L1 ISVD-9 (SEQ ID NO: 6) interacts with Glu58 of human PD-L1 N-terminal IgV domain, and when the Glu58 of human PD-L1 N-terminal IgV domain was substituted by Ala, the binding affinity between PD-L1 ISVD-9 and PD-L1 was reduced by about 25 folds. The residue Thr105 of PD-L1 ISVD-9 (SEQ ID NO: 6) interacts with Gln66 of human PD-L1 N-terminal IgV domain, and when the Gln66 of human PD-L1 N-terminal IgV domain was substituted by Ala, the binding affinity between PD-L1 ISVD-9 and PD-L1 was reduced by about 82 folds. In addition, residues D61, N63, V68, M115, S117, Y123 and R125 of human PD-L1 N-terminal IgV domain may be involved in the interaction between PD-L1 ISVD-9 and human PD-L1, substituting these residues with Ala resulted in a reduction of binding affinity by about 2-10 folds. These results are summarized in Table 1 below.

TABLE 1

Effects of Substitutions in human PD-L1 for binding of PD-L1 ISVD-9

| Human PD-L1 mutation | $K_D$ (M) | $K_{D,mutant}/K_{D,WT}$ |
|---|---|---|
| WT | 5.92E−09 | 1 |
| I54A | 2.42E−07 | 40.9 |
| Y56A | 1.24E−06 | 209.5 |
| E58A | 1.49E−07 | 25.2 |
| D61A | 1.99E−08 | 3.4 |
| N63A | 2.30E−08 | 3.9 |
| Q66A | 4.88E−07 | 82.4 |
| V68A | 2.76E−08 | 4.7 |
| R113A | 5.34E−07 | 90.2 |
| M115A | 5.51E−08 | 9.3 |
| S117A | 1.26E−08 | 2.1 |
| Y123A | 4.24E−08 | 7.2 |
| R125A | 2.97E−08 | 5.0 |

The ISVD specific for PD-L1 may be capable of blocking binding of PD-L1 to PD1. In some cases, the ISVD specific for PD-L1 may be capable of blocking binding of PD-L1 to CD80.

The ISVD specific for PD-L1 may cross-compete for binding to PD-L1 with a reference anti-PD-L1 antibody.

The reference anti-PD-L1 antibody may comprise a heavy chain CDR3. The heavy chain CDR3 may comprise an amino acid sequence as set forth in $DSFX_1X_2PTCX_3X_4X_5X_6SSGAFQY$ (SEQ ID NO: 1), wherein $X_1$ may be E or G; $X_2$ may be D or Y; $X_3$ may be T or P; X4 may be L or G; $X_5$ may be V or P; and $X_6$ may be T or A. In some cases, the reference anti-PD-L1 antibody may comprise a heavy chain CDR3 comprising an amino acid sequence as set forth in any one of SEQ ID NO: 5 and 9. The reference anti-PD-L1 antibody may also comprise a heavy chain CDR1. The heavy chain CDR1 may comprise an amino acid sequence as set forth in $GX_1X_2X_3X_4X_5RCMA$ (SEQ ID NO: 2), wherein $X_1$ may be K or N; $X_2$ may be M or I; $X_3$ may be S or I; $X_4$ may be S or R; and $X_5$ may be R or V. For example, the reference anti-PD-L1 antibody may comprise a heavy chain CDR1 comprising an amino acid sequence as set forth in any one of SEQ ID NO: 3 and 7. In some cases, the reference anti-PD-L1 antibody may comprise a heavy chain CDR2. The heavy chain CDR2 may comprise an amino acid sequence as set forth in any one of SEQ ID NO: 4, 8 and 11. In some cases, the reference anti-PD-L1 antibody is an ISVD specific for PD-L1, such as an anti-PD-L1 VHH. The reference anti-PD-L1 antibody may comprise a heavy chain variable domain. The reference anti-PD-L1 antibody may comprise a heavy chain variable domain comprising an amino acid sequence as set forth in any one of SEQ ID NO: 6, 10, 12, 13, 14 and 15. For example, the heavy chain variable domain may comprise an amino acid sequence as set forth in SEQ ID NO: 6.

In the present disclosure, the ISVD specific for PD-L1 (e.g., as comprised in the dimer of the present disclosure) may comprise a heavy chain CDR3. The heavy chain CDR3 may comprise an amino acid sequence as set forth in $DSFX_1X_2PTCX_3X_4X_5X_6SSGAFQY$ (SEQ ID NO: 1), wherein $X_1$ may be E or G; $X_2$ may be D or Y; $X_3$ may be T or P; X4 may be L or G; $X_5$ may be V or P; and $X_6$ may be T or A. For example, the ISVD specific for PD-L1 may comprise a heavy chain CDR3 comprising an amino acid sequence as set forth in any one of SEQ ID NO: 5 and 9.

For example, the ISVD specific for PD-L1 may comprise a heavy chain CDR3 comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 5 and 9. In some cases, the heavy chain CDR3 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NOs: 5 and 9.

In the present disclosure, the ISVD specific for PD-L1 (e.g., as comprised in the dimer of the present disclosure) may also comprise a heavy chain CDR1. The heavy chain CDR1 may comprise an amino acid sequence as set forth in $GX_1X_2X_3X_4X_5RCMA$ (SEQ ID NO: 2), wherein $X_1$ may be K or N; $X_2$ may be M or I; $X_3$ may be S or I; $X_4$ may be S or R; and $X_5$ may be R or V. For example, the ISVD specific for PD-L1 may comprise a heavy chain CDR1 comprising an amino acid sequence as set forth in any one of SEQ ID NO: 3 and 7.

For example, the ISVD specific for PD-L1 may comprise a heavy chain CDR1 comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 3 and 7. In some cases, the heavy chain CDR1 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NOs: 3 and 7.

In the present disclosure, the ISVD specific for PD-L1 (e.g., as comprised in the dimer of the present disclosure) may further comprise a heavy chain CDR2. The heavy chain CDR2 may comprise any suitable amino acid sequence. In some case, the ISVD specific for PD-L1 may comprise a heavy chain CDR2 comprising an amino acid sequence as set forth in any one of SEQ ID NO: 4, 8 and 11.

For example, the ISVD specific for PD-L1 may comprise a heavy chain CDR2 comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 4, 8 and 11. In some cases, the heavy chain CDR2 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NOs: 4, 8 and 11.

In the present disclosure, the ISVD specific for PD-L1 (as comprised in the dimer of the present disclosure) may comprise a heavy chain variable domain. The ISVD specific for PD-L1 may comprise a heavy chain variable domain comprising an amino acid sequence as set forth in any one of SEQ ID NO: 6, 10, 12, 13, 14 and 15. For example, the heavy chain variable domain may comprise an amino acid sequence as set forth in SEQ ID NO: 6.

For example, the ISVD specific for PD-L1 may comprise a heavy chain variable domain comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 6, 10, 12, 13, 14 and 15. In some cases, the ISVD specific for PD-L1 may comprise a heavy chain variable domain comprising an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NO: 6, 10, 12, 13, 14 and 15.

In the present disclosure, the ISVD specific for PD-L1 may comprise an amino acid sequence as set forth in any one of SEQ ID NO: 6, 10, 12, 13, 14 and 15. For example, the ISVD specific for PD-L1 (as comprised in the dimer of the present disclosure) may comprise an amino acid sequence as set forth in SEQ ID NO: 6. For example, the ISVD specific for PD-L1 may comprise an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 6, 10, 12, 13, 14 and 15. In some cases, the ISVD specific for PD-L1 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NO: 6, 10, 12, 13, 14 and 15.

In some cases, the ISVD specific for PD-L1 comprises or consists of a heavy chain variable domain (VH or VHH).

For example, the ISVD specific for PD-L1 may be selected from PD-L1 ISVD-9, PD-L1 ISVD-6, PD-L1 ISVD-m3, PD-L1 ISVD-4, PD-L1 ISVD-11 and PD-L1 ISVD-13.

The ISVD specific for CTLA4 may be capable of specifically binding to human CTLA4. For example, the ISVD specific for CTLA4 may be capable of specifically binding to an epitope in an extracellular domain of the human CTLA4, such an epitope may include those described in CN107400166A, and those described by Udupi A. Ramagopal, et. al., PNAS 2017 May, 114 (21)

The ISVD specific for CTLA4 may be capable of blocking binding of CTLA4 to CD80. In some cases, the ISVD specific for CTLA4 may be capable of blocking binding of CTLA4 to CD86. In some cases, the ISVD specific for CTLA4 may be humanized.

The ISVD specific for CTLA4 may cross-compete for binding to CTLA4 with a reference anti-CTLA4 antibody.

The reference anti-CTLA4 antibody may comprise a heavy chain CDR3. The heavy chain CDR3 may comprise an amino acid sequence as set forth in SEQ ID NO: 19. The reference anti-CTLA4 antibody may also comprise a heavy chain CDR1. The heavy chain CDR1 may comprise an amino acid sequence as set forth in SEQ ID NO: 17. In some cases, the reference anti-CTLA4 antibody may comprise a heavy chain CDR2. The heavy chain CDR2 may comprise an amino acid sequence as set forth in AIX1X2GGGSTYYADSVKG (SEQ ID NO: 16), wherein $X_1$ may be Y or S; and $X_2$ may be I or L. For example, the heavy chain CDR2 may comprise an amino acid sequence as set forth in any one of SEQ ID NO: 18, 21 and 23. In some cases, the reference anti-CTLA4 antibody is an ISVD specific for CTLA4, such as an anti-CTLA4 VHH. The reference anti-CTLA4 antibody may comprise a heavy chain variable domain. The reference anti-CTLA4 antibody may comprise a heavy chain variable domain comprising an amino acid sequence as set forth in any one of SEQ ID NO: 20, 22, and 24-32. For example, the heavy chain variable domain may comprise an amino acid sequence as set forth in SEQ ID NO: 20.

In the present disclosure, the ISVD specific for CTLA4 (e.g., as comprised in the dimer of the present disclosure) may comprise a heavy chain CDR3. The heavy chain CDR3 may comprise an amino acid sequence as set forth in SEQ ID NO: 19.

In some cases, the ISVD specific for CTLA4 may comprise a heavy chain CDR3 comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in SEQ ID NO: 19. In some cases, the heavy chain CDR3 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in SEQ ID NO: 19.

In the present disclosure, the ISVD specific for CTLA4 (e.g., as comprised in the dimer of the present disclosure) may also comprise a heavy chain CDR1. The heavy chain CDR1 may comprise an amino acid sequence as set forth in SEQ ID NO: 17.

In some cases, the ISVD specific for CTLA4 may comprise a heavy chain CDR1 comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in SEQ ID NO: 17. In some cases, the heavy chain CDR1 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in SEQ ID NOs: 17.

In the present disclosure, the ISVD specific for CTLA4 (e.g., as comprised in the dimer of the present disclosure) may further comprise a heavy chain CDR2. The heavy chain CDR2 may comprise an amino acid sequence as set forth in AIX1X2GGGSTYYADSVKG (SEQ ID NO: 16), wherein $X_1$ may be Y or S; and $X_2$ may be I or L. In some case, the ISVD specific for CTLA4 may comprise a heavy chain CDR2 comprising an amino acid sequence as set forth in any one of SEQ ID NO: 18, 21 and 23.

For example, the ISVD specific for CTLA4 may comprise a heavy chain CDR2 comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 18, 21 and 23. In some cases, the heavy chain CDR2 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NOs: 18, 21 and 23.

In the present disclosure, the ISVD specific for CTLA4 (as comprised in the dimer of the present disclosure) may comprise a heavy chain variable domain. The ISVD specific for CTLA4 may comprise a heavy chain variable domain comprising an amino acid sequence as set forth in any one of SEQ ID NO: 20, 22, and 24-32. For example, the heavy chain variable domain may comprise an amino acid sequence as set forth in SEQ ID NO: 20.

For example, the ISVD specific for CTLA4 may comprise a heavy chain variable domain comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 20, 22, and 24-32. In some cases, the ISVD specific for CTLA4 may comprise a heavy chain variable domain comprising an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NO: 20, 22, and 24-32.

In the present disclosure, the ISVD specific for CTLA4 may comprise an amino acid sequence as set forth in any one of SEQ ID NO: 20, 22, and 24-32. For example, the ISVD specific for CTLA4 (as comprised in the dimer of the present disclosure) may comprise an amino acid sequence as set forth in SEQ ID NO: 20.

For example, the ISVD specific for CTLA4 may comprise an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 20, 22, and 24-32. In some cases, the ISVD specific for CTLA4 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NO: 20, 22, and 24-32.

In some cases, the ISVD specific for CTLA4 comprises or consists of a heavy chain variable domain (VH or VHH).

For example, the ISVD specific for CTLA4 may be selected from CTLA4 ISVD-34, CTLA4 ISVD-C1, CTLA4 ISVD-13, CTLA4 ISVD-26, CTLA4 ISVD-27, CTLA4 ISVD-28, CTLA4 ISVD-29, CTLA4 ISVD-30, CTLA4 ISVD-31, CTLA4 ISVD-32, and CTLA4 ISVD-33.

For example, the dimer of the present application may comprise or consist of two polypeptide chains. The amino acid sequence of the two polypeptide chains may be identical or different. In some cases, the dimer of the present disclosure may be homodimer.

In the present disclosure, one or both of the two polypeptide chains of the dimer may comprise an amino acid sequence as set forth in any one of SEQ ID NOs: 40-43, 48 and 50. For example, one or both of the two polypeptide chains of the dimer may comprise an amino acid sequence as set forth in SEQ ID NO: 40.

In specific examples, one or both of the two polypeptide chains of the dimer may comprise an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 40-43, 46, 48 and 50. In some cases, one or both of the two polypeptide chains of the dimer may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NO: 40-43, 46, 48 and 50.

In an example, an ISVD specific for PD-L1 may be fused (directly or indirectly, e.g., via a linker, such as a peptide linker) to an N-terminal amino acid of an ISVD specific for CTLA4 to form a bi-specific binding moiety. Then, one such bi-specific binding moiety may be fused (directly or indirectly, e.g., via a linker, such as a peptide linker) to an N-terminal amino acid of one Fc subunit of the present disclosure to provide one polypeptide chain of the dimer. Then, another such bi-specific binding moiety may be fused (directly or indirectly, e.g., via a linker, such as a peptide linker) to an N-terminal amino acid of another Fc subunit of the present disclosure to provide the other polypeptide chain of the dimer. The two Fc subunits of the two polypeptide chains may associate with each other (e.g., via non-covalent interactions and/or disulfide bond or other covalent bond, in some cases, such covalent bond is not a peptide bond) to form the dimer. The two bi-specific binding moieties may be identical or different. The two Fc subunits may be identical or different.

In some embodiments, the dimer is a proteinaceous homodimer comprising two identical polypeptide chains, with each polypeptide chain comprising one of the bi-specific binding moiety fused to one of the Fc subunits, and the two Fc subunits associate with each other to form the proteinaceous homodimer. The two Fc subunits may associate with each other via non-covalent interactions and/or disulfide bond or other covalent bond, in some cases, such covalent bond is not a peptide bond.

The dimer of the present disclosure may be capable of competing with CD80 and/or CD86 for binding to CTLA4. For example, the competition may be examined in an in vitro experiment using CTLA4 expressing cell lines, such as a CTLA4 expressing HEK293 cell line. As another example, the competition may be examined in an ELISA assay, such as a competition ELISA assay.

The dimer of the present disclosure may be capable of competing with PD1 and/or CD80 for binding to PD-L1. For example, the competition may be examined in an in vitro experiment using PD-L1 expressing cell lines, such as a PD-L1 expressing A375 cell line. As another example, the competition may be examined in an ELISA assay, such as a competition ELISA assay.

The dimer of the present disclosure may be capable of blocking binding of PD-L1 to PD-1. In some cases, the dimer of the present disclosure may be capable of blocking binding of PD-L1 to CD80. In some cases, the dimer of the present disclosure may be capable of blocking binding of CTLA4 to CD80. In some cases, the dimer of the present disclosure may be capable of blocking binding of CTLA4 to CD86.

The dimer of the present disclosure may bind to CTLA4 with a $K_D$ of a value no more than about $1 \times 10^{-6}$ M, for example, no more than about $1 \times 10^{-7}$ M, no more than about $1 \times 10^{-8}$ M, no more than about $0.5 \times 10^{-8}$ M, no more than about $1 \times 10^{-9}$ M, no more than about $1 \times 10^{10}$ M or lower.

The dimer of the present disclosure may bind to PD-L1 with a $K_D$ of a value no more than about $1 \times 10^{-6}$ M, for example, no more than about $1 \times 10^{-7}$ M, no more than about $1 \times 10^{-8}$ M, no more than about $0.5 \times 10^{-8}$ M, no more than about $1 \times 10^{-9}$ M, no more than about $1 \times 10^{31}$ $^{10}$ M or lower.

The dimer of the present disclosure may be capable of stimulating the secretion of an immunoregulator (e.g., IL-2) by immune cells (e.g., PBMC cells).

For example, the dimer of the present disclosure may be selected from aPDL1.9-aCTLA4.34-Fc, aPDL1.9-L-aCTLA4.34-Fc, aCTLA4.34-aPDL1.9-Fc, aCTLA4.34-L-aPDL1.9-Fc, aPDL1.6-aCTLA4.34-Fc, aPDL1.m3-aCTLA4.34-Fc and aPDL1.9-aCTLA4.13-Fc.

In another aspect, the present disclosure provides an immunoconjugate. The immunoconjugate may comprise one or more of the dimers according to the present disclosure. The immunoconjugate may further comprise one or more additional moieties, such as one or more additional binding moieties, or one or more additional effector moieties.

In another aspect, the present disclosure provides an isolated nucleic acid or isolated nucleic acids encoding the dimer of the present application. For example, the isolated nucleic acid or isolated nucleic acids may comprise one or more (e.g., 1-2, 1-3, 1-4, 1-5, 1-6, 1-7, 1-8, 1-9, 1-10, or more) nucleic acid molecules. Each nucleic acid molecule may encode for the complete dimer or a part thereof. For example, a nucleic acid molecule may comprise various fragments encoding different parts (e.g., the ISVD specific for PD-L1 or a part thereof, the ISVD specific for CTLA4 or a part thereof, the Fc subunit or a part thereof, and/or the bi-specific binding moiety or a part thereof, etc.) of the dimer, and the various fragments may be directly or indirectly ligated together to form one nucleic acid molecule. In some cases, there are more than one nucleic acid molecules, and each nucleic acid molecule encodes for a part (e.g., the ISVD specific for PD-L1 or a part thereof, the ISVD specific for CTLA4 or a part thereof, the Fc subunit or a part thereof, and/or the bi-specific binding moiety or a part thereof, etc.) of the dimer.

The isolated nucleic acid or isolated nucleic acids according to the present disclosure may be prepared or obtained based on information reflecting the amino acid sequences of the expression product they encode for. This may be achieved according to general practice in the art, e.g., by automated DNA synthesis and/or recombinant DNA technology. Alternatively, in some cases, the isolated nucleic acid or isolated nucleic acids according to the present disclosure may be isolated from a suitable natural source.

In another aspect, the present disclosure provides a vector or vectors comprising the isolated nucleic acid or isolated nucleic acids. For example, the vector or vectors may comprise one or more (e.g., 1-2, 1-3, 1-4, 1-5, 1-6, 1-7, 1-8, 1-9, 1-10, or more) of the isolated nucleic acid according to the present disclosure.

A suitable vector may comprise, e.g., a plasmid, an endoplasmic plasmid or YAC. The vector may be an expression vector that enables expression of the dimer according to the present disclosure in vitro and/or in vivo (i.e., in a suitable host cell, host organism and/or expression system). The expression vector typically may comprise at least one isolated nucleic acid according to the present disclosure operably linked to one or more suitable expression regulatory elements (e.g., promoters, enhancers, terminator, etc.). The selection of the elements and their sequences for expression in a particular host is common to those skilled in the art. Specific examples of regulatory elements and other elements that are useful or necessary for the expression of the dimer according to the present disclosure include, e.g., promoters, enhancers, terminators, integration factors, selectable markers, leader sequences, reporter genes.

In some embodiments, the vector or vectors according to the present disclosure may be selected from a group consisting of: plasmids, viral vectors, cosmids, and artificial chromosomes. In some cases, the vector may be selected from the group consisting of: PET32b (Novagen), pCMVp-NEO-BAN, pEGFP, pEGFT-Actin, pSV2 and CMV4. In some embodiments, the vector is pCDNA4 (Invitrogen, Cat V86220) and/or PET32b (Novagen, product number: 69016-3).

In another aspect, the present disclosure provides an isolated host cell comprising the isolated nucleic acid or isolated nucleic acids or the vector or vectors. For example, the host cell may comprise one or more (e.g., 1-2, 1-3, 1-4, 1-5, 1-6, 1-7, 1-8, 1-9, 1-10, or more) of the isolated nucleic acid according to the present disclosure, and/or one or more (e.g., 1-2, 1-3, 1-4, 1-5, 1-6, 1-7, 1-8, 1-9, 1-10, or more) of the vector according to the present disclosure.

The host cell according to the present disclosure may be selected from the group consisting of: bacterial cells, fungal cells, mammalian cells and amphibian cells, insect cells, plant cells, and any other cells in the art for expressing heterologous proteins.

The bacterial cells may include Gram-negative bacterial strains (e.g., *Escherichia coli* strains, *Proteus* strains and *Pseudomonas* strains) and Gram-positive bacterial strains (e.g., *Bacillus* sp. *Bacillus* strain, *Streptomyces* strain, *Staphylococcus* strain and *Lactococcus* strain).

The fungal cells may include cells of species of *Trichoderma, Neurospora* and *Aspergillus*, or *Saccharomyces* (e.g., *Saccharomyces cerevisiae*), lysozyme Yeast (*Schizosaccharomyces*) (e.g., *Schizosaccharomyces pombe*), *Pichia* (e.g., *Pichia pastoris* and *Pichia methanolica*) and the genus of *Hansenula*.

The mammalian cells may include, for example, HEK293 cells, CHO cells, BHK cells, HeLa cells, COS cells, and engineered cells derived therefrom, such as GS knockout CHO cells.

Pharmaceutical Compositions

In another respect, the present disclosure provides a pharmaceutical composition comprising the dimer and/or the immunoconjugate according to the present disclosure; and optionally a pharmaceutically acceptable excipient. In some cases, the pharmaceutical composition may comprise cells or tissues (such as genetically engineered cells or tissues), the dimer and/or the immunoconjugate according to the present disclosure, or fragments thereof may be comprised by such cells or tissues.

Examples of pharmaceutically acceptable excipients include, but are not limited to, inert solid diluents and fillers, diluents, sterile aqueous solution and various organic solvents, permeation enhancers, solubilizers and adjuvants.

In some embodiments, the dimer or the immunoconjugate is formulated for oral administration, intravenous administration, intramuscular administration, in-situ administration at the site of a tumor, inhalation, rectal administration, vaginal administration, transdermal administration, or administration via subcutaneous repository.

The pharmaceutical composition may be used for inhibiting tumor growth. For example, the pharmaceutical compositions may inhibit or delay the development or progress of a disease, may reduce tumor size (and even substantially eliminate tumors), and may alleviate and/or stabilize a disease condition.

Described below are non-limiting exemplary pharmaceutical compositions and methods for preparing the same.

The subject pharmaceutical composition may, for example, be in a form suitable for parenteral injection as a sterile solution, suspension or emulsion. The pharmaceutical composition may be in unit dosage forms suitable for single administration of precise dosages. The pharmaceutical composition can further comprise a dimer and/or an immunoconjugate according to the present disclosure as an active ingredient and may include a conventional pharmaceutical carrier or excipient. Further, it may include other medicinal or pharmaceutical agents, carriers, adjuvants, etc.

Exemplary parenteral administration forms include, but not limited to, solutions or suspensions of the dimer and/or immunoconjugate of the present disclosure in sterile aqueous solutions, for example, aqueous propylene glycol or dextrose solutions. Such dosage forms can be suitably buffered with salts such as histidine and/or phosphate, if desired.

In some embodiments, the present disclosure provides a pharmaceutical composition for injection containing a dimer and/or immunoconjugate of the present disclosure and a pharmaceutical excipient suitable for injection.

The forms in which the pharmaceutical compositions of the present disclosure may be incorporated for administration by injection include aqueous or oil suspensions, or emulsions with appropriate oil, or a sterile aqueous solution, and similar pharmaceutical vehicles.

The present disclosure further encompasses anhydrous pharmaceutical compositions and dosage forms comprising an active ingredient (e.g., a dimer and/or immunoconjugate of the present disclosure), since water can facilitate the degradation of some polypeptides. Anhydrous pharmaceutical compositions and dosage forms of the disclosure can be prepared using anhydrous or low moisture containing ingredients and low moisture or low humidity conditions.

A dimer and/or immunoconjugate of the present disclosure can be combined in an intimate admixture with a pharmaceutical carrier according to conventional pharmaceutical compounding techniques. The carrier can take a wide variety of forms depending on the form of preparation desired for administration. In preparing the compositions, any of the usual pharmaceutical media can be employed as carriers, such as, for example, water, glycols, oils, alcohols, flavoring agents, preservatives, coloring agents, and the like.

The pharmaceutical compositions of the present disclosure may comprise a therapeutically effective amount of the active agent (e.g., the dimer and/or immunoconjugate of the present disclosure). A therapeutically effective amount is an amount of the subject pharmaceutical composition capable of preventing and/or curing (at least partially) a condition or disorder (e.g., cancer) and/or any complications thereof in a subject suffering from or having a risk of developing the condition or disorder. The specific amount/concentration of the active agent comprised may vary according to the method of administration and the need of a patient, and can be determined based on e.g., volume, viscosity, and/or body weight of a patient etc. For example, an appropriate dosage may be about 0.1 mg or 1 mg/kg/day to about 150 mg/kg/day (such as about 0.1 mg/kg—about 0.3 mg/kg, about 0.1 mg/kg -about 1 mg/kg, about 0.1 mg/kg -about 3 mg/kg, about 0.1 mg/kg -about 5 mg/kg, about 0.1 mg/kg -about 10 mg/kg, such as about 1 mg/kg to about 5 mg/kg, such as about 3 mg/kg to about 5 mg/kg); sometimes, the dosage can be even higher.

Medical Use and Methods of Treatment

The dimer, the immunoconjugate or the pharmaceutical composition according to the present disclosure may be used for the treatment of a disease in a subject in need thereof.

In another aspect, the present disclosure provides a use of the dimer, the immunoconjugate or the pharmaceutical composition according to the present disclosure in the treatment of a disease in a subject in need thereof.

In another aspect, the present disclosure provides a use of the dimer, the immunoconjugate, or the pharmaceutical composition according to the present disclosure, in the preparation of a medicament for treating a disease in a subject in need thereof.

In another aspect, the present disclosure provides a method for treating a disease in a subject in need thereof, comprising administering to the subject an effective amount of the dimer, the immunoconjugate, or the pharmaceutical composition according to the present disclosure.

The disease or disorder may be any disease or disorder potentially affected by a PD-L1 binding moiety and/or a CTLA4 binding moiety.

The medicament may be formulated in a form appropriate to be administered intravenously.

In some embodiment, the disease or disorder is a cancer. The cancer may be a solid tumor, a hematologic cancer, or a lymphoma. For example, the cancer may be selected from lung cancer (such as non-small-cell lung cancer), breast cancer (such as Triple-Negative Breast Cancer), kidney cancer (such as renal cell carcinoma), melanoma, cervical cancer, uterus cancer, pancreatic cancer, peritoneal carcinoma, ovarian cancer and colon cancer. The cancer may be advanced or metastatic cancer.

In some cases, the cancer may be non-responsive to treatment with a PD-1 antagonist and/or a PD-L1 antagonist. For example, treatment with a PD-1 antagonist and/or a PD-L1 antagonist does not result in substantial or observable delay or inhibition of cancer progression or tumor growth. In some cases, prior to administering the dimer/composition/immunoconjugate of the present disclosure, the cancer has not been treated with a PD-1 antagonist and/or a PD-L1 antagonist. The PD-1 antagonist may be a PD-1 blocking antibody. The PD-L1 antagonist may be a PD-L1 blocking antibody.

The cancer or cancer cell may be within the body of a subject, e.g., a cancer or cancer cell within a human or in a non-human animal (e.g., a mammal).

In some cases, the cancer/tumor may be unresectable.

In some cases, the cancer/tumor may be metastatic (such as metastatic solid tumor).

In some cases, the cancer/tumor may be refractory and/or intolerant to standard therapies.

The subject may be a mammal. In some embodiments, the mammal is a human. In some embodiments, the mammal is a mouse, a rat, a cat, a dog, a rabbit, a pig, a sheep, a horse, a bovine, a goat, a gerbil, a hamster, a guinea pig, a monkey or any other mammal. Many such mammals may be subjects that are known to the art as preclinical models for certain diseases or disorders, including solid tumors and/or other cancers (e.g., Talmadge et al., 2007 Am. J. Pathol. 170:793; Kerbel, 2003 Canc. Biol. Therap. 2(4 Suppl 1): S134; Man et al., 2007 Canc. Met. Rev. 26:737; Cespedes et al., 2006 Clin. TransL Oncol. 8:318).

In another aspect, the present disclosure provides a method for blocking binding of CD80 and/or CD86 to CTLA4, comprising administering the dimer, the immunoconjugate, or the pharmaceutical composition according to the present disclosure.

In another aspect, the present disclosure provides a method for blocking binding of PD1 and/or CD80 to PD-L1, comprising administering the dimer, the immunoconjugate, or the pharmaceutical composition according to the present disclosure.

In another aspect, the present disclosure provides a method for stimulating secretion of cytokines (such as interleukins, e.g., IL-2) by immune cells, comprising administering to the immune cells the dimer, the immunoconjugate, or the pharmaceutical composition according to the present disclosure. The immune cells may comprise, e.g., PBMC cells, T cells, or other immune cells.

In another aspect, the present disclosure provides a method for enhancing an immune response in a subject, comprising administering to the subject the dimer, the immunoconjugate, or the pharmaceutical composition according to the present disclosure.

An enhanced immune response may comprise, e.g., enhanced humoral immune response (i.e., B cell response) and/or a cellular response (i.e., T cell response). An enhanced humoral immune response can be demonstrated by e.g, showing increased antibody titers in a treated subject (e.g., as determined by ELISA). An enhanced cellular immune response can be demonstrated by e.g., showing that treated T cells, or T cells from a treated subject are more highly activated. T cell activation may be assessed by measuring T-cell proliferation or T-cell cytokine elaboration upon in vitro stimulation of T-cells by an antigen (e.g., by ELISpot). T cell activation may also be assayed via flow cytometry.

Methods for Preparing the Dimers

In another aspect, the present disclosure provides a method for producing the dimer according to the present disclosure, comprising (i) culturing the host cell of the present disclosure under conditions to effect expression and formation of the dimer, and (ii) harvesting the dimer formed.

In some embodiments, the method does not comprise enriching the dimer in the products expressed by the host cells according to the present disclosure.

In some embodiments, the method further comprises the steps of isolating and/or purifying the dimer.

In some embodiments, the method further comprises transfecting/transforming host cells with polynucleotides/vectors encoding/expressing the dimer of the present disclosure, one or more members thereof, or fragments thereof.

In some embodiments, the dimer of the present disclosure is produced by expressing a vector in a cell under conditions suitable for protein expression.

Factors that may vary among suitable conditions for protein expression include factors such as incubation time, temperature, and medium, and may depend on cell type and will be readily determined by one of ordinary skill in the art.

In some embodiments, during the process of producing the dimer of the present disclosure, the host cells are grown in cultures, and in any apparatus that may be used to grow cultures, including fermenters. Cells may be grown as monolayers or attached to a surface. Alternatively, the host cells may be grown in suspension. The cells can be grown in a culture medium that is serum-free. The media can be a commercially available media.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Exemplary Embodiments

Non-limiting, exemplary embodiments of the present disclosure are described as follows.

1. A dimer formed by two polypeptide chains, with each of said two polypeptide chains comprising an antibody Fc subunit, wherein said dimer comprises two or more immunoglobulin single variable domains (ISVDs), at least one of said ISVDs is specific for PD-L1, and at least one of said ISVDs is specific for CTLA4.
2. The dimer according to embodiment 1, wherein at least one of said two polypeptide chains comprise both an ISVD specific for PD-L1 and an ISVD specific for CTLA4.
3. The dimer according to any one of embodiments 1-2, wherein each of said two polypeptide chains comprises both an ISVD specific for PD-L1 and an ISVD specific for CTLA4.
4. The dimer according to any one of embodiments 1-3, wherein for one or both of said two polypeptide chains, said ISVD specific for PD-L1 is fused to said ISVD specific for CTLA4, optionally via a linker.
5. The dimer according to any one of embodiments 1-4, wherein for one or both of said two polypeptide chains:
   said ISVD specific for PD-L1 is fused to said ISVD specific for CTLA4, optionally via a linker; and
   said ISVD specific for CTLA4 is fused to said antibody Fc subunit, optionally via a linker.
6. The dimer according to any one of embodiments 1-5, wherein for one or both of said two polypeptide chains:
   C terminus of said ISVD specific for PD-L1 is fused to N terminus of said ISVD specific for CTLA4, optionally via a linker; and
   C terminus of said ISVD specific for CTLA4 is fused to N terminus of said antibody Fc subunit, optionally via a linker.
7. The dimer according to any one of embodiments 1-4, wherein for one or both of said two polypeptide chains:
   said ISVD specific for PD-L1 is fused to said ISVD specific for CTLA4, optionally via a linker; and
   said ISVD specific for PD-L1 is fused to said antibody Fc subunit, optionally via a linker.
8. The dimer according to embodiment 7, wherein for one or both of said two polypeptide chains:
   C terminus of said ISVD specific for CTLA4 is fused to N terminus of said ISVD specific for PD-L1, optionally via a linker; and
   C terminus of said ISVD specific for PD-L1 is fused to N terminus of said antibody Fc subunit, optionally via a linker.
9. The dimer according to any one of embodiments 1-8, wherein said antibody Fc subunit is derived from an IgG Fc subunit.
10. The dimer according to embodiment 9, wherein said IgG is human IgG1.
11. The dimer according to any one of embodiments 1-10, wherein said antibody Fc subunit comprises an amino acid sequence as set forth in any one of SEQ ID NO: 35, 38 and 39.
12. The dimer according to any one of embodiments 1-11, wherein said ISVD specific for PD-L1 is capable of binding to N-terminal IgV domain of human PD-L1.

13. The dimer according to any one of embodiments 1-12, wherein said ISVD specific for PD-L1 is capable of binding to residues I54, Y56, E58, Q66 and/or R113 of human PD-L1 N-terminal IgV domain, wherein said human PD-L1 N-terminal IgV domain comprises an amino acid sequence as set forth in SEQ ID NO: 64.

14. The dimer according to embodiment 13, wherein said ISVD specific for PD-L1 is capable of further binding to residues D61, N63, V68, M115, S117, Y123 and/or R125 of human PD-L1 N-terminal IgV domain, wherein said human PD-L1 N-terminal IgV domain comprises an amino acid sequence as set forth in SEQ ID NO: 64.

15. The dimer according to any one of embodiments 1-14, wherein said ISVD specific for PD-L1 is capable of binding to a conformational epitope of human PD-L1 N-terminal IgV domain, wherein said conformational epitope comprises residues I54, Y56, E58, Q66 and R113 of said human PD-L1 N-terminal IgV domain, and wherein said human PD-L1 N-terminal IgV domain comprises an amino acid sequence as set forth in SEQ ID NO: 64.

16. The dimer according to any one of embodiments 1-15, wherein said ISVD specific for PD-L1 is capable of binding to a conformational epitope of human PD-L1 N-terminal IgV domain, wherein said conformational epitope comprises residues I54, Y56, E58, Q66, R113, D61, N63, V68, M115, S117, Y123 and R125 of said human PD-L1 N-terminal IgV domain, and wherein said human PD-L1 N-terminal IgV domain comprises an amino acid sequence as set forth in SEQ ID NO: 64.

17. The dimer according to any one of embodiments 1-16, wherein said ISVD specific for PD-L1 is capable of blocking binding of PD-L1 to PD1.

18. The dimer according to any one of embodiments 1-17, wherein said ISVD specific for PD-L1 is capable of blocking binding of PD-L1 to CD80.

19. The dimer according to any one of embodiments 1-18, wherein said ISVD specific for PD-L1 cross-competes for binding to PD-L1 with a reference anti-PD-L1 antibody, wherein said reference anti-PD-L1 antibody comprises a heavy chain CDR3 comprising an amino acid sequence as set forth in SEQ ID NO: 1.

20. The dimer according to embodiment 19, wherein said reference anti-PD-L1 antibody comprises a heavy chain CDR3 comprising an amino acid sequence as set forth in any one of SEQ ID NO: 5 and 9.

21. The dimer according to any one of embodiments 19-20, wherein said reference anti-PD-L1 antibody comprises a heavy chain CDR1 comprising an amino acid sequence as set forth in SEQ ID NO: 2.

22. The dimer according to any one of embodiments 19-21, wherein said reference anti-PD-L1 antibody comprises a heavy chain CDR1 comprising an amino acid sequence as set forth in any one of SEQ ID NO: 3 and 7.

23. The dimer according to any one of embodiments 19-22, wherein said reference anti-PD-L1 antibody comprises a heavy chain CDR2 comprising an amino acid sequence as set forth in any one of SEQ ID NO: 4, 8 and 11.

24. The dimer according to any one of embodiments 19-23, wherein said reference anti-PD-L1 antibody is an ISVD specific for PD-L1.

25. The dimer according to any one of embodiments 19-24, wherein said reference anti-PD-L1 antibody comprises a heavy chain variable domain comprising an amino acid sequence as set forth in any one of SEQ ID NO: 6, 10, 12, 13, 14 and 15.

26. The dimer according to any one of embodiments 19-25, wherein said reference anti-PD-L1 antibody comprises a heavy chain variable domain comprising an amino acid sequence as set forth in SEQ ID NO: 6.

27. The dimer according to any one of embodiments 1-26, wherein said ISVD specific for PD-L1 comprises a heavy chain CDR3 comprising an amino acid sequence as set forth in SEQ ID NO: 1.

28. The dimer according to any one of embodiments 1-27, wherein said ISVD specific for PD-L1 comprises a heavy chain CDR3 comprising an amino acid sequence as set forth in any one of SEQ ID NO: 5 and 9.

29. The dimer according to any one of embodiments 1-28, wherein said ISVD specific for PD-L1 comprises a heavy chain CDR1 comprising an amino acid sequence as set forth in SEQ ID NO: 2.

30. The dimer according to any one of embodiments 1-29, wherein said ISVD specific for PD-L1 comprises a heavy chain CDR1 comprising an amino acid sequence as set forth in any one of SEQ ID NO: 3 and 7.

31. The dimer according to any one of embodiments 1-30, wherein said ISVD specific for PD-L1 comprises a heavy chain CDR2 comprising an amino acid sequence as set forth in any one of SEQ ID NO: 4, 8 and 11.

32. The dimer according to any one of embodiments 1-31, wherein said ISVD specific for PD-L1 comprises a heavy chain variable domain comprising an amino acid sequence as set forth in any one of SEQ ID NO: 6, 10, 12, 13, 14 and 15.

33. The dimer according to any one of embodiments 1-32, wherein said ISVD specific for PD-L1 comprises a heavy chain variable domain comprising an amino acid sequence as set forth in SEQ ID NO: 6.

34. The dimer according to any one of embodiments 1-33, wherein said ISVD specific for CTLA4 is capable of specifically binding to human CTLA4.

35. The dimer according to any one of embodiments 1-34, wherein said ISVD specific for CTLA4 is capable of blocking binding of CTLA4 to CD80.

36. The dimer according to any one of embodiments 1-35, wherein said ISVD specific for CTLA4 is capable of blocking binding of CTLA4 to CD86.

37. The dimer according to any one of embodiments 1-36, wherein said ISVD specific for CTLA4 cross-competes for binding to CTLA4 with a reference anti-CTLA4 antibody, wherein said reference anti-CTLA4 antibody comprises a heavy chain CDR3 comprising an amino acid sequence as set forth in SEQ ID NO: 19.

38. The dimer according to embodiment 37, wherein said reference anti-CTLA4 antibody comprises a heavy chain CDR1 comprising an amino acid sequence as set forth in SEQ ID NO: 17.

39. The dimer according to any one of embodiments 37-38, wherein said reference anti-CTLA4 antibody comprises a heavy chain CDR2 comprising an amino acid sequence as set forth in SEQ ID NO: 16.

40. The dimer according to any one of embodiments 37-39, wherein said reference anti-CTLA4 antibody comprises a heavy chain CDR2 comprising an amino acid sequence as set forth in any one of SEQ ID NO: 18, 21 and 23.

41. The dimer according to any one of embodiments 37-40, wherein said reference anti-CTLA4 antibody is an ISVD specific for CTLA4.

42. The dimer according to any one of embodiments 37-41, wherein said reference anti-CTLA4 antibody comprises a heavy chain variable domain comprising an amino acid sequence as set forth in any one of SEQ ID NO: 20, 22, and 24-32.

43. The dimer according to any one of embodiments 37-42, wherein said reference anti-CTLA4 antibody comprises a heavy chain variable domain comprising an amino acid sequence as set forth in SEQ ID NO: 20.

44. The dimer according to any one of embodiments 1-43, wherein said ISVD specific for CTLA4 comprises a heavy chain CDR3 comprising an amino acid sequence as set forth in SEQ ID NO: 19.

45. The dimer according to any one of embodiments 1-44, wherein said ISVD specific for CTLA4 comprises a heavy chain CDR1 comprising an amino acid sequence as set forth in SEQ ID NO: 17.

46. The dimer according to any one of embodiments 1-45, wherein said ISVD specific for CTLA4 comprises a heavy chain CDR2 comprising an amino acid sequence as set forth in SEQ ID NO: 16.

47. The dimer according to any one of embodiments 1-46, wherein said ISVD specific for CTLA4 comprises a heavy chain CDR2 comprising an amino acid sequence as set forth in any one of SEQ ID NO: 18, 21 and 23.

48. The dimer according to any one of embodiments 1-47, wherein said ISVD specific for CTLA4 comprises a heavy chain variable domain comprising an amino acid sequence as set forth in any one of SEQ ID NO: 20, 22, and 24-32.

49. The dimer according to any one of embodiments 1-48, wherein said ISVD specific for CTLA4 comprises a heavy chain variable domain comprising an amino acid sequence as set forth in SEQ ID NO: 20.

50. The dimer according to any one of embodiments 1-49, which is a homodimer.

51. The dimer according to any one of embodiments 4-50, wherein said linker comprises an amino acid sequence as set forth in any one of SEQ ID NO: 33-34.

52. The dimer according to any one of embodiments 1-51, wherein one or both of said two polypeptide chains comprises an amino acid sequence as set forth in any one of SEQ ID NO: 40-43, 46, 48 and 50.

53. The dimer according to any one of embodiments 1-52, wherein one or both of said two polypeptide chains comprises an amino acid sequence as set forth in SEQ ID NO 40.

54. The dimer according to any one of embodiments 1-53, which is capable of blocking binding of PD-L1 to PD-1.

55. The dimer according to any one of embodiments 1-54, which is capable of blocking binding of PD-L1 to CD80.

56. The dimer according to any one of embodiments 1-55, which is capable of blocking binding of CTLA4 to CD80.

57. The dimer according to any one of embodiments 1-56, which is capable of blocking binding of CTLA4 to CD86.

58. An immunoconjugate, comprising the dimer according to any one of embodiments 1-57.

59. An isolated nucleic acid or isolated nucleic acids encoding the dimer according to any one of embodiments 1-57.

60. A vector or vectors comprising the isolated nucleic acid or isolated nucleic acids according to embodiment 59.

61. An isolated host cell comprising the isolated nucleic acid or isolated nucleic acids according to embodiment 59 or the vector or vectors according to embodiment 60.

62. A method for producing the dimer according to any one of embodiments 1-57, comprising (i) culturing the host cell of embodiment 61 under conditions to effect expression and formation of the dimer, and (ii) harvesting the dimer formed.

63. A pharmaceutical composition comprising an effective amount of the dimer according to any one of embodiments 1-57 or the immunoconjugate of embodiment 58, and optionally a pharmaceutically acceptable excipient.

64. The dimer according to any one of embodiments 1-57, the immunoconjugate of embodiment 58, or the pharmaceutical composition of embodiment 63, for use in the treatment of a cancer in a subject in need thereof.

65. Use of the dimer according to any one of embodiments 1-57 or the immunoconjugate of embodiment 58 in the preparation of a medicament for treating a cancer in a subject in need thereof.

66. A method for treating a cancer in a subject in need thereof, comprising administering to said subject an effective amount of the dimer according to any one of embodiments 1-57 or the immunoconjugate of embodiment 58.

67. A method for blocking binding of CD80 and/or CD86 to CTLA4, comprising administering the dimer according to any one of embodiments 1-57, or the immunoconjugate of embodiment 58.

68. A method for blocking binding of PD1 and/or CD80 to PD-L1, comprising administering the dimer according to any one of embodiments 1-57, or the immunoconjugate of embodiment 58.

69. A method for stimulating secretion of IL-2 by immune cells, comprising administering to said immune cells the dimer according to any one of embodiments 1-57, or the immunoconjugate of embodiment 58.

70. A method for enhancing an immune response in a subject, comprising administering to said subject the dimer according to any one of embodiments 1-57, or the immunoconjugate of embodiment 58.

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1

Protein Preparation

Recombinant DNA Techniques

Standard methods are used to manipulate DNA as described in e.g., Sambrook et al., Molecular cloning: A laboratory manual; Cold Spring Harbor Laboratory Press, Cold Spring Harbor, N.Y., 1989. The molecular biological reagents are used according to the manufacturers' instructions. General information regarding the nucleotide sequences of human immunoglobulins light and heavy chains is given in: Kabat, E. A. et al., (1991) Sequences of Proteins of Immunological Interest, 5th ed., NIH Publication No. 91-3242.

Gene Synthesis

Desired gene segments are either generated by PCR using appropriate templates or are synthesized from synthetic oligonucleotides and PCR products by automated gene synthesis. Such gene synthesis is commercially available from, e.g., Invitrogen (Life Technologies, Inc. Carlsbad, Calif.) and Geneart AG (Regensburg, Germany). The gene segments flanked by singular restriction endonuclease cleavage sites are cloned into standard cloning/sequencing vectors. The plasmid DNA is purified from transformed bacteria and concentration determined by UV spectroscopy. The DNA sequence of the subcloned gene fragments is confirmed by DNA sequencing. Gene segments are designed with suitable restriction sites to allow sub-cloning into the respective expression vectors.

1.1 The ISVDs Specific for CTLA4

The following ISVDs specific for CTLA4 were recombinantly generated, according to the amino acid sequences described below.

Among the ISVDs specific for CTLA4, CTLA4 ISVD-13 and CTLA4 ISVD-C1 have the same CDR1 sequence and the same CDR3 sequence, and they are slightly different in the CDR2 region.

The humanized variants of CTLA4 ISVD-C1 and CTLA4 ISVD-13 were prepared using protein resurfacing method and grafting CDRs to a universal framework of VHH. Briefly, the software Modeller9 was used for modeling of CTLA4 ISVD-C1 and CTLA4 ISVD-13, respectively, the reference antibody used was antibody cAb-Lys3 (PDB number: 1XFP) and their relative solvent accessibility was calculated. The humanized variants were generated by substituting one or more amino acids in CTLA4 ISVD-C1 or CTLA4 ISVD-13 predicted to be exposed to the solvent.

CTLA4 ISVD-C1 comprises a heavy chain variable domain, comprising an HCDR1 with the amino acid sequence as set forth in SEQ ID NO: 17, an HCDR2 with the amino acid sequence as set forth in SEQ ID NO: 21, and an HCDR3 with the amino acid sequence as set forth in SEQ ID NO: 19. CTLA4 ISVD-C1 comprises the amino acid sequence as set forth in SEQ ID NO: 22.

CTLA4 ISVD-31 is a humanized variant of CTLA4 ISVD-C 1. CTLA4 ISVD-31 comprises a heavy chain variable domain, comprising an HCDR1 with the amino acid sequence as set forth in SEQ ID NO: 17, an HCDR2 with the amino acid sequence as set forth in SEQ ID NO: 18, and an HCDR3 with the amino acid sequence as set forth in SEQ ID NO: 19. CTLA4 ISVD-31 comprises the amino acid sequence as set forth in SEQ ID NO: 30.

CTLA4 ISVD-32 is another humanized variant of CTLA4 ISVD-C1. CTLA4 ISVD-32 comprises a heavy chain variable domain, comprising an HCDR1 with the amino acid sequence as set forth in SEQ ID NO: 17, an HCDR2 with the amino acid sequence as set forth in SEQ ID NO: 18, and an HCDR3 with the amino acid sequence as set forth in SEQ ID NO: 19. CTLA4 ISVD-32 comprises the amino acid sequence as set forth in SEQ ID NO: 31.

CTLA4 ISVD-33 is another humanized variant of CTLA4 ISVD-C1. CTLA4 ISVD-33 comprises a heavy chain variable domain, comprising an HCDR1 with the amino acid sequence as set forth in SEQ ID NO: 17, an HCDR2 with the amino acid sequence as set forth in SEQ ID NO: 18, and an HCDR3 with the amino acid sequence as set forth in SEQ ID NO: 19. CTLA4 ISVD-33 comprises the amino acid sequence as set forth in SEQ ID NO: 32.

CTLA4 ISVD-34 is another humanized variant of CTLA4 ISVD-C1. CTLA4 ISVD-34 comprises a heavy chain variable domain, comprising an HCDR1 with the amino acid sequence as set forth in SEQ ID NO: 17, an HCDR2 with the amino acid sequence as set forth in SEQ ID NO: 18, and an HCDR3 with the amino acid sequence as set forth in SEQ ID NO: 19. CTLA4 ISVD-34 comprises the amino acid sequence as set forth in SEQ ID NO: 20.

CTLA4 ISVD-13 comprises a heavy chain variable domain, comprising an HCDR1 with the amino acid sequence as set forth in SEQ ID NO: 17, an HCDR2 with the amino acid sequence as set forth in SEQ ID NO: 23, and an HCDR3 with the amino acid sequence as set forth in SEQ ID NO: 19. CTLA4 ISVD-13 comprises the amino acid sequence as set forth in SEQ ID NO: 24.

CTLA4 ISVD-26 is a humanized variant of CTLA4 ISVD-13. CTLA4 ISVD-26 comprises a heavy chain variable domain, comprising an HCDR1 with the amino acid sequence as set forth in SEQ ID NO: 17, an HCDR2 with the amino acid sequence as set forth in SEQ ID NO: 23, and an HCDR3 with the amino acid sequence as set forth in SEQ ID NO: 19. CTLA4 ISVD-26 comprises the amino acid sequence as set forth in SEQ ID NO: 25.

CTLA4 ISVD-27 is another humanized variant of CTLA4 ISVD-13. CTLA4 ISVD-27 comprises a heavy chain variable domain, comprising an HCDR1 with the amino acid sequence as set forth in SEQ ID NO: 17, an HCDR2 with the amino acid sequence as set forth in SEQ ID NO: 23, and an HCDR3 with the amino acid sequence as set forth in SEQ ID NO: 19. CTLA4 ISVD-27 comprises the amino acid sequence as set forth in SEQ ID NO: 26.

CTLA4 ISVD-28 is another humanized variant of CTLA4 ISVD-13. CTLA4 ISVD-28 comprises a heavy chain variable domain, comprising an HCDR1 with the amino acid sequence as set forth in SEQ ID NO: 17, an HCDR2 with the amino acid sequence as set forth in SEQ ID NO: 23, and an HCDR3 with the amino acid sequence as set forth in SEQ ID NO: 19. CTLA4 ISVD-28 comprises the amino acid sequence as set forth in SEQ ID NO: 27.

CTLA4 ISVD-29 is another humanized variant of CTLA4 ISVD-13. CTLA4 ISVD-29 comprises a heavy chain variable domain, comprising an HCDR1 with the amino acid sequence as set forth in SEQ ID NO: 17, an HCDR2 with the amino acid sequence as set forth in SEQ ID NO: 23, and an HCDR3 with the amino acid sequence as set forth in SEQ ID NO: 19. CTLA4 ISVD-29 comprises the amino acid sequence as set forth in SEQ ID NO: 28.

CTLA4 ISVD-30 is another humanized variant of CTLA4 ISVD-13. CTLA4 ISVD-30 comprises a heavy chain variable domain, comprising an HCDR1 with the amino acid sequence as set forth in SEQ ID NO: 17, an HCDR2 with the amino acid sequence as set forth in SEQ ID NO: 23, and an HCDR3 with the amino acid sequence as set forth in SEQ ID NO: 19. CTLA4 ISVD-30 comprises the amino acid sequence as set forth in SEQ ID NO: 29.

The CDR sequences are defined by combining the Kabat definition and the Chothia definition.

1.2 The ISVDs Specific for PD-L1

The following ISVDs specific for PD-L1 were recombinantly generated, according to the amino acid sequences described below.

The amino acid sequence of PD-L1 ISVD-6 (especially in the CDR3 region) is highly similar to that of PD-L1 ISVD-4 and the humanized variants thereof. The CDR1 and CDR3 of PD-L1 ISVD-m3 are identical to that of PD-L1 ISVD-4, however, its CDR2 region is quite different from that of PD-L1 ISVD-4.

The humanized variants of PD-L1 ISVD-4 were prepared using protein resurfacing method and grafting CDRs to a universal framework of VHH. Briefly, the software Modeller9 was used for modeling of PD-L1 ISVD-4, the reference antibody used was antibody cAb-Lys3 (PDB number: 1XFP) and its relative solvent accessibility was calculated. The humanized variants were generated by substituting one or more amino acids in PD-L1 ISVD-4 predicted to be exposed to the solvent.

PD-L1 ISVD-4 comprises a heavy chain variable domain, comprising an HCDR1 with the amino acid sequence as set forth in SEQ ID NO: 3, an HCDR2 with the amino acid sequence as set forth in SEQ ID NO: 4, and an HCDR3 with the amino acid sequence as set forth in SEQ ID NO: 5. PD-L1 ISVD-4 comprises the amino acid sequence as set forth in SEQ ID NO: 13.

PD-L1 ISVD-9 is a humanized variant of PD-L1 ISVD-4. PD-L1 ISVD-9 comprises a heavy chain variable domain, comprising an HCDR1 with the amino acid sequence as set forth in SEQ ID NO: 3, an HCDR2 with the amino acid sequence as set forth in SEQ ID NO: 4, and an HCDR3 with the amino acid sequence as set forth in SEQ ID NO: 5. PD-L1 ISVD-9 comprises the amino acid sequence as set forth in SEQ ID NO: 6.

PD-L1 ISVD-11 is another humanized variant of PD-L1 ISVD-4. PD-L1 ISVD-11 comprises a heavy chain variable domain, comprising an HCDR1 with the amino acid sequence as set forth in SEQ ID NO: 3, an HCDR2 with the amino acid sequence as set forth in SEQ ID NO: 4, and an HCDR3 with the amino acid sequence as set forth in SEQ ID NO: 5. PD-L1 ISVD-11 comprises the amino acid sequence as set forth in SEQ ID NO: 14.

PD-L1 ISVD-13 is another humanized variant of PD-L1 ISVD-4. PD-L1 ISVD-13 comprises a heavy chain variable domain, comprising an HCDR1 with the amino acid sequence as set forth in SEQ ID NO: 3, an HCDR2 with the amino acid sequence as set forth in SEQ ID NO: 4, and an HCDR3 with the amino acid sequence as set forth in SEQ ID NO: 5. PD-L1 ISVD-13 comprises the amino acid sequence as set forth in SEQ ID NO: 15.

PD-L1 ISVD-6 comprises a heavy chain variable domain, comprising an HCDR1 with the amino acid sequence as set forth in SEQ ID NO: 7, an HCDR2 with the amino acid sequence as set forth in SEQ ID NO: 8, and an HCDR3 with the amino acid sequence as set forth in SEQ ID NO: 9. PD-L1 ISVD-6 comprises the amino acid sequence as set forth in SEQ ID NO: 10.

PD-L1 ISVD-m3 comprises a heavy chain variable domain, comprising an HCDR1 with the amino acid sequence as set forth in SEQ ID NO: 3, an HCDR2 with the amino acid sequence as set forth in SEQ ID NO: 11, and an HCDR3 with the amino acid sequence as set forth in SEQ ID NO: 5. PD-L1 ISVD-m3 comprises the amino acid sequence as set forth in SEQ ID NO: 12.

The CDR sequences are defined by combining the Kabat definition and the Chothia definition.

1.3 Generating the Dimer of the Present Disclosure

As examples, the following dimers of the present disclosure were generated: aPDL1.9-aCTLA4.34-Fc, aPDL1.9-L-aCTLA4.34-Fc, aCTLA4.34-aPDL1.9-Fc, aCTLA4.34-L-aPDL1.9-Fc, aPDL1.6-aCTLA4.34-Fc, aPDL1.m3-aCTLA4.34-Fc and aPDL1.9-aCTLA4.13-Fc.

The amino acid sequence of human IgGl-Fc region with hinge (SEQ ID NO:35 or 38) was obtained based on the constant region amino acid sequence of human immunoglobulin gammal (IgGl) from the protein database Uniprot (P01857) (SEQ ID NO: 36). The corresponding DNA sequence encoding it was then designed using online tool DNAworks (helixweb.nih.gov/dnaworks/).

For aPDL1.9-aCTLA4.34-Fc, the PD-L1 ISVD-9 of Example 1.2 was fused to the N-terminus of CTLA4 ISVD-34 of Example 1.1 via a short linker GAP (SEQ ID NO:33) to obtain the bi-specific binding moiety aPDL1.9-aCTLA4.34. The aPDL1.9-aCTLA4.34 was then fused to the N-terminal amino acid of the human IgGl-Fc region with hinge to obtain aPDL1.9-aCTLA4.34-Fc, which comprises an amino acid sequence as set forth in SEQ ID NO: 40.

For aPDL1.9-L-aCTLA4.34-Fc, the PD-L1 ISVD-9 of Example 1.2 was fused to the N-terminus of CTLA4 ISVD-34 of Example 1.1 via a longer linker GGGGSGGGGSGGGGS (SEQ ID NO:34) to obtain the bi-specific binding moiety aPDL1.9-L-aCTLA4.34. The aPDL1.9-L-aCTLA4.34 was then fused to the N-terminal amino acid of the human IgGl-Fc region with hinge to obtain aPDL1.9-L-aCTLA4.34-Fc, which comprises an amino acid sequence as set forth in SEQ ID NO: 41.

For aCTLA4.34-aPDL1.9-Fc, the CTLA4 ISVD-34 of Example 1.1 was fused to the N-terminus of PD-L1 ISVD-9 of Example 1.2 via a short linker GAP (SEQ ID NO:33) to obtain the bi-specific binding moiety aCTLA4.34-aPDL1.9. The aCTLA4.34-aPDL1.9 was then fused to the N-terminal amino acid of the human IgGl-Fc region with hinge to obtain aCTLA4.34-aPDL1.9-Fc, which comprises an amino acid sequence as set forth in SEQ ID NO: 42.

For aCTLA4.34-L-aPDL1.9-Fc, the CTLA4 ISVD-34 of Example 1.1 was fused to the N-terminus of PD-L1 ISVD-9 of Example 1.2 via a longer linker GGGGSGGGGSGGGGS (SEQ ID NO:34) to obtain the bi-specific binding moiety aCTLA4.34-L-aPDL1.9. The aCTLA4.34-L-aPDL1.9 was then fused to the N-terminal amino acid of the human IgGl-Fc region with hinge to obtain aCTLA4.34-L-aPDL1.9-Fc, which comprises an amino acid sequence as set forth in SEQ ID NO: 43.

For aPDL1.6-aCTLA4.34-Fc, the PD-L1 ISVD-6 of Example 1.2 was fused to the N-terminus of CTLA4 ISVD-34 of Example 1.1 via a short linker GAP (SEQ ID NO:33) to obtain the bi-specific binding moiety aPDL1.6-aCTLA4.34. The aPDL1.6-aCTLA4.34 was then fused to the N-terminal amino acid of the human IgGl-Fc region with hinge to obtain aPDL1.6-aCTLA4.34-Fc, which comprises an amino acid sequence as set forth in SEQ ID NO: 46.

For aPDL1.m3-aCTLA4.34-Fc, the PD-L1 ISVD-m3 of Example 1.2 was fused to the N-terminus of CTLA4 ISVD-34 of Example 1.1 via a short linker GAP (SEQ ID NO:33) to obtain the bi-specific binding moiety aPDL1.m3-aCTLA4.34. The aPDL1.m3-aCTLA4.34 was then fused to the N-terminal amino acid of the human IgGl-Fc region with hinge to obtain aPDL1.m3-aCTLA4.34-Fc, which comprises an amino acid sequence as set forth in SEQ ID NO: 48.

For aPDL1.9-aCTLA4.13-Fc, the PD-L1 ISVD-9 of Example 1.2 was fused to the N-terminus of CTLA4 ISVD-13 of Example 1.1 via a short linker GAP (SEQ ID NO:33) to obtain the bi-specific binding moiety aPDL1.9-aCTLA4.13. The aPDL1.9-aCTLA4.13 was then fused to the N-terminal amino acid of the human IgGl-Fc region with hinge to obtain aPDL1.9-aCTLA4.13-Fc, which comprises an amino acid sequence as set forth in SEQ ID NO: 50.

1.4 Generating Control Molecules

As a control, dAb was prepared, which is a non-functional single domain polypeptide (with no function in either wild-type or double knockout mice), comprising an amino acid sequence as set forth in SEQ ID NO: 37.

The amino acid sequence of human IgG1-Fc region with hinge (SEQ ID NO:35 or 38) was obtained based on the constant region amino acid sequence of human immunoglobulin gammal (IgG1) from the protein database Uniprot (P01857) (SEQ ID NO: 36). The corresponding DNA sequence encoding it was then designed using online tool DNAworks (helixweb.nih.gov/dnaworks/).

Then, the following control dimers were prepared: aPDL1.9-dAb-Fc, dAb-aCTLA4.34-Fc, aPDL1.6-dAb-Fc, aPDL1.m3-dAb-Fc, and dAb-aCTLA4.13-Fc.

In aPDL1.9-dAb-Fc, the PD-L1 ISVD-9 of Example 1.2 was fused to the N-terminus of the control dAb via a short linker GAP (SEQ ID NO:33) to obtain aPDL1.9-dAb. The aPDL1.9-dAb was then fused to the N-terminal amino acid of the human IgG1-Fc region with hinge to obtain aPDL1.9-dAb-Fc, which comprises an amino acid sequence as set forth in SEQ ID NO: 44.

In aPDL1.6-dAb-Fc, the PD-L1 ISVD-6 of Example 1.2 was fused to the N-terminus of the control dAb via a short linker GAP (SEQ ID NO:33) to obtain aPDL1.6-dAb. The aPDL1.6-dAb was then fused to the N-terminal amino acid of the human IgG1-Fc region with hinge to obtain aPDL1.6-dAb-Fc, which comprises an amino acid sequence as set forth in SEQ ID NO: 47.

In aPDL1.m3-dAb-Fc, the PD-L1 ISVD-m3 of Example 1.2 was fused to the N-terminus of the control dAb via a short linker GAP (SEQ ID NO:33) to obtain aPDL1.m3-dAb. The aPDL1.m3-dAb was then fused to the N-terminal amino acid of the human IgG1-Fc region with hinge to obtain aPDL1.m3-dAb-Fc, which comprises an amino acid sequence as set forth in SEQ ID NO: 49.

In dAb-aCTLA4.34-Fc, the control dAb was fused to the N-terminus of CTLA4 ISVD-34 of Example 1.1 via a short linker GAP (SEQ ID NO:33) to obtain dAb-aCTLA4.34. The dAb-aCTLA4.34 was then fused to the N-terminal amino acid of the human IgG1-Fc region with hinge to obtain dAb-aCTLA4.34-Fc, which comprises an amino acid sequence as set forth in SEQ ID NO: 45.

In dAb-aCTLA4.13-Fc, the control dAb was fused to the N-terminus of CTLA4 ISVD-13 of Example 1.1 via a short linker GAP (SEQ ID NO:33) to obtain dAb-aCTLA4.13. The dAb-aCTLA4.13 was then fused to the N-terminal amino acid of the human IgG1-Fc region with hinge to obtain dAb-aCTLA4.13-Fc, which comprises an amino acid sequence as set forth in SEQ ID NO: 51.

FIG. 1, Panels A and B, provide examples of the dimer of the present disclosure, wherein 1 indicates the ISVD specific for PD-L1, 2 indicates the ISVD specific for CTLA4, 3 indicates the Fc domain comprising the Fc subunits, and 4 indicates the bi-specific binding moiety.

1.5 Expression and Purification

The nucleic acid sequences encoding aPDL1.9-aCTLA4.34-Fc, aPDL1.9-L-aCTLA4.34-Fc, aCTLA4.34-aPDL1.9-Fc, aCTLA4.34-L-aPDL1.9-Fc, aPDL1.6-aCTLA4.34-Fc, aPDL1.m3-aCTLA4.34-Fc, aPDL1.9-aCTLA4. 13-Fc, aPDL1.9-dAb-Fc, dAb-aCTLA4.34-Fc, aPDL1.6-dAb-Fc, aPDL1.m3-dAb-Fc, or dAb-aCTLA4.13-Fc described in Examples 1.3 and 1.4 above were cloned into the expression vector pCDNA4 (Invitrogen, Cat V86220), to obtain corresponding recombinant expression vectors, respectively.

Then, HEK293 cells were transfected with these recombinant expression vectors for recombinant protein expression. Briefly, the plasmids were diluted with the Freestyle293 culture medium, wherein a PEI (Polyethylenimine) solution was added. Each plasmid/PEI solution was added into an HEK293 cell suspension, and cultured under 37° C., 10% $CO_2$, 90 rpm for 5-6 days. Supernatant fluid was harvested and purified using protein A affinity chromatography, to obtain the purified recombinant protein dimers or control molecules, respectively: aPDL1.9-aCTLA4.34-Fc, aPDL1.9-L-aCTLA4.34-Fc, aCTLA4.34-aPDL1.9-Fc, aCTLA4.34-L-aPDL 1.9-Fc, aPDL 1.6-aCTLA4.34-Fc, aPDL1.m3-aCTLA4.34-Fc, aPDL 1.9-aCTLA4.13-Fc, aPDL1.9-dAb-Fc, dAb-aCTLA4.34-Fc, aPDL1.6-dAb-Fc, aPDL 1.m3-dAb-Fc, and dAb -aCTLA4.13-Fc.

As examples, the yield of dimers aPDL1.9-aCTLA4.34-Fc, aPDL1.9-L-aCTLA4.34-Fc, aCTLA4.34-aPDL1.9-Fc and aCTLA4.34-L-aPDL1.9-Fc, and controls aPDL1.9-dAb-Fc and dAb-aCTLA4.34-Fc were examined, and the results are shown in Table 2.

TABLE 2

The expression of the dimers and control molecules

| Protein | Yield (mg/L) | SE-HPLC Main peak (%) |
|---|---|---|
| aPDL1.9-aCTLA4.34-Fc | 385 | 98.5 |
| aPDL1.9-L-aCTLA4.34-Fc | 360 | 98.9 |
| aCTLA4.34-aPDL1.9-Fc | 320 | 98.6 |
| aCTLA4.34-L-aPDL1.9-Fc | 372 | 98.6 |
| aPDL1.9-dAb-Fc | 300 | 96.7 |
| dAb-aCTLA4.34-Fc | 280 | 98.1 |

Example 2

Binding Activities 2.1 Methods
2.1.1 Binding Affinity to Soluble CTLA4 by ELISA

A 96-well plate was coated with CTLA4-muFc (human CTLA4 extracellular domain fused to the N-terminus of mouse Fc, its amino acid sequence is as set forth in SEQ ID NO: 52). Various concentrations of the samples as well as control molecules were added. HRP labeled goat anti-human Fc antibody was used for detection. After being developed with TMB, the plate was read at a wavelength of 450/650 nm in a microplate reader.

2.1.2 Binding Affinity to Soluble PD-L1 by ELISA

A 96-well plate was coated with PD-L1-muFc (human PD-L1 extracellular domain fused to N-terminus of mouse Fc, its amino acid sequence is as set forth in SEQ ID NO: 53). Various concentrations of the samples as well as control molecules were added. HRP labeled goat anti-human Fc antibody was used for detection. After being developed with TMB, the plate was read at a wavelength of 450/650 nm in a microplate reader.

2.1.3 Binding Affinity to Both Soluble PD-L1 and CTLA4 by Bridging ELISA

A 96-well plate was coated with PD-L1-huFc (human PD-L1 extracellular domain fused to N-terminus of human Fc, its amino acid sequence is as set forth in SEQ ID NO: 54). Various concentrations of the samples as well as control molecules were added. Then, CTLA4-muFcwas used to detect the bound samples, and then HRP labeled goat anti-mouse Fc antibody was used as secondary antibody. After being developed by TMB, the plate was read at a wavelength of 450/650 nm in a microplate reader.

2.1.4 Binding Affinity Tested by SPR

The assays were performed using a Biacore X100. Samples were diluted and immobilized on the surface of a protein A sensor chip at a concentration of 3 nM. CTLA4 containing solution was diluted and prepared at a concentration of 800 nM, 400 nM, 200 nM, 100 nM, and 50 nM respectively. Or if using PD-L1-muFc, it was diluted into 100 nM, 33.3 nM, 11.1 nM, 3.70 nM, 1.23 nM. After association, disassociation and regeneration, the kinetics constants ($K_D$) of binding was measured.

2.1.5 Binding Measured by BLI

The assays were performed using the Fortebio's Octet K2 platform. Samples were diluted and captured using a biosensor at a concentration of 10 μg/ml. PD-L1 containing solution was diluted and prepared at a concentration of 50 nM, 25 nM, 12.5 nM, 6.25 nM, and 3.125 nM respectively. After normalization (baseline), association, disassociation, and regeneration procedures, and kinetics constants ($K_D$s) of binding were gained.

2.1.6 Binding Activity to Membrane Bond Ligands

In Vitro Binding to A375-hPD-L1 Cells

The samples were diluted and prepared at concentrations of 0.091, 0.27, 0.82, 2.45, 7.41, 22.22, 66.67 and 200 μM, respectively. The A375-hPD-L1 cell (A375 cell line with constant expression of human PD-L1 protein, generated with stable transfection of human PD-L1 expression cassette into the A374 cell line) density was adjusted to 4 x10$^6$ cells/ml. After binding and washing procedures, the samples were loaded for flow cytometry analysis in order to measure the median fluorescence intensity (MFI).

In vitro Binding to HEK293-CTLA4 Cell

The samples were diluted to 2 μM (prepared from the stock solution of 1 μM), and then were 5-fold serially diluted with a dilution buffer. The HEK293-CTLA4 cell (HEK293 cell line with transient expression of human CTLA4 protein, which was generated by transiently transfecting the human CTLA4 expression cassette into the HEK293 cell line) density was adjusted to 4×10$^6$ cells/ml. After binding and washing procedures, a total of 8 concentration gradients were tested.

2.2 Results

Figure 2:
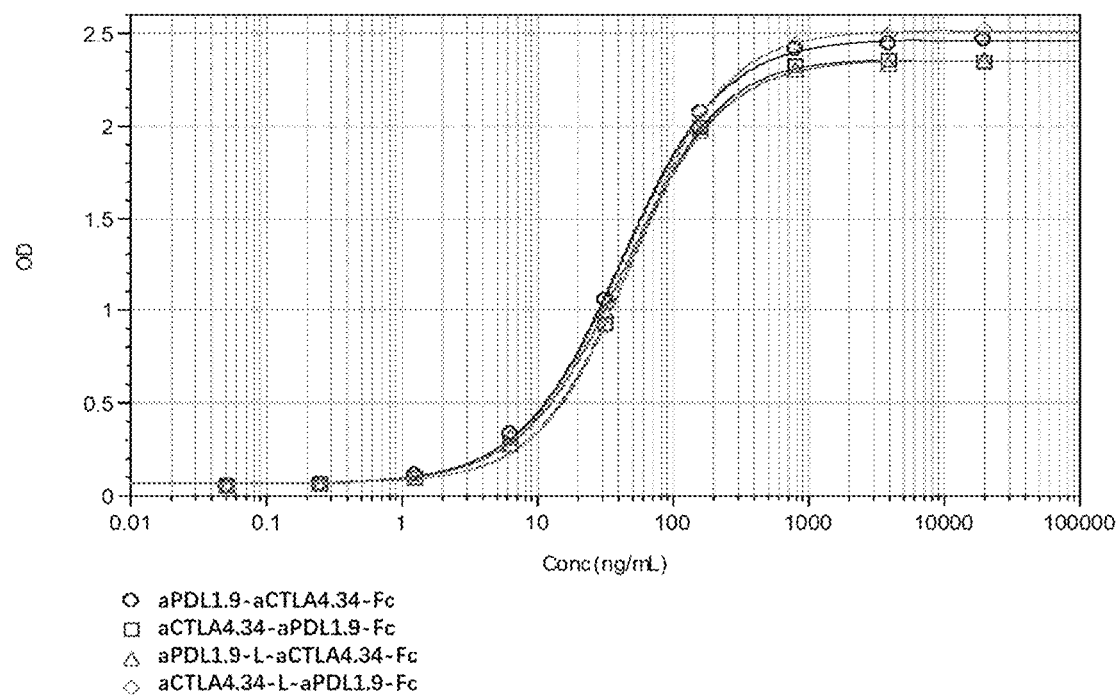
FIG. 2. Panels A-F illustrate binding of the dimers of the present disclosure to CTLA4 or PD-L1. Panels G and H illustrate binding of the dimers of the present disclosure to cells expressing PD-L1 or CTLA4.
Figure 2:
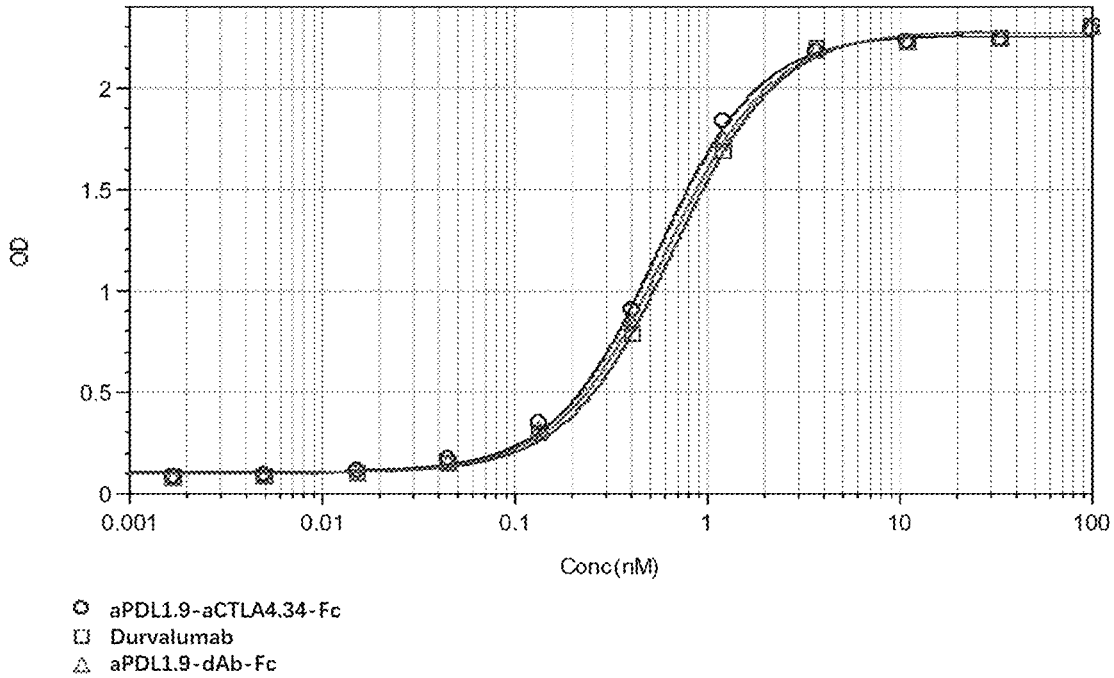
Figure 2:
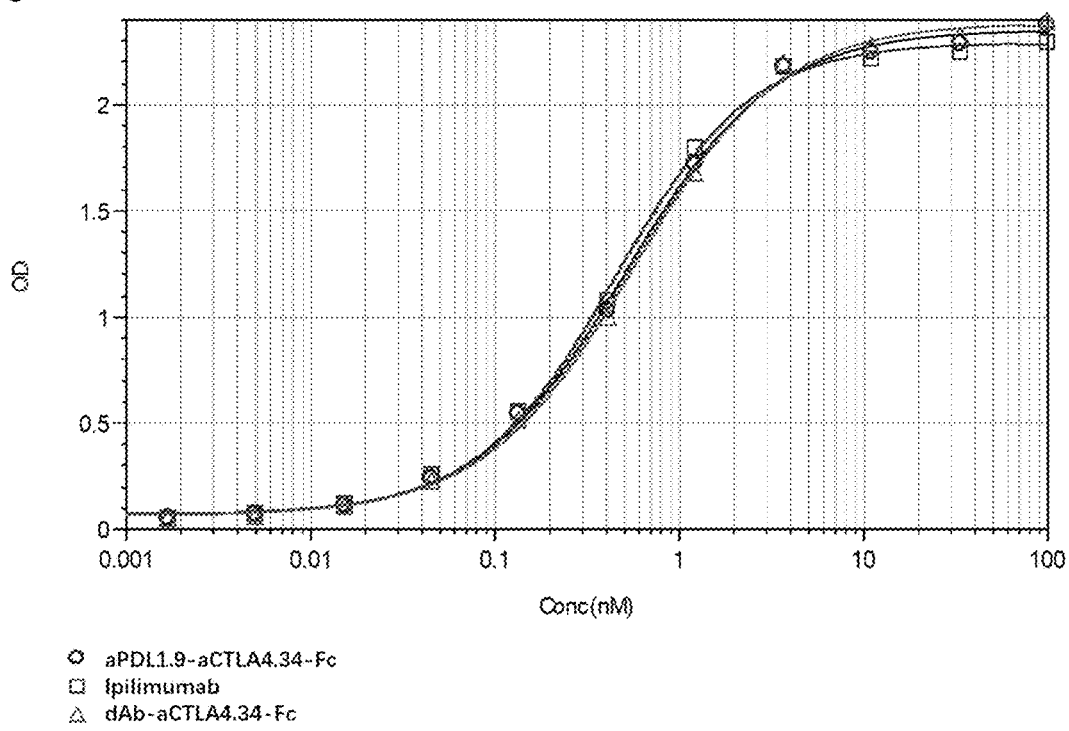
Figure 2:
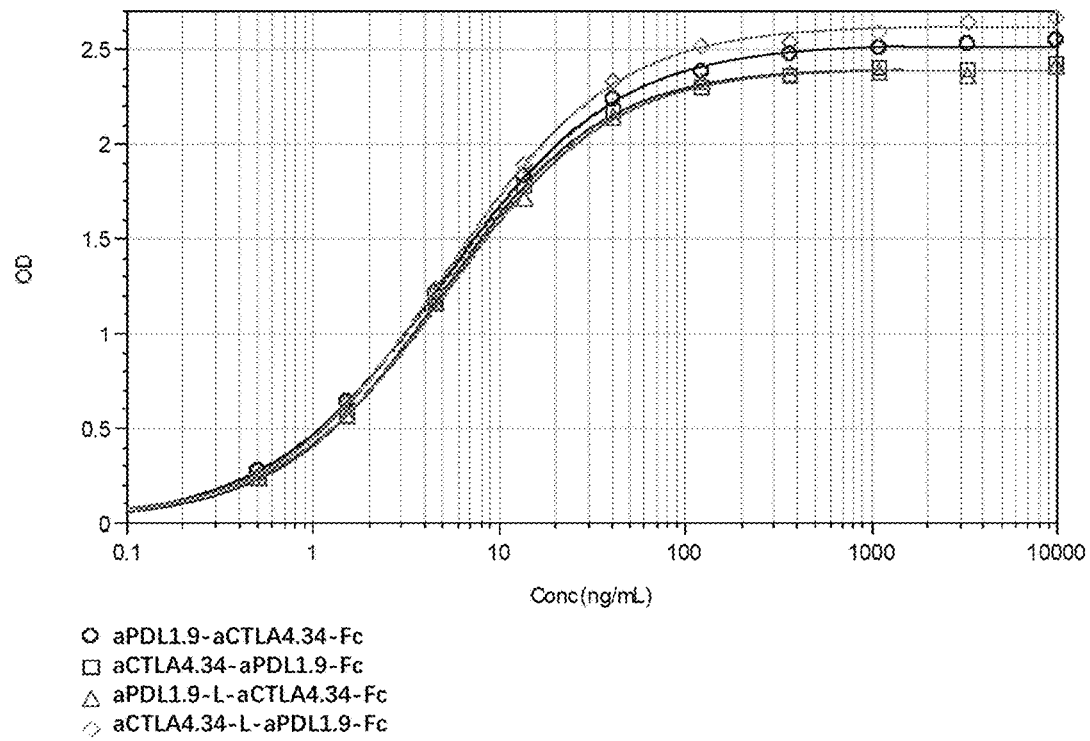
Figure 2:
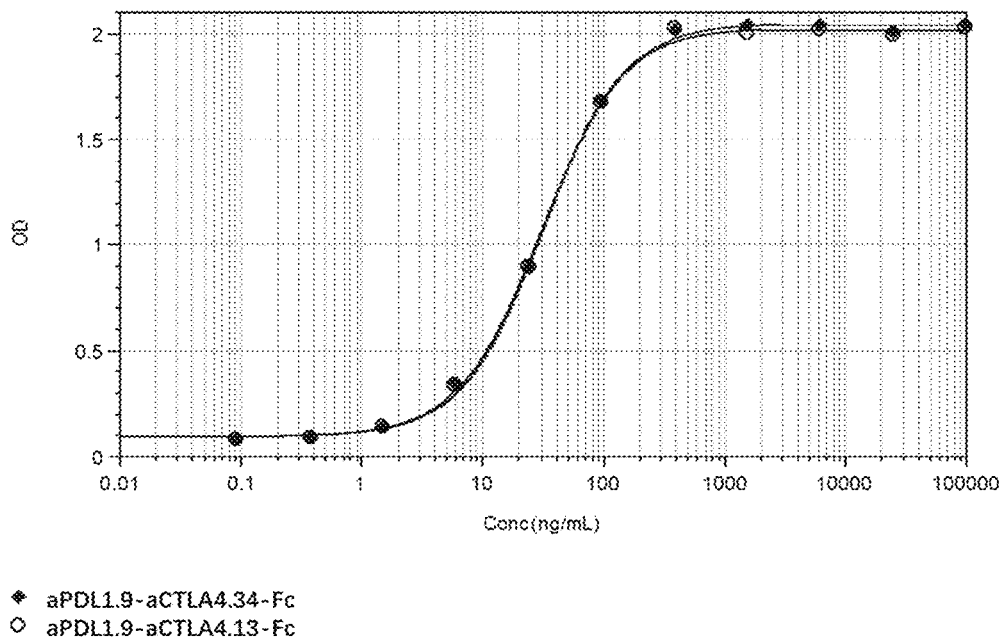
Figure 2:
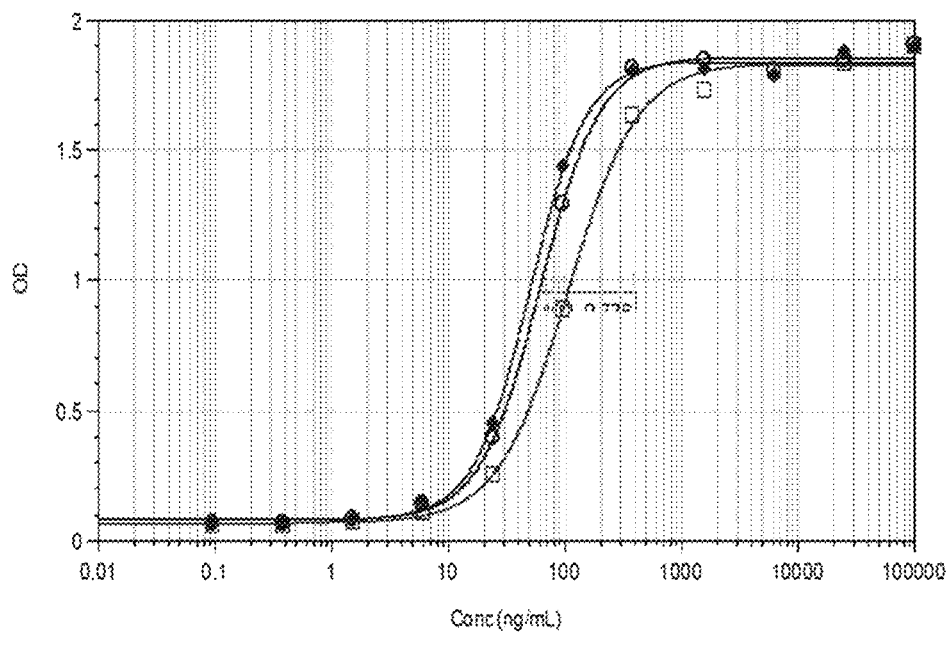
Figure 2:
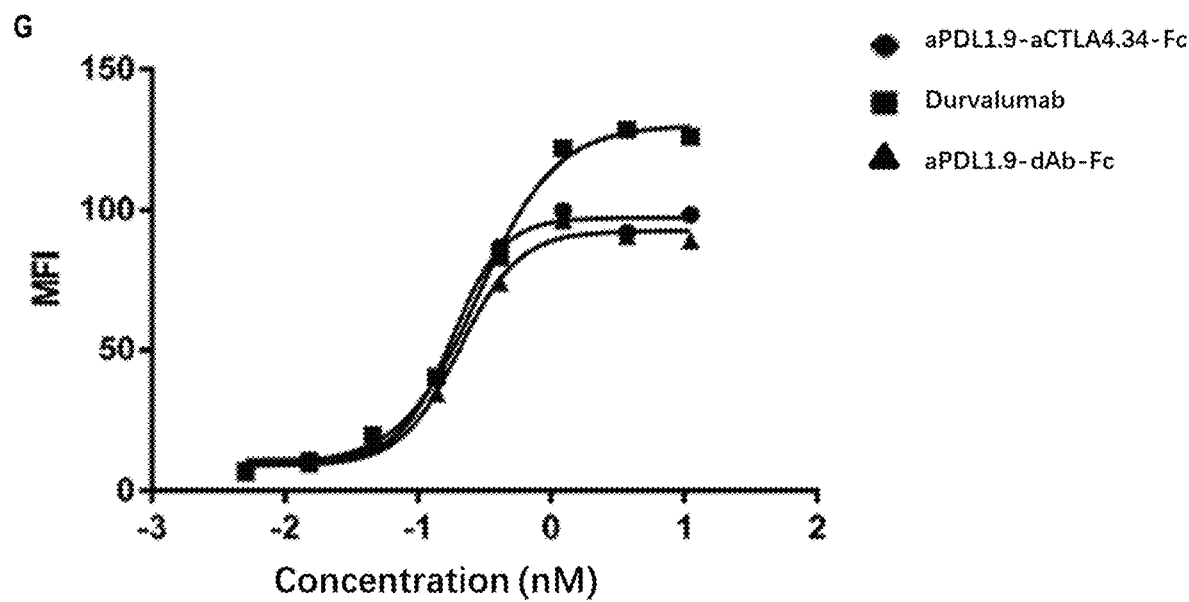
Figure 2:
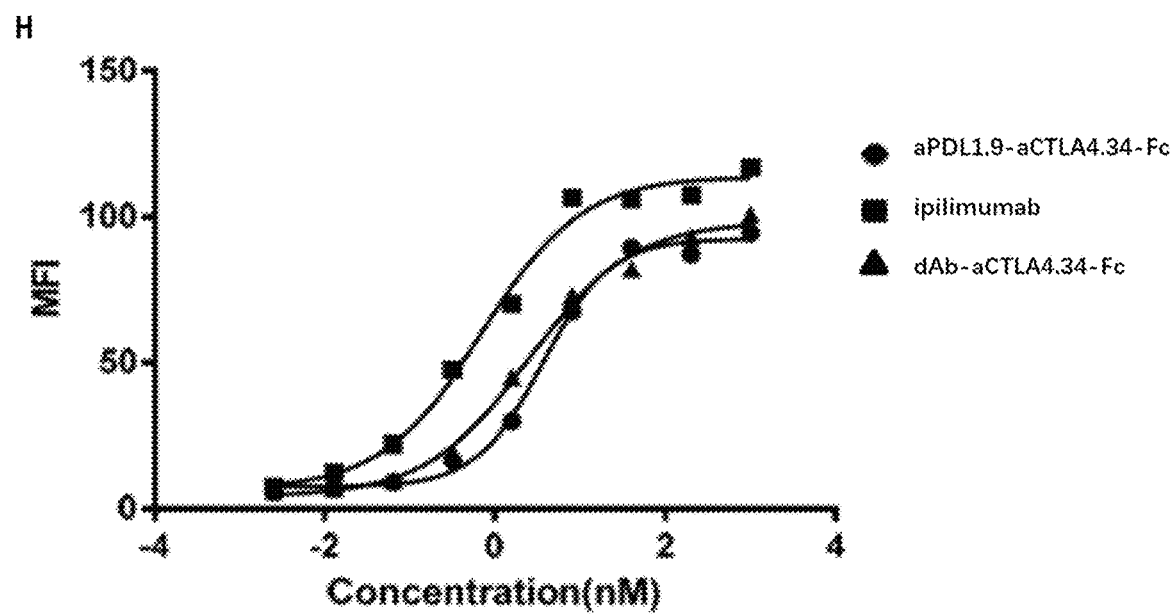

FIG. 2, Panel A shows binding of the dimers of the present disclosure to soluble human CTLA4. It can be seen that either with the ISVD specific for CTLA4 in the N-terminus of the dimer, or with the ISVD specific for PD-L1 in the N-terminus of the dimer, similar binding affinities were observed, e.g., as shown by the $EC_{50}$ value. Similarly, comparable binding affinities were observed when a short linker (e.g., GAP) or a longer linker (e.g., GGGGSGGGGSGGGGS) was used between the ISVD specific for CTLA4 and the ISVD specific for PD-L1. The $EC_{50}$ value was around 40 ng/mL for aPDL1.9-aCTLA4.34-Fc, aCTLA4.34-aPDL1.9-Fc, aPDL1.9-L-aCTLA4.34-Fc and aCTLA4.34-L-aPDL1.9-Fc.

FIG. 2, Panel B shows binding of the dimers of the present disclosure to soluble human PD-L1. The anti-PD-L1 antibody durvalumab (AstraZeneca) was used as a positive control, in addition, aPDL1.9-dAb-Fc was also used as a control, which does not contain any functional CTLA4 targeting moiety.

It can be seen that comparable binding affinities were observed for the dimer of the present disclosure (e.g., aPDL1.9-aCTLA4.34-Fc), the anti-PD-L1 antibody durvalumab and the control molecule aPDL1.9-dAb-Fc, with an $EC_{50}$ value around 0.6 nM.

FIG. 2, Panel C shows binding of the dimers of the present disclosure to soluble human CTLA4. The anti-CTLA4 antibody ipilimumab (Bristol-Myers Squibb) was used as a positive control, in addition, dAb-aCTLA4.34-Fc was also used as a control, which does not contain any functional PD-L1 targeting moiety.

It can be seen that comparable binding affinities were observed for the dimer of the present disclosure (e.g., aPDL1.9-aCTLA4.34-Fc), the anti-CTLA4 antibody ipilimumab and the control molecule dAb-aCTLA4.34-Fc, with an $EC_{50}$ value around 0.5 nM.

FIG. 2, Panel D shows binding of the dimers of the present disclosure to soluble human CTLA4 and soluble PD-L1, as examined with bridging ELISA. It can be seen that either with the ISVD specific for CTLA4 in the N-terminus of the dimer, or with the ISVD specific for PD-L1 in the N-terminus of the dimer, similar binding affinities were observed, e.g., as shown by the $EC_{50}$ value. Similarly, comparable binding affinities were observed when a short linker (e.g., GAP) or a longer linker (e.g., GGGGSGGGGSGGGGS) was used between the ISVD specific for CTLA4 and the ISVD specific for PD-L1. In addition, the results show that the dimers of the present disclosure (e.g., aPDL1.9-aCTLA4.34-Fc, aCTLA4.34-aPDL1.9-Fc, aPDL1.9-L-aCTLA4.34-Fc, aCTLA4.34-L-aPDL1.9-Fc) could bind to both CTLA4 and PD-L1, with comparable binding affinity.

FIG. 2, Panel E shows binding of the dimers of the present disclosure to soluble human CTLA4 and soluble PD-L1, as examined with bridging ELISA. It can be seen that comparable binding affinities were obtained either with CTLA4 ISVD-34 in the dimer or with CTLA4 ISVD-13 in the dimer.

FIG. 2, Panel F shows binding of the dimers of the present disclosure to soluble human CTLA4 and soluble PD-L1, as examined with bridging ELISA. It can be seen that comparable binding affinities were obtained with PD-L1 ISVD-9, PD-L1 ISVD-6, or PD-L1 ISVD-m3 in the dimer, and the $EC_{50}$ value for aPDL1.6-aCTLA4.34-Fc was slightly higher than that of aPDL1.9-aCTLA4.34-Fc or aPDL1.m3-aCTLA4.34-Fc. Interestingly, although PD-L1 ISVD-9 and PD-L1 ISVD-m3 contain almost completely different CDR2 sequences, they behave similarly when employed in the dimers of the present disclosure, indicating that the CDR2 sequence might not be critical for the function of the dimers.

The binding activity of the dimers of the present disclosure (e.g., aPDL1.9-aCTLA4.34-Fc) to PD-L1 or CTLA4 expressed on cell surfaces was also examined, and was compared to that of control molecules (e.g., durvalumab, ipilimumab, aPDL1.9-dAb-Fc, or dAb-aCTLA4.34-Fc). The results are shown in FIG. 2, Panels G and H.

FIG. 2, Panel G shows that the dimer of the present disclosure (e.g., aPDL1.9-aCTLA4.34-Fc) could bind to A375-hPDL1 cells with similar $EC_{50}$ value as durvalumab and aPDL1.9-dAb-Fc.

FIG. 2, Panel H shows that the dimer of the present disclosure (e.g., aPDL1.9-aCTLA4.34-Fc) could bind to HEK293-CTLA4 cells with similar $EC_{50}$ value as dAb-aCTLA4.34-Fc. However, the dimer of the present disclosure (e.g., aPDL1.9-aCTLA4.34-Fc) binds to HEK293-CTLA4 cells with a higher $EC_{50}$ value than ipilimumab, indicating a decreased binding affinity to cell-surface CTLA4. These results indicate that the dimers of the present disclosure may have a lower toxicity than ipilimumab.

Example 3

Blocking Potency 3.1 Methods
3.1.1 Blocking Potency for the Binding of PD-L1 to PD1 or CD80

The abilities of the dimers of the present disclosure in blocking binding of PD-L1 to PD1 or CD80 were evaluated by competition ELISA.

Briefly, a 96-well plate was coated with 3 μg/ml of PD-L1-huFc (SEQ ID NO: 54). Then a mixture of PD1-muFc (SEQ ID NO: 58) and the dimers of the present disclosure, or a mixture of CD80-muFc (SEQ ID NO: 55) and the dimers of the present disclosure was added to the PD-L1-huFc coated plate. The concentration of PD1-muFc used was 10 μg/ml, and the concentration of CD80-muFc was 100 μg/ml. The dimers of the present disclosure were serially diluted. HRP labeled goat anti-mouse IgG1 antibody was used to detect the bound PD1-muFc or CD80-muFc, the amount of which shall be reverse-correlated with the blocking potency of the dimers of the present disclosure. After being developed with TMB, the plate was read at a wavelength of 450/650 nm in a microplate reader. Durvalumab was used as a positive control.

3.1.2 Blocking Potency for the Binding of CTLA4 to CD80 or CD86

The abilities of the dimers of the present disclosure in blocking binding of CTLA4 to CD80 or CD86 were evaluated by competition ELISA.

Briefly, a 96-well plate was coated with 3 μg/ml of CTLA4-huFc (SEQ ID NO: 56). Then a mixture of CD80-muFc (SEQ ID NO: 55) and the dimers of the present disclosure, or a mixture of CD86-muFc (SEQ ID NO: 57) and the dimers of the present disclosure was added to the CTLA4-huFc coated plate. The dimers of the present disclosure were serially diluted. HRP labeled goat anti-mouse IgG1 antibody was used to detect the bound CD86-muFc or CD80-muFc. After being developed with TMB, the plate was read at a wavelength of 450/650 nm in a microplate reader. Ipilimumab was used as a positive control.

3.2 Results

Figure 3:
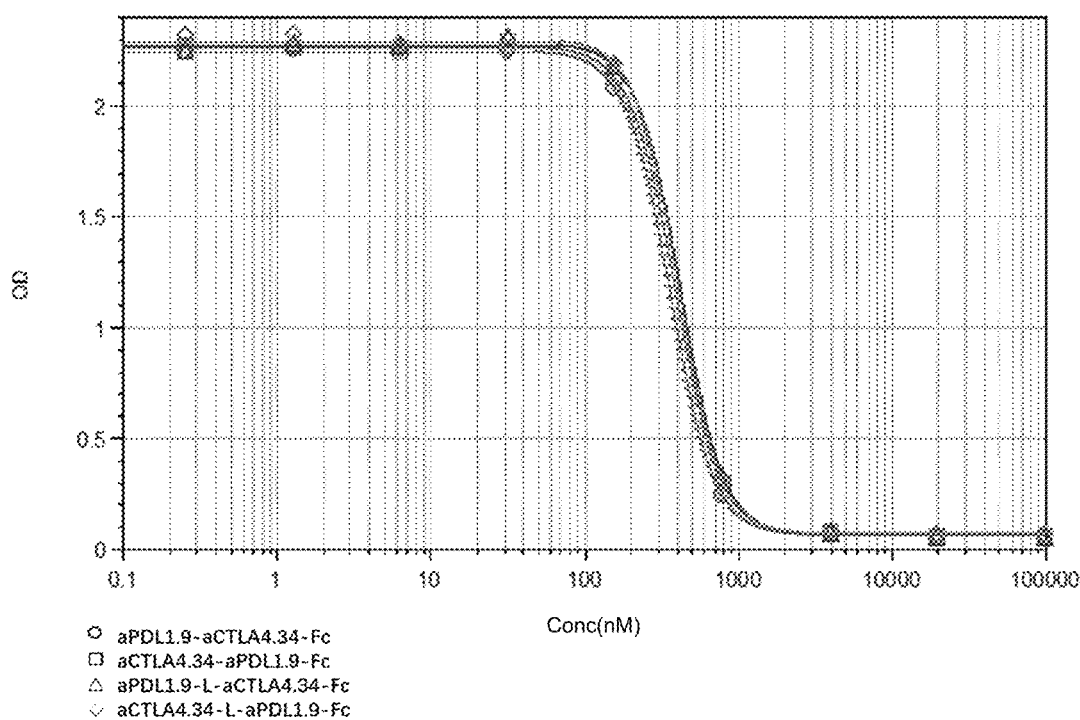
FIG. 3. Panels A and B illustrate the effect of the dimers of the present disclosure in blocking binding of PD1 to PD-L1. Panel C illustrates the effect of the dimers of the present disclosure in blocking binding of CD80 to PD-L1. Panels D and E illustrate the effect of the dimers of the present disclosure in blocking binding of CTLA4 to CD80. Panel F illustrates the effect of the dimers of the present disclosure in blocking binding of CTLA4 to CD86.
Figure 3:
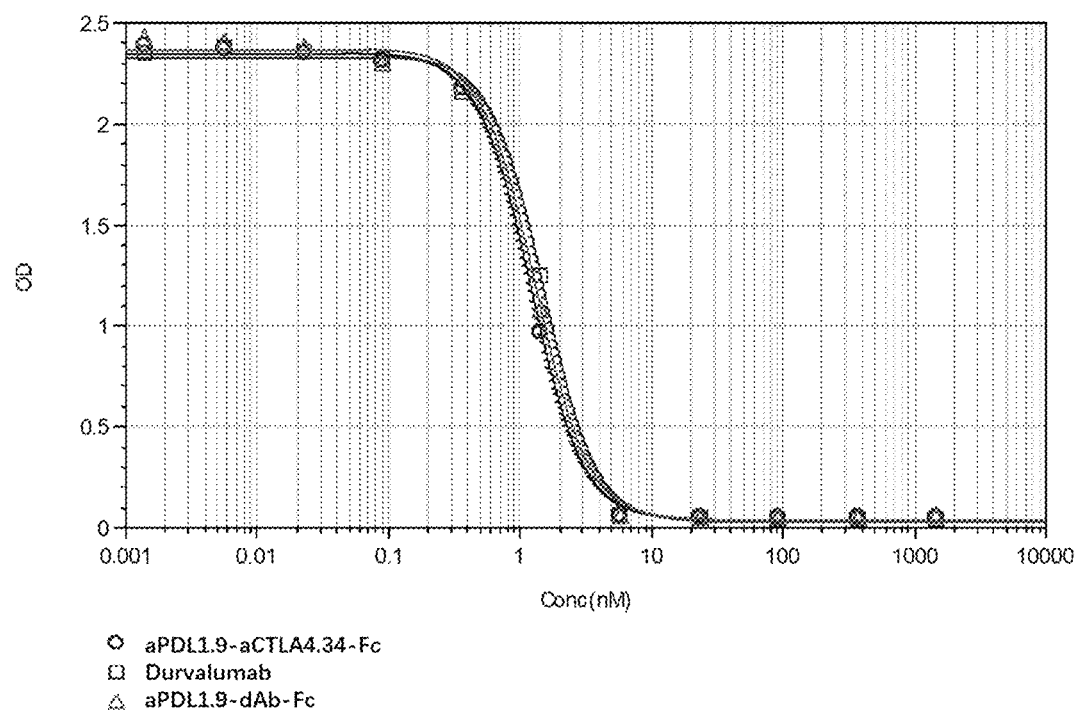
Figure 3:
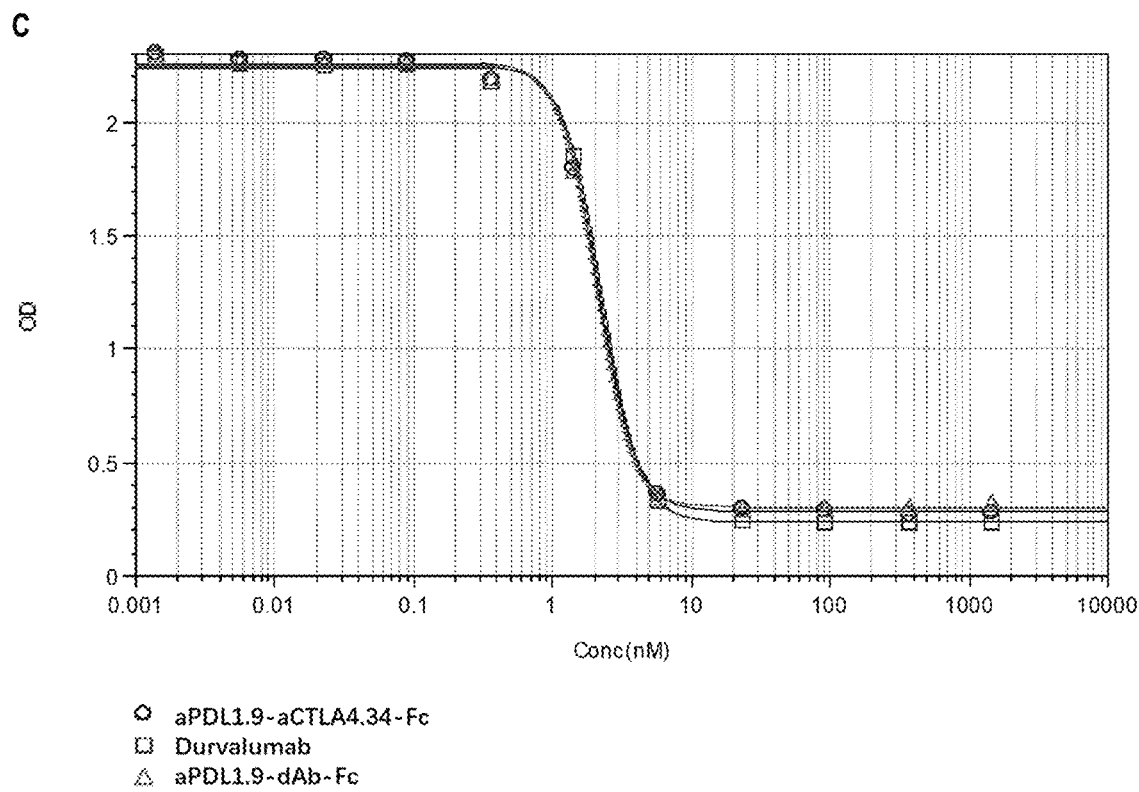
Figure 3:
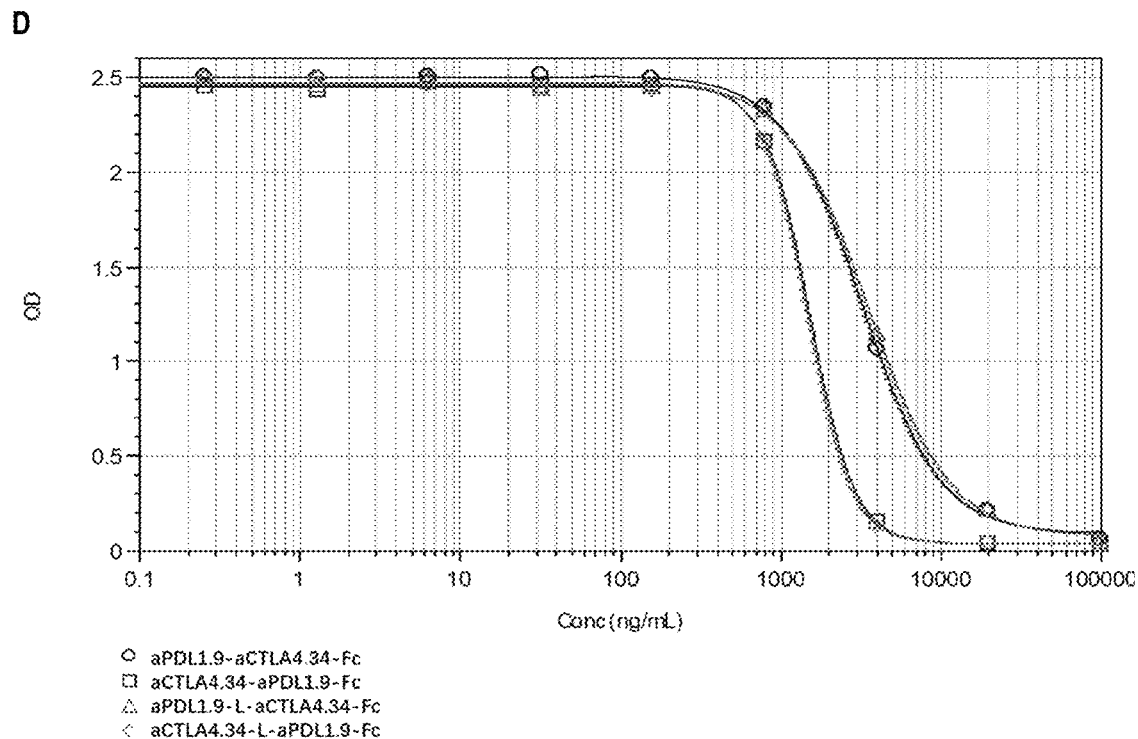
Figure 3:
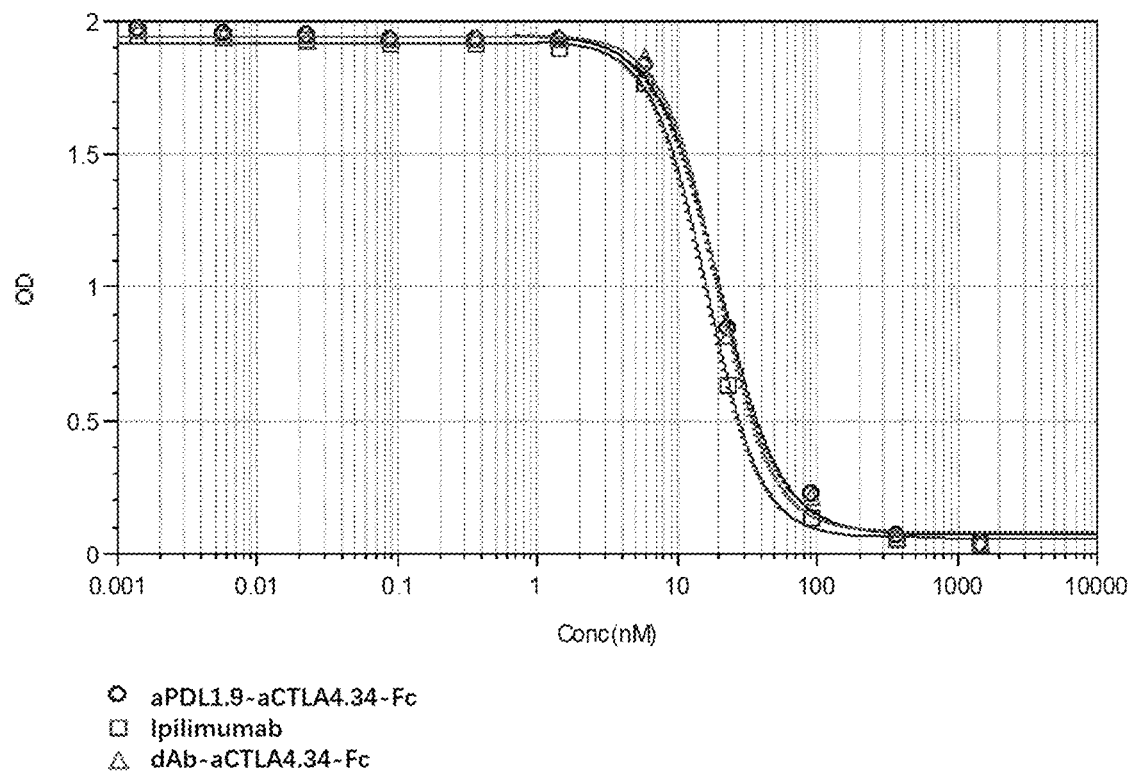
Figure 3:
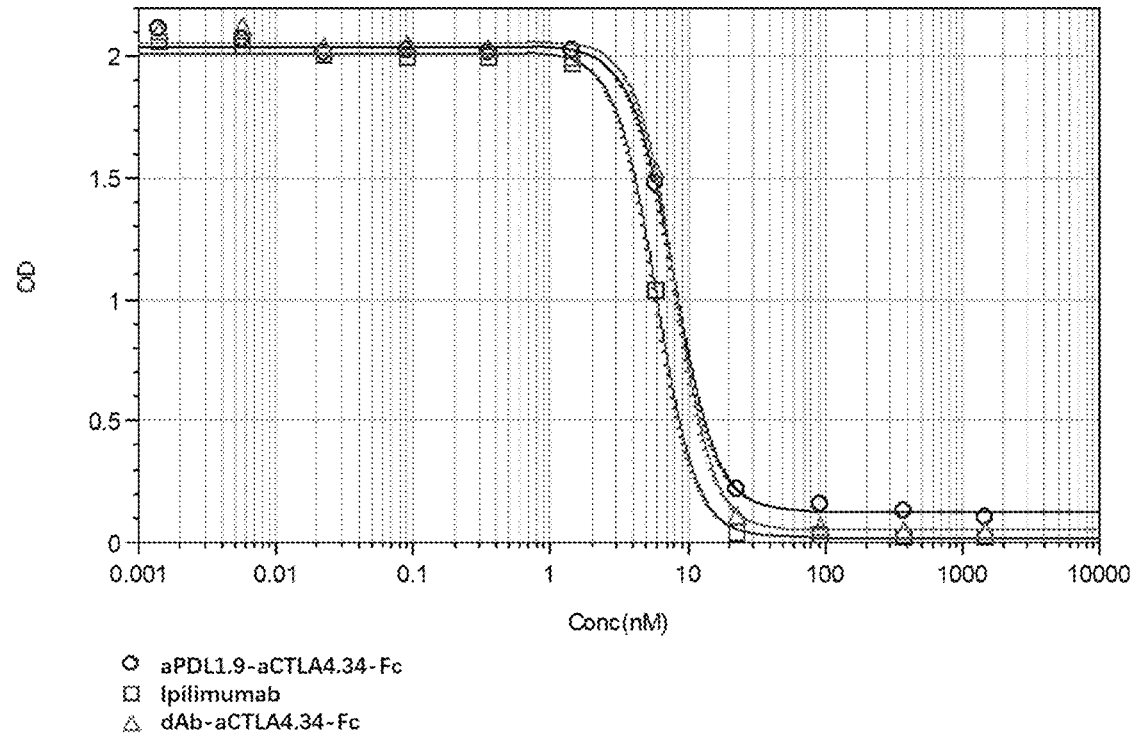

FIG. 3, Panel A shows the abilities of dimers of the present disclosure in blocking binding of PD-L1 to PD-1. It can be seen that either with the ISVD specific for CTLA4 in the N-terminus of the dimer, or with the ISVD specific for PD-L1 in the N-terminus of the dimer, similar blocking abilities were observed, e.g., as shown by the $IC_{50}$ value. Similarly, comparable blocking abilities were observed when a short linker (e.g., GAP) or a longer linker (e.g., GGGGSGGGGSGGGGS) was used between the ISVD specific for CTLA4 and the ISVD specific for PD-L1.

FIG. 3, Panel B shows the abilities of dimers of the present disclosure in blocking binding of PD-L1 to PD-1. It can be seen that the blocking ability of the dimers of the present disclosure is comparable to that of the positive control durvalumab or aPDL1.9-dAb-Fc.

FIG. 3, Panel C shows the abilities of dimers of the present disclosure in blocking binding of PD-L1 to CD80. It can be seen that the blocking ability of the dimers of the present disclosure is comparable to that of the positive control durvalumab or aPDL1.9-dAb-Fc.

FIG. 3, Panel D shows the abilities of dimers of the present disclosure in blocking binding of CTLA4 to CD80. It can be seen that the blocking ability of the dimers aCTLA4.34-aPDL1.9-Fc and aCTLA4.34-L-aPDL1.9-Fc is stronger than that of aPDL1.9-aCTLA4.34-Fc and aPDL1.9-L-aCTLA4.34-Fc.

FIG. 3, Panel E shows the abilities of dimers of the present disclosure in blocking binding of CTLA4 to CD80. It can be seen that the blocking ability of the dimers of the present disclosure is comparable to that of the positive control ipilimumab or dAb-aCTLA4.34-Fc.

FIG. 3, Panel F shows the abilities of dimers of the present disclosure in blocking binding of CTLA4 to CD86. It can be seen that the blocking ability of the dimers of the present disclosure is comparable to that of the positive control dAb-aCTLA4.34-Fc. In addition, the binding ability of the dimers of the present disclosure is slightly weaker than that of ipilimumab.

Example 4

PBMC Stimulation 4.1 Method

The in vitro activity of the dimers of the present disclosure in stimulating immune response, e.g., as revealed by secretion of IL-2 by PBMC cells, was examined. Briefly, PBMCs were isolated from various healthy donors and incubated with Staphylococcal enterotoxin B (SEB) at the concentration of 200 ng/ml, respectively. The dimers of the present disclosure or control molecules of different concentrations (0.015 nM, 0.15 nM, 1.5 nM, or 15 nM) were added. After 5 days of incubation, the supernatant was collected and the IL-2 levels were analyzed with Human IL-2 DuoSet ELISA kits.

4.2 Results

Figure 4:
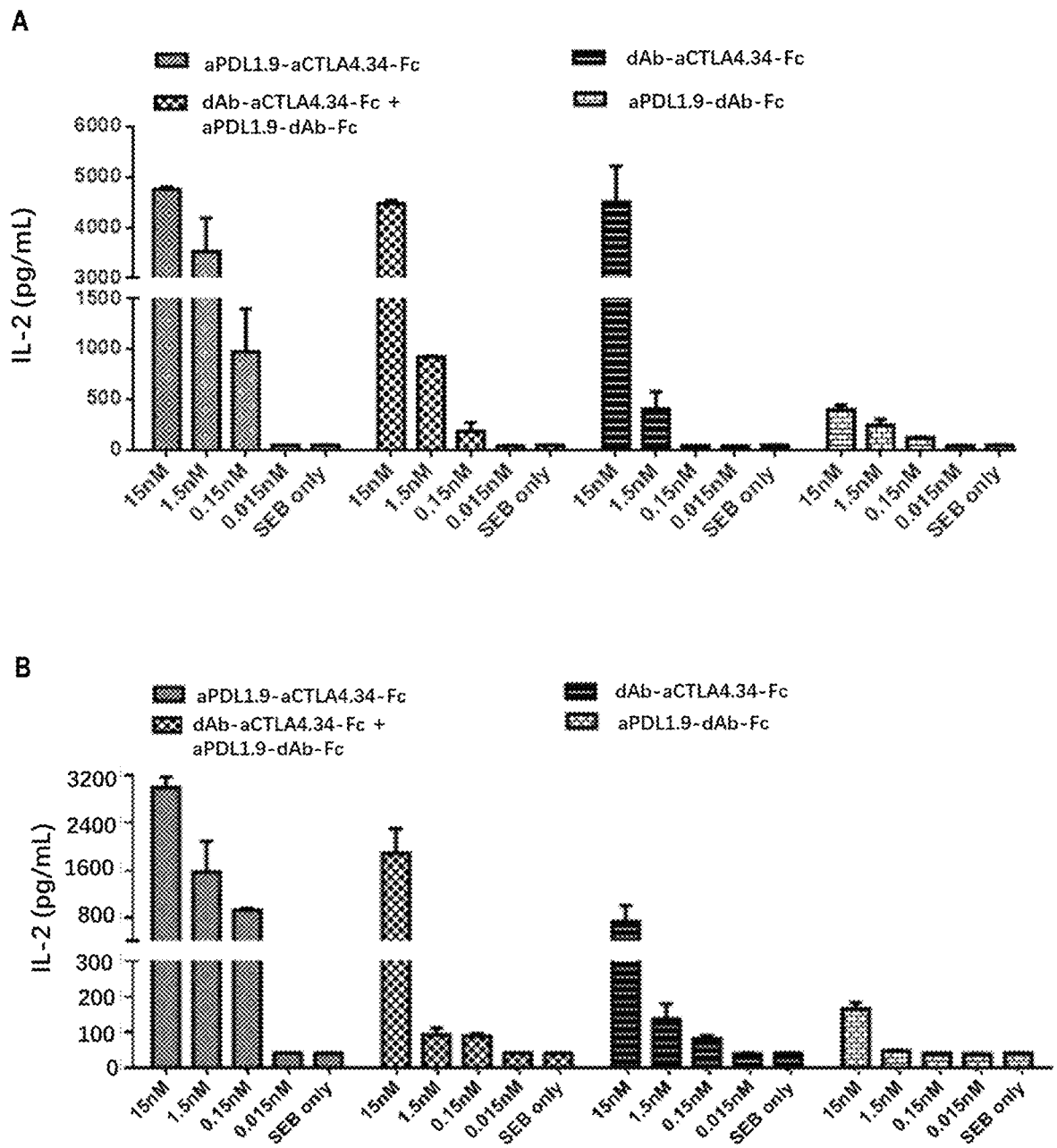
FIG. 4. Panels A-H illustrate stimulation of PBMC by the dimers of the present disclosure.
Figure 4:
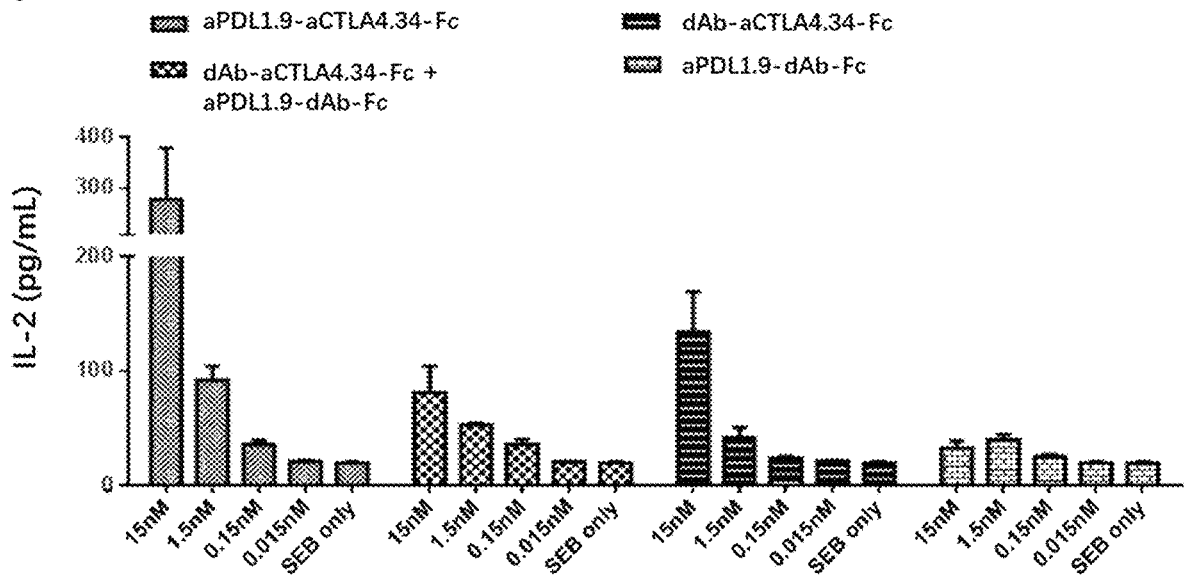
Figure 4:
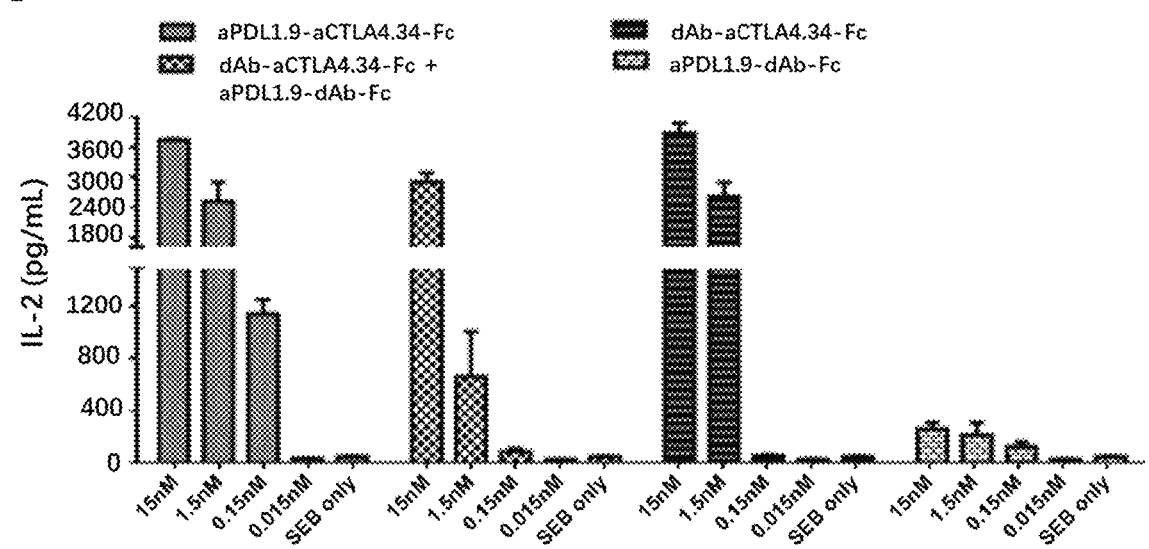
Figure 4:
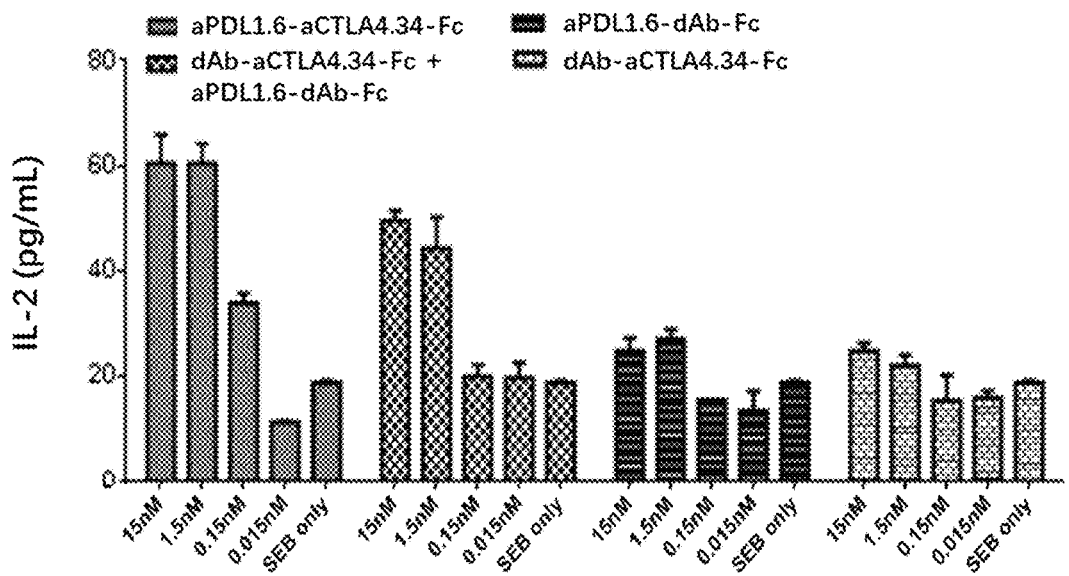
Figure 4:
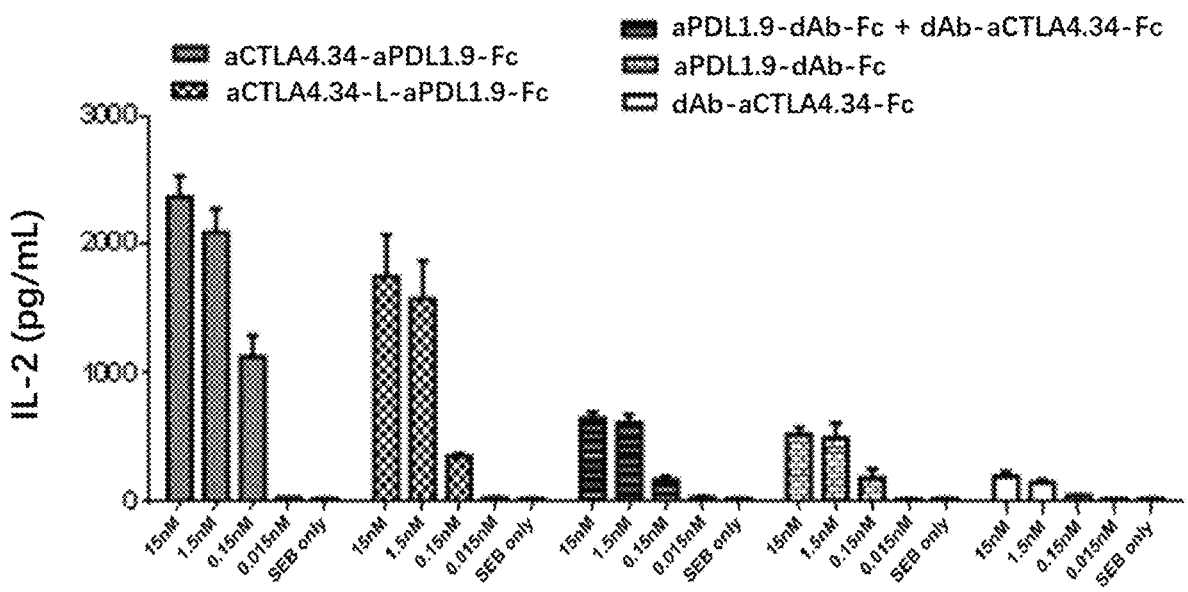
Figure 4:
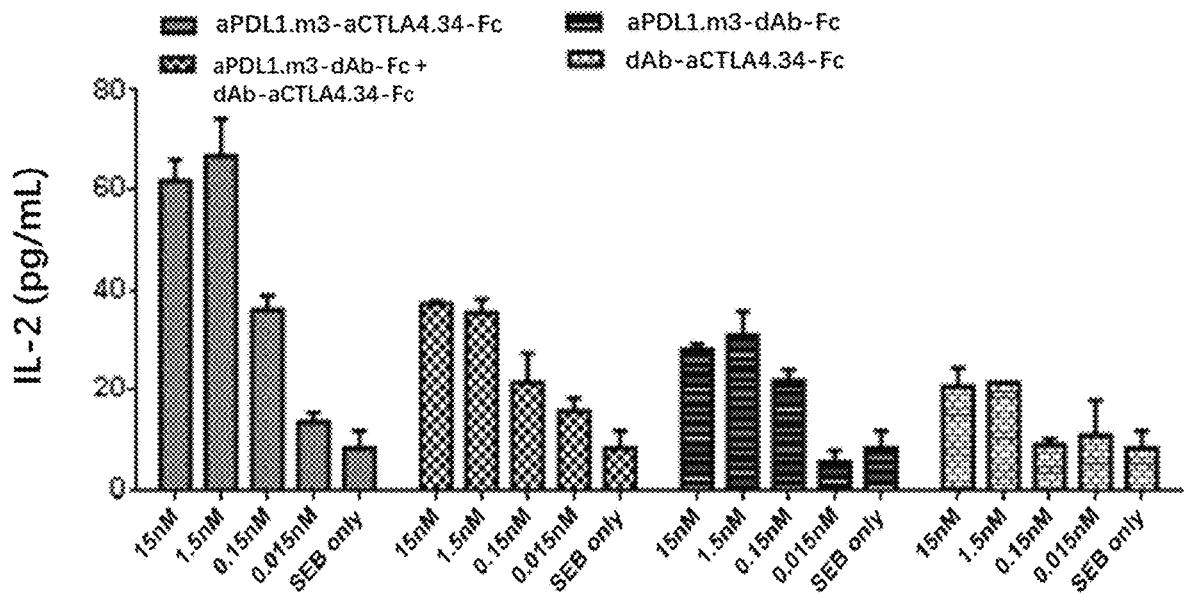
Figure 4:
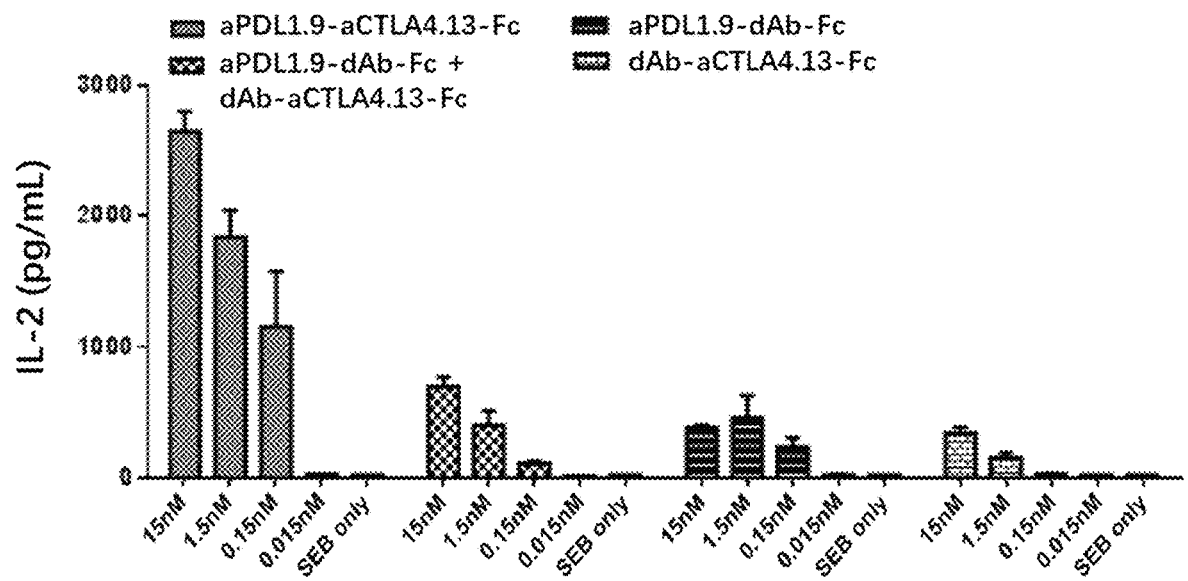

FIG. 4, Panels A-H demonstrate the secretion of IL-2 by SEB stimulated PBMCs, with the addition of the dimers of the present disclosure. The X-coordinate indicates the concentration of the dimers or control molecules added; and the Y-coordinate indicates the concentration of secreted IL-2.

FIG. 4, Panels A-D show the results obtained from PBMCs from 4 different donors. It can be seen that the ability of the dimers of the present disclosure (e.g., aPDL1.9-aCTLA4.34-Fc) in enhancing immune response is significantly stronger than that of the control molecules, or their combination, suggesting a strong synergistic effect.

Similar results were obtained with the dimers aPDL1.6-aCTLA4.34-Fc, aCTLA4.34-aPDL1.9-Fc, aCTLA4.34-L-aPDL1.9-Fc, aPDL1.m3-aCTLA4.34-Fc, and aPDL1.9-aCTLA4.13-Fc, as shown in FIG. 4, Panels E-H.

Example 5

In vivo Tumor Inhibition 5.1 Method
5.1.1 Evaluating the Anti-Tumor Efficacy of the Dimers in a Xenograft Animal Model Transferred with A375-PD-L1 cells and human PBMCs To evaluate the anti-tumor efficacy of the dimers of the present disclosure, a A375-hPD-L1/hPBMCs xenograft mouse model was used. The Human melanoma cell line A375 was stably-transfected with human PD-L1 (designated as A375-hPD-L1) which was used to generate the tumor-bearing xenograft mouse model. Briefly, A375-hPD-L1 cells was mixed with healthy human PBMCs at a ratio of 4:1 and then subcutaneously inoculated into NSG mice. 2-3 hours after tumor inoculation, the mice were administered intraperitoneally with the dimer of the present disclosure (e.g., aPDL1.9-aCTLA4.34-Fc) at doses of 0.1 mg/kg, 0.3 mg/kg, 1 mg/kg, 3 mg/kg, 10 mg/kg or 30 mg/kg twice per week. The tumor volume was measured at the indicated time point.

5.1.2 Evaluating the Anti-Tumor Efficacy of the Dimers in a MC38-hPD-L1 Double Knock-In Model As the dimer of the present disclosure could not cross-react with mouse PD-L1 or mouse CTLA4, a humanized double knock-in (KI) mouse was generated by replacing the mouse CTLA4 and PD-L1 genes with the corresponding human genes, this double knock-in mouse model was used in this example. Moreover, the murine colon carcinoma MC38-hPD-L1 cell line (MC38 cell line with constantly expressed human PD-L1 protein, which generated by stably transfection of human PD-L1 expression cassette into MC38 cell line) was constructed by replacing mouse PD-L1 with human PD-L1. Double KI C57BL/6 mice were subcutaneously inoculated with MC38-hPD-L1 tumor cells ($3 \times 10^5$) in the right front flank. When the mean tumor size reached approximately 60-80 mm$^3$, the tumor-bearing animals were randomly enrolled in one of the three groups. Dimers of the present disclosure (e.g., aPDL1.9-aCTLA4.34-Fc) or control immunoglobulin (IVIG) were intravenously administered to the mice twice per week for a total of 5 times.

5.2 Results

Figure 5:
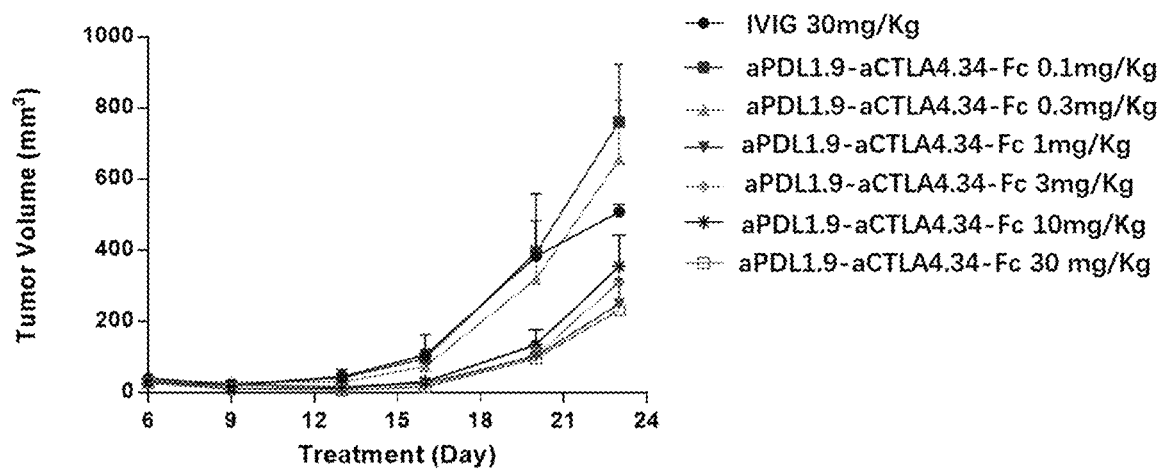
FIG. 5. Panels A and B illustrate inhibition of tumor growth by the dimers of the present disclosure in vivo.
Figure 5:
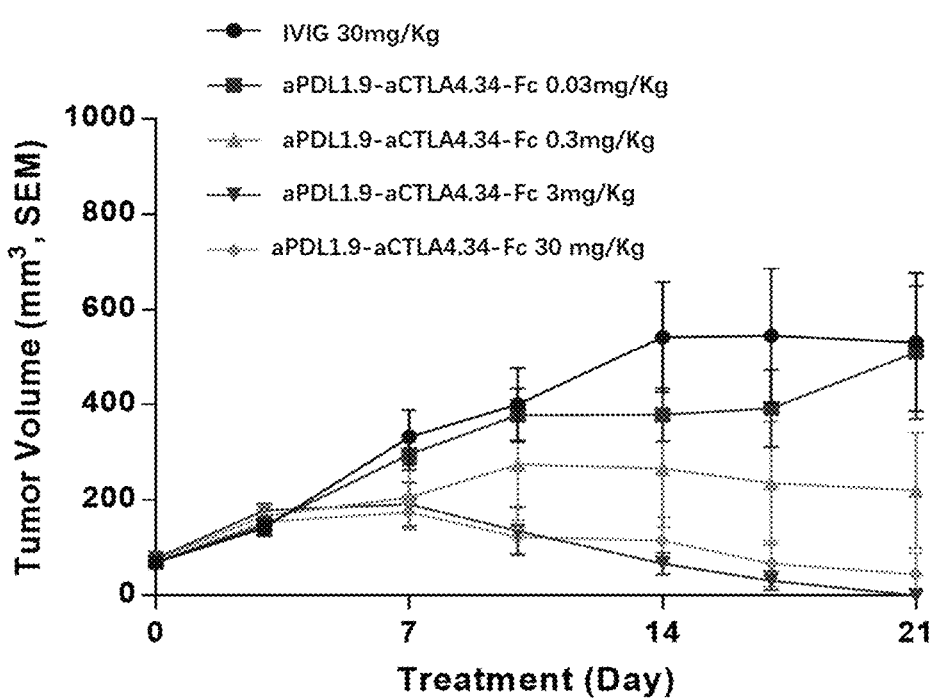

The tumor inhibition effects of the dimers of the present disclosure are shown in FIG. 5, Panels A and B. The X-coordinate indicates the date after administration of the dimers of various concentrations; and the Y-coordinate indicates the tumor volume measured.

FIG. 5, Panel A shows the results obtained from the A375-hPD-L1/PBMC xenograft mouse model, and FIG. 5, Panel B shows the results obtained from the MC38-hPD-L1/Double KI model. IVIG represents intravenous immunoglobulin, which was used as an isotype control.

It can be seen that the dimers of the present disclosure had significant anti-tumor activity in both models, at doses of 0.3 mg/kg or above. Tumors were completely inhibited in the double KI model by the dimers of the present disclosure at doses of 3.0 mg/kg and 30 mg/kg, e.g., on day 21 post first administration.

Example 6

In vivo Pharmacokinetics 6.1 Method

Single-Dose Pharmacokinetic Study in Sprague Dawley Rats

Eight Sprague Dawley (SD) rats were intraveneously administrated with a single dose of 10 mg/kg the dimer of the present disclosure (e.g., aPDL1.9-aCTLA4.34-Fc). Blood samples were obtained at a series time points until day 29 post injection to monitor the concentration of the dimers in the serum of the rats.

6.2 Results $C_{max}$ was reached immediately after administering approximately 305.15±19.34 μg/ml of the dimer, and the mean $T_{1/2}$ was approximately 142.59±29.89 hours, the mean $AUC_{(0-384\ h)}$ was about 10.58±0.68 h*mg/ml, the mean MRT was 127.86±20.75 hours. Other pharmacokinetic parameters are shown in Table 3, and the concentration-time curve is shown in FIG. 6.

Figure 6:
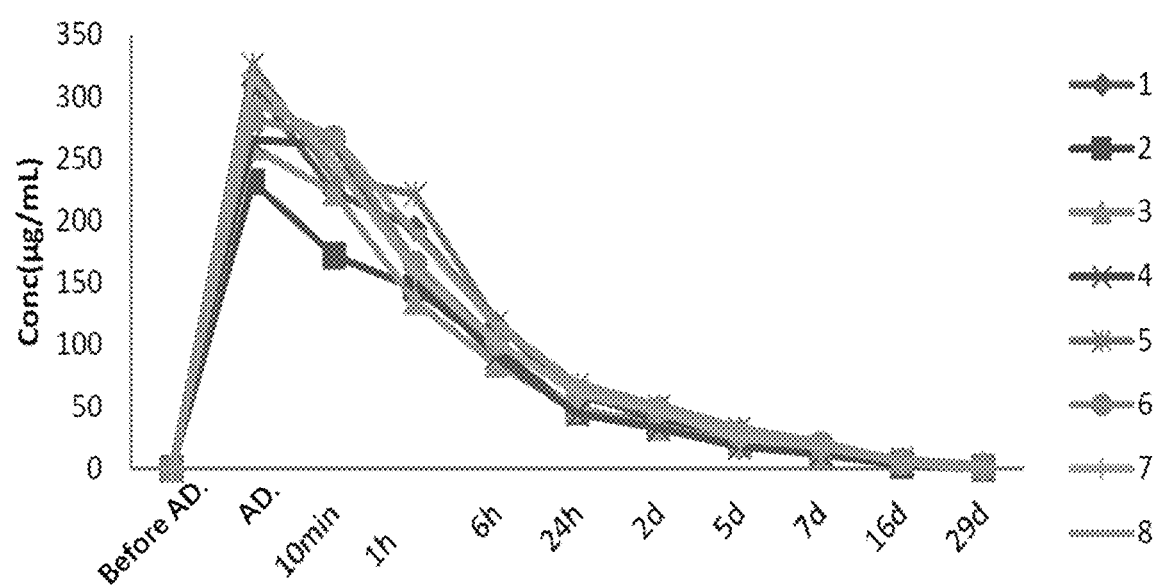
FIG. 6 illustrates the in vivo pK of the dimers of the present disclosure.

In FIG. 6, the X-coordinate indicates the time before and after administration of the dimer; and the Y-coordinate indicates the concentration of the dimer administered. 1-8 indicate the results from eight independent replicates (i.e. 8 different SD rats).

TABLE 3 pharmacokinetic parameters of aPDL1.9-aCTLA4.34-Fc in rats

| | | aPDL1.9-aCTLA4.34-Fc | | | | | | | |
|---|---|---|---|---|---|---|---|---|---|
| | | $T_{1/2}$ (h) | $C_{max}$ (μg/ml) | $AUC_{last}$ (h*mg/ml) | $AUC_{inf}$ (h*mg/ml) | V (ml/kg) | Cl (ml/h/kg) | MRT (h) | $AUC_{(0-384\ h)}$ (h*mg/ml) |
| 10 mpk IV | Mean | 142.59 | 305.15 | 11.55 | 12.06 | 170.39 | 0.83 | 127.86 | 10.58 |
| | SD | 29.87 | 19.34 | 0.65 | 0.75 | 31.84 | 0.05 | 20.75 | 0.68 |

Example 7

Uptake of the Dimers by Tumors

The dimers of the present disclosure (e.g., aPDL1.9-aCTLA4.34-Fc) or the control molecule (e.g., dAb-aCTLA4.34-Fc) was marked with Na$^{125I}$, then purified with PD10 column, washed with 0.02 mol/L phosphate buffer, pH 7.4, the radioactivity of the labelled molecules was examined. Tumor cells were injected into the mice, as described in Example 5 above, when the tumor reached the volume of about 100-200 mm$^3$, the mice were randomly allocated into two groups, with 3 mice each group, one group of mice was for administering the dimer of the present disclosure (e.g., aPDL1.9-aCTLA4.34-Fc) and the other group of mice was for administering the control molecule (e.g., dAb-aCTLA4.34-Fc).

The tumor-bearing mice were anaesthetized with isoflurane, then, the Na$^{125I}$ labeled dimer or control molecule was injected into the tail vein of the mice, at a dose of about 5 MBq (or about 135uCi) per mouse.

The mice were scanned with Micro-SPECT/CT 1 h, 8 h, 1 d, 2 d, 3 d, 4 d, 5 d and 7 d post administration, respectively. Static 10 min SPECT and medium resolution whole-body CT were used. The body weight, dose of injection, time of injection, and remaining dose in the animal bodies were recorded. The amounts of the dimers or the control molecule up-taken by the tumors were quantified using the PMOD software.

Figure 7:
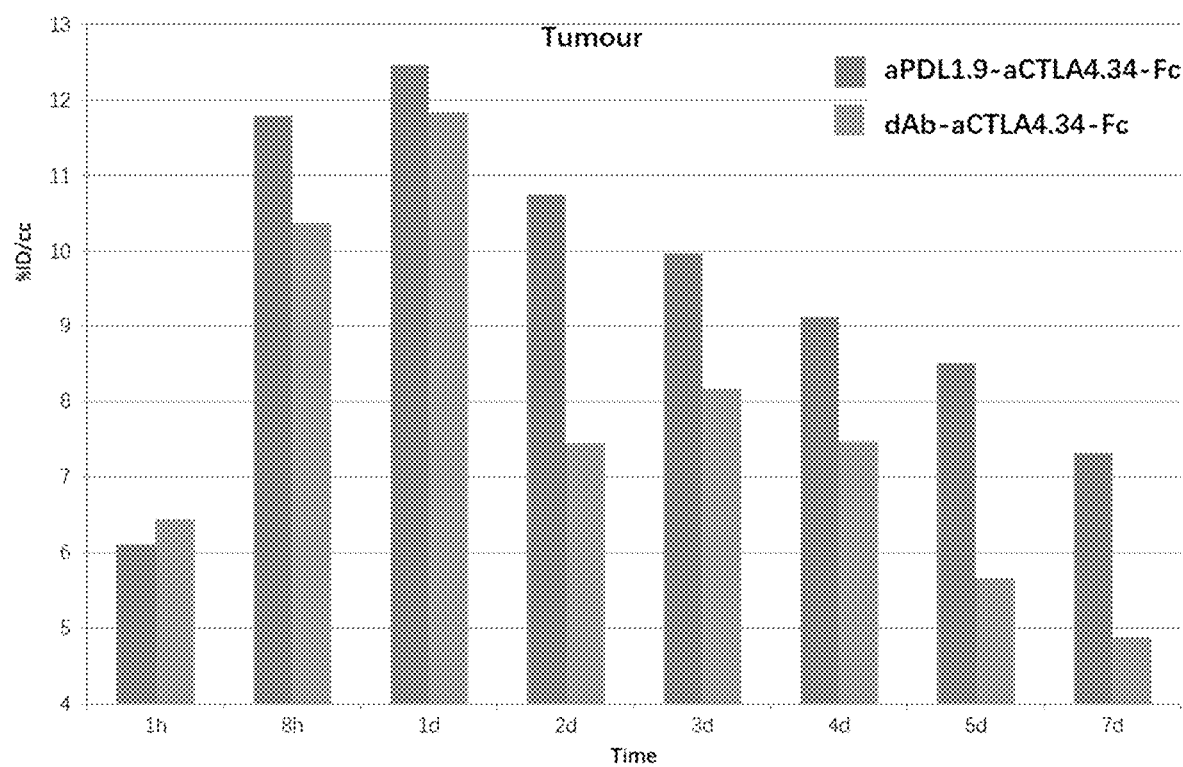
FIG. 7 illustrates uptake of the dimers of the present disclosure by tumors in vivo.

The results are shown in FIG. 7. The X-coordinate indicates the time after administration of the dimer or control molecule; and the Y-coordinate indicates the amounts uptaken by the tumors. It can be seen that comparing to the control molecule, the dimers of the present disclosure were more quickly uptaken and enriched in the tumors and disappeared from the tumors more slowly, indicating potential better efficacy and lower toxicity.

Example 8

Safety and Toxicity of the Present Dimers in Non-Human Primates

The safety and toxicity of the dimers of the present disclosure were examined in non-human primates (e.g., cynomolgus monkeys). When the dimer of the present disclosure (e.g., aPDL1.9-aCTLA4.34-Fc) was administered to the monkeys, no drug-related colitis was observed for all the treatment groups (up to 100 mg/kg/week, which would be equivalent to administering 150 mg/kg/week of ipilimumab in combination with 150 mg/kg/week nivolumab).

However, when a combination of ipilimumab and nivolumab were administered to the monkeys, treatment related diarrhea was found in all treatment group (when 3 mg/kg/week ipilimumab in combination with 10 mg/kg/week nivolumab were administered; or when 10 mg/kg/week ipilimumab in combination with 50 mg/kg/week nivolumab were administered), and one monkey in the high dose group (10 mg/kg/week ipilimumab in combination with 50 mg/kg/week nivolumab) was found dead due to acute gastric dilatation on day 23 post administration. Persistent diarrhea and body weight loss were observed for this monkey. Treatment related colon changes were observed for all the treatment groups.

Accordingly, better safety and less toxicity were observed for the dimer of the present disclosure, comparing to the combination of anti-PD-1 antibody (e.g., nivolumab) and anti-CTLA4 antibody (e.g., ipilimumab).

Example 9

Safety, Efficacy and Pharmacokinetics of the Dimers in Human Patients

The safety, tolerability, pharmacokinetics and efficacy of the dimer of the present disclosure (e.g., aPDL1.9-aCTLA4.34-Fc) were examined in human patients with advanced solid tumors.

Briefly, patients with advanced unresectable or metastatic solid tumors refractory or intolerant to standard therapies were enrolled for the clinical trial. Some of the patients were treated with anti-PD-1 antibody or anti-PD-L1 antibody but showed no response to these therapies prior to being enrolled in the present clinical trial.

The dimer of the present disclosure (e.g., aPDL1.9-aCTLA4.34-Fc) was administered intravenously to the patients biweekly (Q2W). Dose limit toxicity (DLT) evaluation period was 28 days. The administered dose levels were 0.3 mg/kg, 1 mg/kg, 3 mg/kg, 5 mg/kg and 10 mg/kg, respectively. Efficacy evaluation was performed according to RECIST 1.1 every 8 weeks.

10 patients (3 with breast cancers, 1 with cervical cancer, 1 with ovarian cancer, 1 with kidney cancer, 1 with lung cancer, 1 with pancreatic cancer, 1 with peritoneal carcinoma, and 1 with uterus cancer) were enrolled (1 in the 0.3 mg/kg group; 3 in the 1 mg/kg group; 3 in the 3 mg/kg group and 3 in the 5 mg/kg group). The median duration of treatment was 8 (ranging from 2-24 weeks) weeks. 1 DLT was observed with 5 mg/kg dose (a grade 3 immune-related hepatitis without elevation in total bilirubin; reversible in two weeks). The most common (≥30%) treatment-emergent adverse effects (TEAE) were fatigue, diarrhea, nausea, and vomiting. Certain immune-related TEAEs (i.e., lower abdominal pain, arthralgia, hepatic function abnormality, hyperthyroidism, nausea and transaminitis) were observed in 3 patients.

One patient with non-small-cell lung cancer (NSCLC) of the 3 mg/kg cohort showed complete response (CR). Two patients (one with Triple-Negative Breast Cancer (TNBC), and one with nivolumab refractory Renal Cell Carcinoma (RCC)) of the 1 mg/kg cohort had shown long-term stableness of the disease (>12 weeks). In addition, one patient with ovarian cancer of the 3 mg/kg cohort showed significant reduction of tumor size (56% reduction of tumor size).

Faster clearance of the dimer of the present disclosure (e.g., aPDL1.9-aCTLA4.34-Fc) was observed at lower dose (e.g., doses lower than 1 mg/kg), this might be due to target-mediated clearance.

The $T_{1/2}$ of the dimer of the present disclosure was approximately 7 days to 9 days for doses of 3 mg/kg and above.

These results show that the dimer of the present disclosure had acceptable safety profile, which is consistent with the previously reported safety data for other immune checkpoint inhibitors. Preliminary efficacy results are promising. The pharmacokinetic data from the initial 4 cohorts support the biweekly regimen.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

The invention claimed is:

1. A dimer formed by two polypeptide chains, with each of said two polypeptide chains comprising an antibody Fc subunit, wherein said dimer comprises two or more immunoglobulin single variable domains (ISVDs), at least one of said ISVDs is specific for PD-L1, and at least one of said ISVDs is specific for CTLA4;

wherein said ISVD specific for PD-L1 comprises a heavy chain CDR1, CDR2, and CDR3 comprising the amino acid sequences set forth in SEQ ID NOs: 3, 4, and 5, respectively;

wherein said ISVD specific for CTLA4 comprises a heavy chain CDR1, CDR2, and CDR3 comprising the amino acid sequences set forth in SEQ ID NOs: 17, 18, and 19, respectively;

wherein the C-terminus of said ISVD specific for PD-L1 is fused to the N-terminus of the antibody Fc subunit via a linker; and wherein said dimer is a homodimer.

2. The dimer according to claim 1, wherein said antibody Fc subunit is derived from an IgG Fc subunit.

3. The dimer according to claim 1, wherein said antibody Fc subunit comprises an amino acid sequence as set forth in any one of SEQ ID NOs: 35, 38 and 39.

4. The dimer according to claim 1, wherein said ISVD specific for PD-L1 is capable of binding to the N-terminal IgV domain of human PD-L1.

5. The dimer according to claim 1, wherein said ISVD specific for PD-L1 comprises a heavy chain variable domain comprising an amino acid sequence as set forth in any one of SEQ ID NOs: 6, 13, 14 and 15.

6. The dimer according to claim 1, wherein said ISVD specific for CTLA4 comprises a heavy chain variable domain comprising an amino acid sequence as set forth in any one of SEQ ID NOs: 20 and 30-32.

7. The dimer according to claim 1, wherein one or both of said two polypeptide chains comprises an amino acid sequence as set forth in SEQ ID NO: 42 or 43.

8. The dimer according to claim 1, which is capable of blocking binding of PD-L1 to PD-1.

9. The dimer according to claim 1, which is capable of blocking binding of PD-L1 to CD80.

10. The dimer according to claim 1, which is capable of blocking binding of CTLA4 to CD80.

11. The dimer according to claim 1, which is capable of blocking binding of CTLA4 to CD86.

12. An immunoconjugate, comprising the dimer according to claim 1.

13. A pharmaceutical composition comprising an effective amount of the dimer according to claim 1 and a pharmaceutically acceptable excipient.

14. A method for treating a cancer in a subject in need thereof, comprising administering to said subject an effective amount of the dimer according to claim 1.

* * * * *